(12) United States Patent
Vaisburg et al.

(10) Patent No.: US 10,494,345 B2
(45) Date of Patent: Dec. 3, 2019

(54) MODULATORS OF CELL ADHESION, METHODS AND COMPOSITIONS THEREFOR

(71) Applicant: Zonula Incorporated, Montreal (CA)

(72) Inventors: Arkadii Vaisburg, Kirkland (CA); Orest William Blaschuk, Mamaroneck, NY (US)

(73) Assignee: Zonula, Inc., Kirkland, Quebec (CA)

( * ) Notice: Subject to any disclaimer, the term of this patent is extended or adjusted under 35 U.S.C. 154(b) by 0 days.

(21) Appl. No.: 16/148,946

(22) Filed: Oct. 1, 2018

(65) Prior Publication Data

US 2019/0100493 A1    Apr. 4, 2019

Related U.S. Application Data

(60) Provisional application No. 62/567,529, filed on Oct. 3, 2017.

(51) Int. Cl.

| | | |
|---|---|---|
| C07D 211/58 | (2006.01) |
| A61P 35/00 | (2006.01) |
| A61K 9/70 | (2006.01) |
| A61K 45/06 | (2006.01) |
| A61P 19/02 | (2006.01) |

(52) U.S. Cl.
CPC .......... *C07D 211/58* (2013.01); *A61K 9/7023* (2013.01); *A61K 45/06* (2013.01); *A61P 19/02* (2018.01); *A61P 35/00* (2018.01)

(58) Field of Classification Search
CPC ..................... A61K 31/445; C07D 211/58
See application file for complete search history.

(56) References Cited

U.S. PATENT DOCUMENTS

| | | | |
|---|---|---|---|
| 5,505,956 A | 4/1996 | Kim et al. | |
| 5,613,958 A | 3/1997 | Kochinke et al. | |
| 7,456,153 B2 * | 11/2008 | Blaschuk ............. | C07D 211/58 424/130.1 |
| 8,603,986 B2 | 12/2013 | Blaschuk et al. | |
| 2009/0291967 A1 | 11/2009 | Gupta et al. | |

FOREIGN PATENT DOCUMENTS

| | | |
|---|---|---|
| EP | 0566816 A1 | 4/1993 |
| EP | 0710491 A1 | 5/1996 |
| IN | 1962DEL2012 A | 12/2013 |
| WO | 2004044000 A2 | 5/2004 |

OTHER PUBLICATIONS

Ali et al. European Journal of Cell Biology, 2013, 92:229-230.*
Agarwal, S. K., et al., 2008, Coexpression of two mesenchymal cadherins, cadherin 11 and N-cadherin, on murine fibroblast-like synovioctes., Arthritis & Rheumatism, 58, 1044-1054.
Amin, H., et al., 2015, Inhibition of Invasion in Pancreatic Cancer Cells by Conjugate of EPA with β(3,3)-Pip-OH via PI3K/Akt/NF-kB Pathway., A.C.S. Med. Chem. Lett., 6, 1071-1074.
Augustine, C.K., et al., 2008, Targeting N-cadherin enhances antitumor activity of cytotoxic therapies in melanoma treatment., Cancer Res., 68, 3777-3784.
Beasley, G.M., et al., 2009, A phase 1 study of systemic ADH-1 in combination with melphalan via isolated limb infusion in patients with locally advanced in-transit malignant melanoma., Cancer 115, 4766-4774.
Blaschuk, O.W. and Devemy, E., 2009, Cadherins as novel targets for anti-cancer therapy,. European J. Pharmacol. 625: 195-198.
Blaschuk, O.W., 2015, N-cadherin antagonists as oncology therapeutics., Phil. Trans. R. Soc. B., 370, 1661.
Cepek, K.L., et al., 1996, Expression of a candidate cadherin in T lymphocytes., Proc. Nat'l. Acad. Sci. USA 93:6567-6571.
Devemy, E. and Blaschuk, O.W., 2009, Identification of a novel dual E-and Ncadherin antagonist., Peptides 30:1539-1547.
Devemy, E. and Blaschuk, O.W., 2008, Identification of a novel N-cadherin antagonist., Peptides., 29, 1853-1861.
Erez, N., et al., 2004, Induction of apoptosis in cultured endothelial cells by a cadherin antagonist peptide: involvement of fibroblast growth factor receptor-mediated signalling., Exp. Cell Res., 366-378.
Gaudette, F., et al., 2010, Identification of potent and selective VEGFR receptor tyrosine kinase inhibitors having new amide isostere headgroups., Bioorg. Med. Chem. Lett., 20, 848-852.
Harrison, O.J., et al., 2011, The extracellular architecture of adherens junctions revealed by crystal structures of type I cadherins., Structure, 19, 244-256.
Kommi, D.N., et al., 2013, Protecting group-free concise synthesis of (RS)/(S)-lubeluzole., Org Lett., 15, 1158-1161.
Koutsouki, E. et al., 2005, N-cadherin-dependent cell-cell contacts promote human saphenous vein smooth muscle cell survival., Arterioscler. Thromb. Vasc. Biol., 25, 982-988.
Lammens, T., et al., 2012, N-cadherin in neuroblastoma disease: expression and clinical significance., PLoS ONE, 7, e31206.
Mrozik, K.M., et al., 2015, Therapeutic targeting of N-cadherin is an effective treatment for multiple myeloma., Br. J. Haematol. 171, 387-399.
Munro, S.B., et al., 1996, Characterization of cadherins expressed by murine thymocytes., Cellular Immunol., 169, 309-312.
Olive, K.P., et al., 2009, Inhibition of Hedgehog signaling enhances delivery of chemotherapy in a mouse model of pancreatic cancer. Science 1061, 1457-1461.

(Continued)

*Primary Examiner* — Rei Tsang Shiao
(74) *Attorney, Agent, or Firm* — Zackson Law LLC; Saul L. Zackson

(57) ABSTRACT

Compounds with activity as modulators of cell adhesion are disclosed. The compounds are derivatives of piperidin-4-amine. In some embodiments, a compound can be linked to a targeting agent, a pharmaceutically active substance and/or a support material. Methods for enhancing or inhibiting classical cadherin-mediated functions are also disclosed. The compounds can be used for the treatment or prevention of a variety of diseases including cancer. Compositions and devices, including skin patches comprising a compound are also disclosed. In addition, methods of synthesis of the compounds are provided.

10 Claims, 14 Drawing Sheets

Specification includes a Sequence Listing.

(56) References Cited

OTHER PUBLICATIONS

Orr, B., et al., 2012, Identification of stromally expressed molecules in the prostate by tag-profiling of cancer-associated fibroblasts, normal fibroblasts and fetal prostate., Oncogene, 31, 1130-1142.
Pandol, S., et al., 2009, Desmoplasia of pancreatic ductal adenocarcinoma., Clin. Gastroenterol. Hepatol. 7, S44-47.
Perotti, A., et al., 2009, Clinical and pharmacological phase I evaluation of Exherin (ADH-1), a selective anti-N-cadherin peptide in patients with N-cadherin-expressing solid tumours., Ann. Oncol., 20, 741-745.
Raeppel, S., 2009, SAR and biological evaluation of analogues of a small molecule histone deacetylase inhibitor N-(2-aminophenyl)-4-((4-(pyridin-3-yl)pyrimidin-2-ylamino)methyl)benzamide (MGCD0103)., Bioorg. Med. Chem. Lett., 19, 644-649.
Raeppel, S.L., et al., 2012, Identification of a Novel Series of Potent TrkA Receptor Tyrosine Kinase Inhibitors., Int. J. Med. Chem., 2012, 412614.
Raeppel, S., et al., 2010, Identification of a novel series of potent RON receptor tyrosine kinase inhibitors., Bioorg. Med. Chem. Lett., 20, 2745-2749.
Safell, J.L., et al., 1997, Expression of a dominant negative FGF receptor inhibits axonal growth and FGF receptor phosphorylation stimulated by CAMs,. Neuron, 18, 231-242.
Tsutsui, J., et al., 1996, Expression of cadherin-catenin complexes in human leukemia cell lines., J. Biochem., 120, 1034-1039.
Williams, E.J., et al., 1994, Activation of the FGF receptor underlies neurite outgrowth stimulated by L1,N-CAM, and N-cadherin., Neuron, 13, 583-594.

\* cited by examiner

FIG. 2A

| Compound ID | Structure | Compound name |
|---|---|---|
| Compound 2 (scheme 1) | 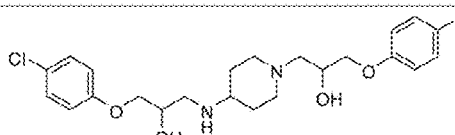 | 1-(4-chlorophenoxy)-3-(1-(3-(4-chlorophenoxy)-2-hydroxypropyl)piperidin-4-ylamino)propan-2-ol<br><br>Chemical Formula: $C_{23}H_{30}Cl_2N_2O_4$<br><br>Molecular Weight: 469.40 |
| Compound 4 (scheme 2) | 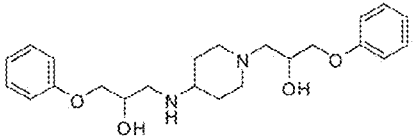 | 1-(1-(2-hydroxy-3-phenoxypropyl)piperidin-4-ylamino)-3-phenoxypropan-2-ol<br><br>Chemical Formula: $C_{23}H_{32}N_2O_4$<br><br>Molecular Weight: 400.51 |
| Compound 5 (scheme 3) | 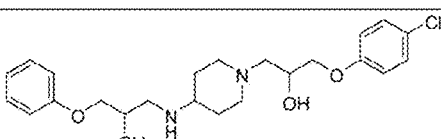 | 1-(4-chlorophenoxy)-3-(4-(2-hydroxy-3-phenoxypropylamino)piperidin-1-yl)propan-2-ol<br><br>Chemical Formula: $C_{23}H_{31}ClN_2O_4$<br><br>Molecular Weight: 434.96 |

FIG. 2B

| | | |
|---|---|---|
| Compound 6 (scheme 4) | (structure) | 1-(4-chlorophenoxy)-3-(1-(2-hydroxy-3-phenoxypropyl)piperidin-4-ylamino)propan-2-ol<br><br>Chemical Formula: $C_{23}H_{31}ClN_2O_4$<br><br>Molecular Weight: 434.96 |
| Compound 7 (scheme 5) | (structure) | 1-(4-((2-hydroxy-3-phenoxypropyl)(methyl)amino)piperidin-1-yl)-3-phenoxypropan-2-ol<br><br>Chemical Formula: $C_{24}H_{34}N_2O_4$<br><br>Molecular Weight: 414.54 |
| Compound 10 (scheme 6) | (structure) | (S)-1-(3,4-dichlorophenoxy)-3-(1-((S)-3-(3,4-dichlorophenoxy)-2-hydroxypropyl)piperidin-4-ylamino)propan-2-ol<br><br>Chemical Formula: $C_{23}H_{28}Cl_4N_2O_4$<br><br>Molecular Weight: 538.29 |

FIG. 2C

| | | |
|---|---|---|
| Compound 13 (scheme 7) | [structure] | (R)-1-(3,4-dichlorophenoxy)-3-(1-((R)-3-(3,4-dichlorophenoxy)-2-hydroxypropyl)piperidin-4-ylamino)propan-2-ol<br><br>Chemical Formula: $C_{23}H_{28}Cl_4N_2O_4$<br><br>Molecular Weight: 538.29 |
| Compound 15 (scheme 8) | [structure] | (S)-1-(3,4-dichlorophenoxy)-3-(4-(((S)-2-hydroxy-3-(4-methoxyphenoxy)propyl)amino)piperidin-1-yl)propan-2-ol<br><br>Chemical Formula: $C_{24}H_{32}Cl_2N_2O_5$<br><br>Molecular Weight: 499.43 |
| Compound 16 (scheme 9) | [structure] | (R)-1-(3,4-dichlorophenoxy)-3-(4-(((S)-2-hydroxy-3-(4-methoxyphenoxy)propyl)amino)piperidin-1-yl)propan-2-ol<br><br>Chemical Formula: $C_{24}H_{32}Cl_2N_2O_5$<br>Molecular Weight: 499.43 |

FIG. 2D

| Compound 18 (scheme 10) | [structure] | (S)-1-(3,4-dichlorophenoxy)-3-(4-((R)-2-hydroxy-3-(4-methoxyphenoxy)propylamino)piperidin-1-yl)propan-2-ol<br><br>Chemical Formula: $C_{24}H_{32}Cl_2N_2O_5$<br><br>Molecular Weight: 499.43 |
|---|---|---|
| Compound 19 (scheme 11) | [structure] | (R)-1-(3,4-dichlorophenoxy)-3-(4-((R)-2-hydroxy-3-(4-methoxyphenoxy)propylamino)piperidin-1-yl)propan-2-ol<br><br>Chemical Formula: $C_{24}H_{32}Cl_2N_2O_5$<br><br>Molecular Weight: 499.43 |

COMPOUND 15

DMSO   0.5 μM   1 μM   5 μM   10 μM   50 μM

Arrow: unruptured follicle with clear evidence of COC expansion
Asterisk: apparent ruptured & luteinising structure

MODULATORS OF CELL ADHESION, METHODS AND COMPOSITIONS THEREFOR

REFERENCE TO PRIOR APPLICATION

This application claims benefit of and priority to U.S. Provisional Application 62/567,529 filed on Oct. 3, 2017. Application 62/567,529 is incorporated by reference in its entirety.

INCORPORATION BY REFERENCE OF SEQUENCE LISTING

The Sequence Listing, which is a part of the present disclosure, includes a computer readable form and a written sequence listing comprising nucleotide and/or amino acid sequences. The subject matter of the Sequence Listing is incorporated herein by reference in its entirety.

FIELD

The present invention relates generally to small molecule compounds, compositions and methods for modulating cadherin-mediated functions.

INTRODUCTION

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins (also referred to herein as CADs) are a family of calcium-dependent CAMs (Hulpiau, P., van Roy, F., Int. J. Biochem. Cell Biol. 41: 349-369, 2009). The classical cadherins (abbreviated classical CADs) are integral membrane glycoproteins that generally mediate cell adhesion through homophilic interactions (a CAD on the surface of one cell binds to an identical CAD on the surface of another cell), although classical CADs also appear to be capable of forming heterotypic complexes with one another under certain circumstances and with lower affinity. Classical CADs have been shown to regulate epithelial, endothelial, mural, stromal, neural, cancer and stem cell adhesion, with different CADs expressed on different cell types. N (neural)-cadherin is predominantly expressed by neural cells, endothelial cells, smooth muscle cells (e.g. pericytes), stromal cells (e.g. fibroblasts) and a variety of cancer cell types. E (epithelial)-cadherin is predominantly expressed by epithelial cells and stem cells. Other CADs are P (placental)-cadherin, which is found in human skin and certain cancer cell types (e.g. bladder cancer cells) and R (retinal)-cadherin. Detailed discussions of the classical cadherins are provided in Blaschuk, O. W., Phil. Trans. R. Soc. B 370: 1661, 2015, Harrison, O. J., et al., Structure 19: 244-256, 2011 and Hulpiau, P., and van Roy, F., Int. J. Biochem. Cell Biol. 41: 349-369, 2009.

The structures of the classical CADs are generally similar. As illustrated in FIG. 1, classical CADs are composed of five extracellular domains (EC1-EC5), a single hydrophobic domain (TM) that traverses the plasma membrane (PM), and two cytoplasmic domains (CP1 and CP2). The calcium binding motifs are shown by DXNDN (SEQ ID NO: 1), DXD, XDXE (SEQ ID NO: 2), DVNE (SEQ ID NO: 3) and LDRE (SEQ ID NO: 4). The classical cell adhesion recognition (CAR) sequence (HAV) and a Trp-containing CAR sequence (D/E-W-V-I/V/M-P/A-P, SEQ ID NO: 5), are shown within EC1. Each of the extracellular domains comprises about 110 amino acids.

Although cell adhesion is required for certain normal physiological functions, there are situations in which the level of cell adhesion is undesirable. For example, many pathologies (such as autoimmune diseases, cancer and inflammatory diseases) involve abnormal cellular adhesion. Cell adhesion can also play a role in graft rejection. In such circumstances, modulation of cell adhesion may be desirable.

N-cadherin has emerged as an important oncology therapeutic target. It mediates the formation of blood vessels (angiogenesis) and is involved in the maintenance of blood vessel structural integrity (Blaschuk, O. W. and Devemy, E., European J. Pharmacol. 625: 195-198, 2009). Tumor growth is dependent on these processes. N-cadherin expression has also been documented in numerous types of poorly differentiated tumors. This CAM is also involved in regulating the proliferation, survival, invasiveness and metastasis of cancer cells. Disruption of N-cadherin homophilic intercellular interactions using antagonists therefore presents a possible strategy for anti-cancer therapies. A detailed discussion of the potential for N-cadherin antagonists to serve as anti-cancer agents is provided in Blaschuk, O. W., Phil. Trans. R. Soc. B 370:1661, 2015.

Several references disclose antagonists of cadherin activity. U.S. Pat. No. 8,883,501 to Ward discloses biological antagonists of E-cadherin. This reference does not disclose or discuss antagonists that are not proteins or other biologically produced molecules. Lammens, T., et al., PLoS ONE 7: e31206, 2012, Beasley G. M., et al. Cancer 115: 4766-4774, 2009, Perotti A., et al., Ann. Oncol. 20: 741-745, 2009 and Augustine, C. K., et al., Cancer Res. 68: 3777-3784. 2008 disclose ADH-1, a cyclic peptide antagonist of N-cadherin which contains the cell adhesion recognition site His-Ala-Val believed important in N-cadherin-mediated adhesion. U.S. Pat. No. 7,456,153 to Blaschuk and Michaud discloses a compound that facilitates transdermal delivery of hydrocortisone through nude mouse skin in a Franz cell assay.

There are currently no adequate treatments for a variety of cancers, such as pancreatic and prostate cancers. Accordingly, there is a need for compounds that inhibit cell adhesion which can be used in cancer treatments.

Skin patches are a convenient tool for administering drugs through the skin. However, the use of skin patches has been limited to small, hydrophobic molecules because of epithelial and endothelial cell permeability barriers arising from classical cadherin-mediated cell adhesion. Such barriers create difficulties for the delivery of drugs to specific tissues and tumors within the body. Similarly, endothelial cells render blood capillaries largely impermeable to drugs, and the blood-/brain barrier hampers the targeting of drugs to the central nervous system. In addition, many solid tumors develop internal permeability barriers that limit the delivery of anti-cancer drugs and antibodies to cancer cells residing within tumors.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While efficiency has been enhanced using a variety of chemical agents that disrupt cell adhesion, such agents are typically associated with undesirable side-effects, may require invasive procedures for administration and may result in irreversible effects.

The immune system plays an important role in killing cancer cells (Joyce, J. A. and Fearon, D. T., Science 348: 74-80, 2015). Unfortunately, cytotoxic T cells of the immune system are prevented from contacting and killing the cancer cells of solid tumors by barriers formed by fibroblasts in the stromal microenvironment. Methods are needed to enhance the permeability of the tumor stroma so that T cells can gain access to the cancer cells.

Nanoparticles carrying drugs are also prevented from gaining access to cancer cells of solid tumors by the stroma. Methods are needed to increase the permeability of the tumor stroma thereby allowing nanoparticles to gain access to the cancer cells.

Accordingly, there is a need for compounds that modulate cell adhesion and enhance T cell, nanoparticle and drug delivery across permeability barriers.

There are currently no adequate treatments for lung fibrosis, in particular idiopathic pulmonary fibrosis. Accordingly, there is a need for cell adhesion-modulating compounds which can be used in the treatment of fibrosis.

SUMMARY

The present inventors disclose small molecule cell adhesion antagonists, and methods for inhibition of CAD-mediated cell adhesion, including, without limitation, inhibition of classical CAD-mediated cell adhesion and inhibition of non-classical CAD-mediated cell adhesion. The antagonists described herein, in various embodiments, can be used to modulate a cell function mediated by a classical cadherin or by another class of cell adhesion molecule, such as a non-classical cadherin. In various configurations, an antagonist of the present teachings can interfere with activity of a classical CAD expressed on a cell. In various configurations, a classical CAD can be selected from the group consisting of E-cadherin, N-cadherin, P-cadherin, R-cadherin, and any combination thereof.

In some embodiments, a cell adhesion antagonist of the present teachings can be a compound of structure:

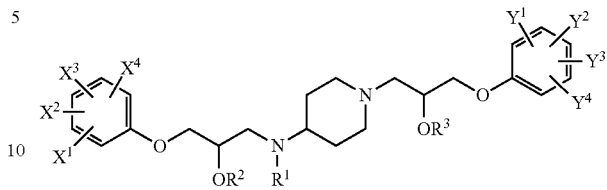

(Structure I), a pharmaceutically acceptable salt, a stereoisomer or a prodrug thereof, wherein: $R^1$ can be selected from the group consisting of H, $C_1$-$C_6$ alkyl, —C(=O)$C_1$-$C_6$ alkyl and —C(=O)O$C_1$-$C_6$ alkyl; and $R^2$ and $R^3$ can each be independently selected from the group consisting of H, $C_1$-$C_6$ alkyl, —C(=O)$C_1$-$C_6$ alkyl and —C(=O)O$C_1$-$C_6$ alkyl; $X^1$, $X^2$, $X^3$, $X^4$, $X^4$, $Y^2$, $Y^3$ and $Y^4$ can each be independently selected from the group consisting of H, OH, halo, cyano, nitro, azido, $C_1$-$C_6$-alkyl, $C_1$-$C_6$-alkoxy, —C(=O)$C_1$-$C_6$ alkyl, $CF_3$, $OCF_3$, $CCl_3$, $SO_2C_1$-$C_6$ alkyl, $SO_2N(R^1)C_1$-$C_6$ alkyl, $N(R^1)SO_2C_1$-$C_6$ alkyl, $P(O)(C_1$-$C_6$ alkyl$)_2$, $NR^2R^3$, COOH, C(=O)O$C_1$-$C_6$ alkyl, C(=O)N($R^1$)$C_1$-$C_6$ alkyl, $N(R^1)$C(=O)$C_1$-$C_6$ alkyl, $N(R^1)$C(=O)N($R^1$)$C_1$-$C_6$ alkyl and $N(R^1)$C(=O)O$C_1$-$C_6$ alkyl, provided that the compound is not 1-(3,4-difluorophenoxy)-3-(1-(3-(3,4-difluorophenoxy)-2-hydroxypropyl)piperidin-4-ylamino)propan-2-ol

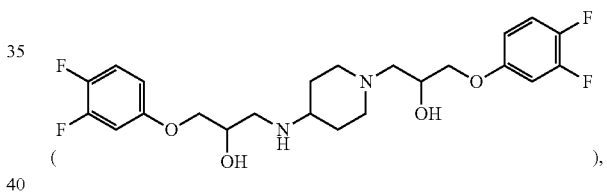

1-(3,4-dichlorophenoxy)-3-(4-(2-hydroxy-3-(4-methoxyphenoxy)propylamino)piperidin-1-yl)propan-2-ol

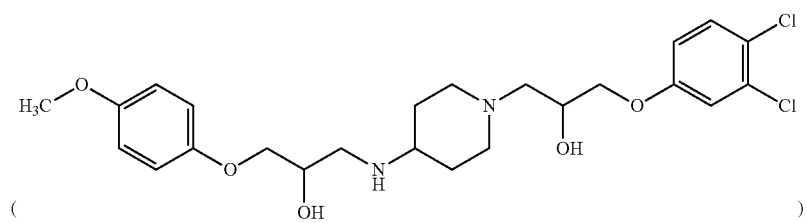 [SMILES: COc1ccc(OCC(O)CNC2CCN(CC(O)COc3ccc(Cl)c(Cl)c3)CC2)cc1]

or (R)-1-(3,4-dichlorophenoxy)-3-(4-((R)-2-hydroxy-3-(4-methoxyphenoxy)propylamino)piperidin-1-yl)propan-2-ol

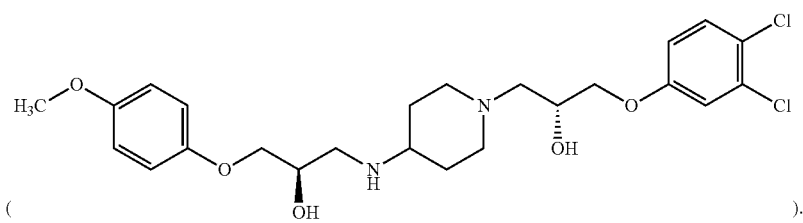 [SMILES: COc1ccc(OC[C@H](O)CNC2CCN(C[C@@H](O)COc3ccc(Cl)c(Cl)c3)CC2)cc1]

In various configurations, a compound of the present teachings can be 1-(4-chlorophenoxy)-3-(1-(3-(4-chlorophenoxy)-2-hydroxypropyl)piperidin-4-ylamino)propan-2-ol (compound 2); 1-(1-(2-hydroxy-3-phenoxypropyl)piperidin-4-ylamino)-3-phenoxypropan-2-ol (compound 4), 1-(4-chlorophenoxy)-3-(4-(2-hydroxy-3-phenoxypropylamino) piperidin-1-yl)propan-2-ol (compound 5); 1-(4-chlorophenoxy)-3-(1-(2-hydroxy-3-phenoxypropyl) piperidin-4-ylamino)propan-2-ol (compound 6); 1-(4-((2-hydroxy-3-phenoxypropyl)(methyl)amino)piperidin-1-yl)-3-phenoxypropan-2-ol (compound 7); (S)-1-(3,4-dichlorophenoxy)-3-(1-((S)-3-(3,4-dichlorophenoxy)-2-hydroxypropyl)piperidin-4-ylamino)propan-2-ol (compound 10); (R)-1-(3,4-dichlorophenoxy)-3-(1-((R)-3-(3,4-dichlorophenoxy)-2-hydroxypropyl)piperidin-4-ylamino)propan-2-ol (compound 13); (S)-1-(3,4-dichlorophenoxy)-3-(4-(((S)-2-hydroxy-3-(4-methoxyphenoxy) propyl)amino)piperidin-1-yl)propan-2-ol (compound 15); (R)-1-(3,4-dichlorophenoxy)-3-(4-(((S)-2-hydroxy-3-(4-methoxyphenoxy)propyl)amino)piperidin-1-yl)propan-2-ol (compound 16); (S)-1-(3,4-dichlorophenoxy)-3-(4-((R)-2-hydroxy-3-(4-methoxyphenoxy)propylamino)piperidin-1-yl)propan-2-ol (compound 18); or (R)-1-(3,4-dichlorophenoxy)-3-(4-((R)-2-hydroxy-3-(4-methoxyphenoxy) propylamino)piperidin-1-yl)propan-2-ol (compound 19), as depicted in FIG. 2A-D.

In some embodiments, the present teachings include compositions comprising a cell adhesion antagonist described herein and a pharmaceutically acceptable carrier, excipient or diluent. A composition of the present teachings can further comprise one or more heterologous compounds. In various configurations, a heterologous compound can be, without limitation, a pharmaceutically active substance, a targeting agent, a detectable marker, or a solid support. A solid support can be, for example and without limitation, a polymeric matrix, a plastic dish, a plastic tube, a suture, a membrane, an ultrathin film, a bioreactor, a nanoparticle or a microparticle. A detectable marker can be, for example and without limitation, an antigen such as a polypeptide that can be detected with an antibody, or an enzyme that can be detected with a chromogenic or fluorogenic substrate.

In various embodiments, the present teachings include methods of synthesizing cell adhesion antagonists disclosed herein. Methods of the present teachings include synthesis schemes for compounds such as 1-(4-aminopiperidin-1-yl)-3-(4-chlorophenoxy)propan-2-ol (1), 1-(4-chlorophenoxy)-3-(1-(3-(4-chlorophenoxy)-2-hydroxypropyl)piperidin-4-ylamino)propan-2-ol (2), 1-(4-aminopiperidin-1-yl)-3-phenoxypropan-2-ol (3), 1-(1-(2-hydroxy-3-phenoxypropyl)piperidin-4-ylamino)-3-phenoxypropan-2-ol (4), 1-(4-Chlorophenoxy)-3-(4-(2-hydroxy-3-phenoxypropylamino)piperidin-1-yl)propan-2-ol (5), 1-(4-Chlorophenoxy)-3-(1-(2-hydroxy-3-phenoxypropyl) piperidin-4-ylamino)propan-2-ol (6), 1-(4-((2-Hydroxy-3-phenoxypropyl)(methyl)amino)piperidin-1-yl)-3-phenoxypropan-2-ol (7), (S)-2-((3,4-Dichlorophenoxy) methyl)oxirane (8), (S)-1-(4-Aminopiperidin-1-yl)-3-(3,4-dichlorophenoxy)propan-2-ol (9), (S)-1-(3,4-dichlorophenoxy)-3-(1-((S)-3-(3,4-dichlorophenoxy)-2-hydroxypropyl)piperidin-4-ylamino)propan-2-ol (10), (R)-2-((3,4-Dichlorophenoxy)methyl)oxirane (11), (R)-1-(4-Aminopiperidin-1-yl)-3-(3,4-dichlorophenoxy)propan-2-ol (12), (R)-1-(3,4-dichlorophenoxy)-3-(4-((R)-2-hydroxy-3-(4-methoxyphenoxy)propylamino)piperidin-1-yl)propan-2-ol (13), (S)-2-((4-Methoxyphenoxy)methyl)oxirane (14), (S)-1-(3,4-dichlorophenoxy)-3-(4-(((S)-2-hydroxy-3-(4-methoxyphenoxy)propyl)amino)piperidin-1-yl)propan-2-ol (15), (R)-1-(3,4-dichlorophenoxy)-3-(4-(((S)-2-hydroxy-3-(4-methoxyphenoxy)propyl)amino)piperidin-1-yl)propan-2-ol (16), (R)-2-((4-Methoxyphenoxy)methyl)oxirane (17), (S)-1-(3,4-dichlorophenoxy)-3-(4-((R)-2-hydroxy-3-(4-methoxyphenoxy)propylamino)piperidin-1-yl)propan-2-ol (18) and (R)-1-(3,4-Dichlorophenoxy)-3-(4-((R)-2-hydroxy-3-(4-methoxyphenoxy)propylamino)piperidin-1-yl) propan-2-ol (19).

In various configurations, the present teachings include cell adhesion antagonists designated herein as compounds A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-53, A-54, A-55, A-56, A-57, A-58, A-59 and A-60. These compounds have structures as follows:

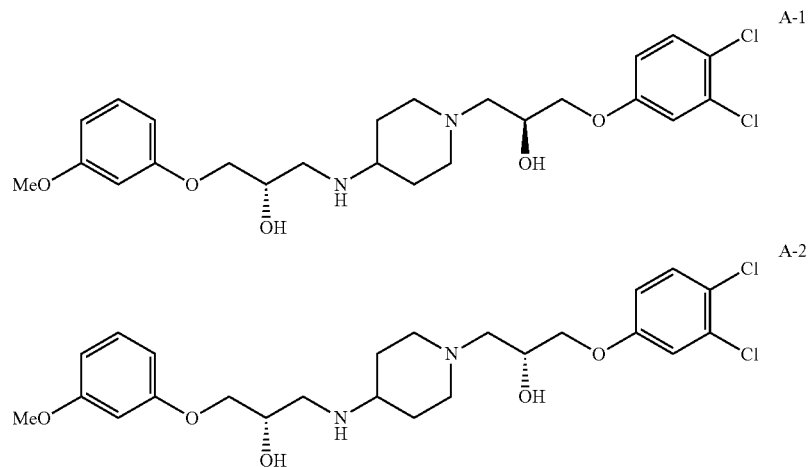

-continued
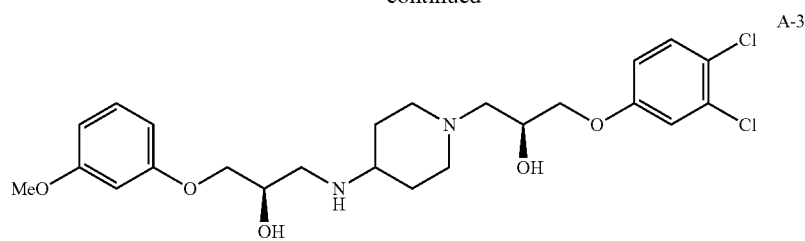
A-3
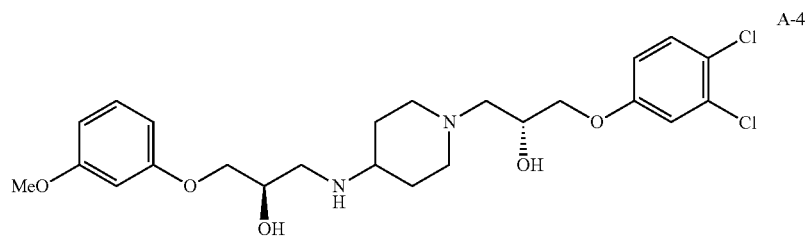
A-4
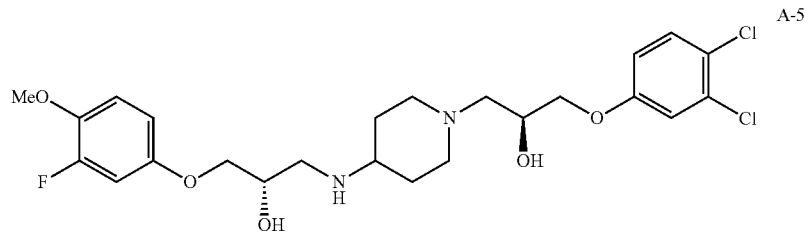
A-5
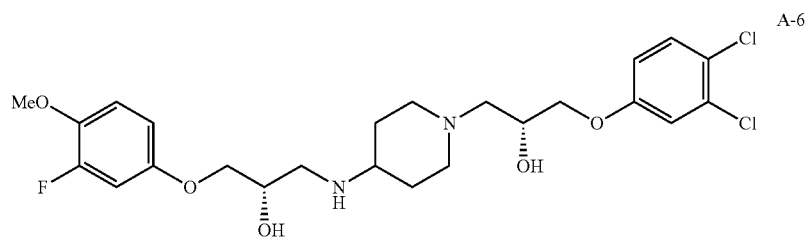
A-6
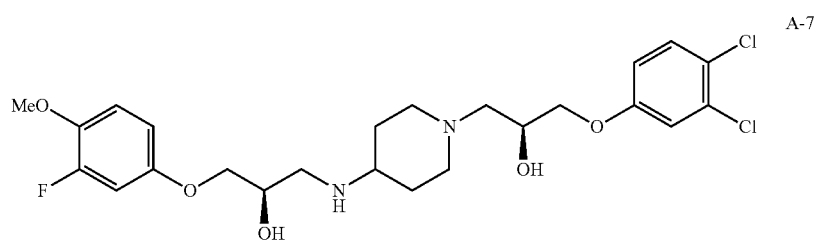
A-7
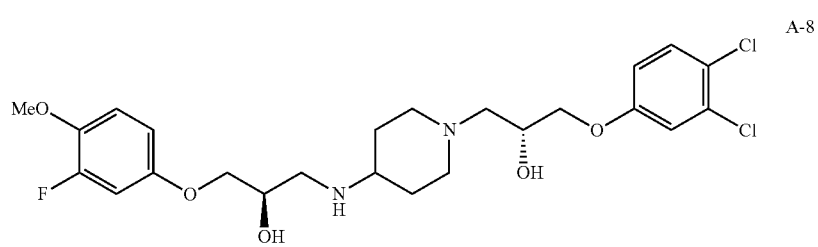
A-8
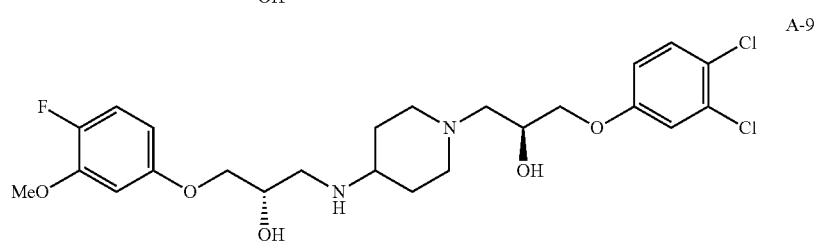
A-9

-continued
A-10
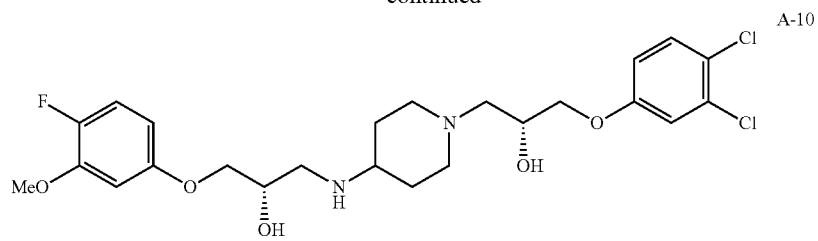
A-11
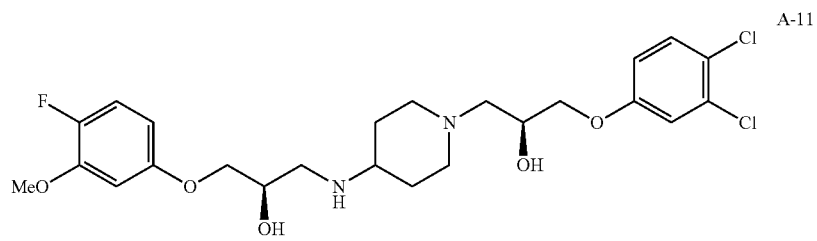
A-12
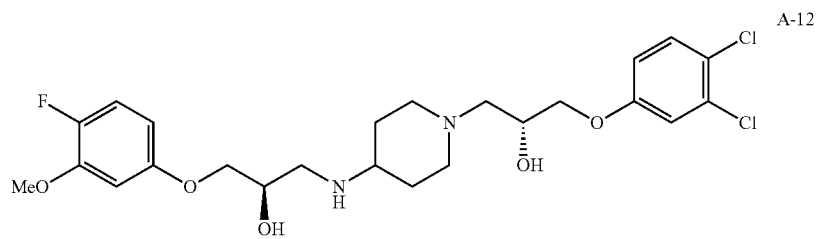
A-13
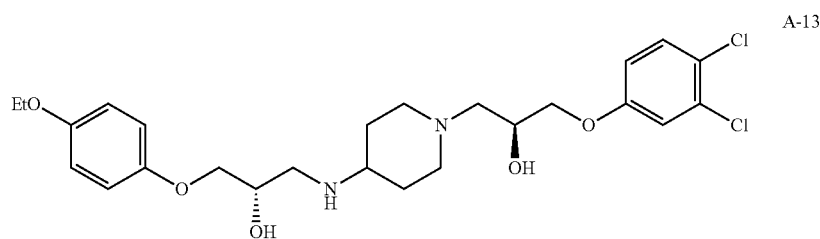
A-14
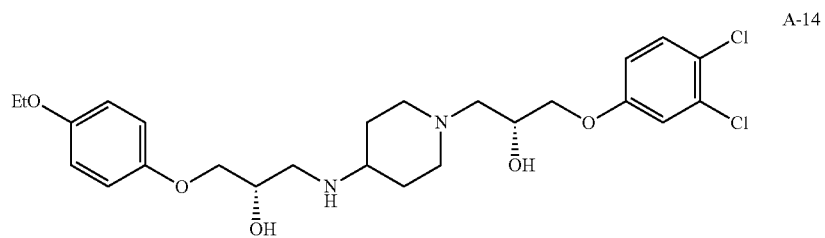
A-15
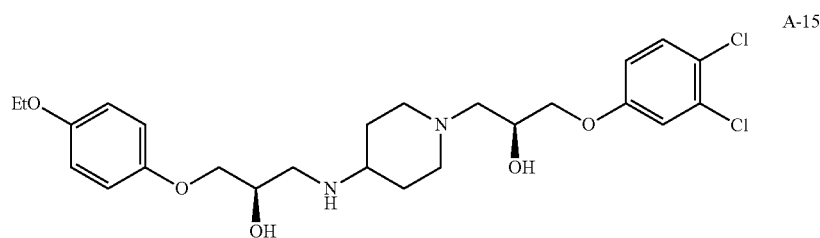
A-16
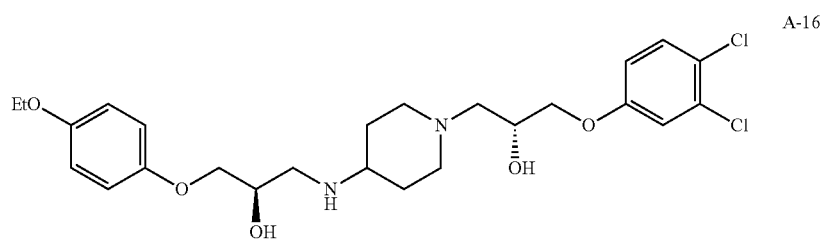

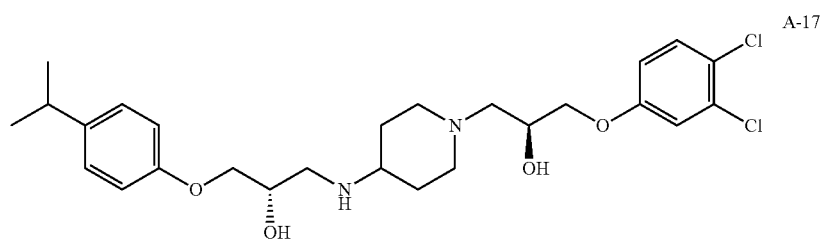
A-17
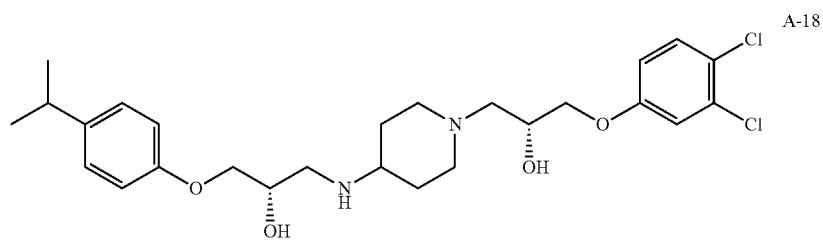
A-18
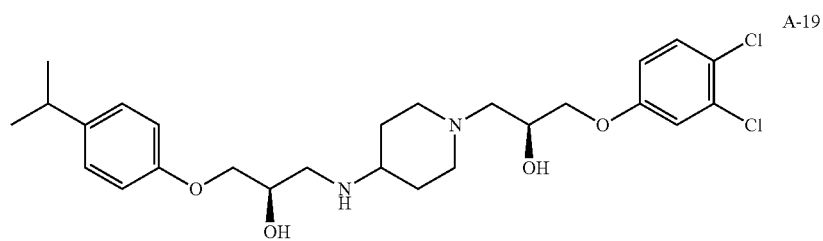
A-19
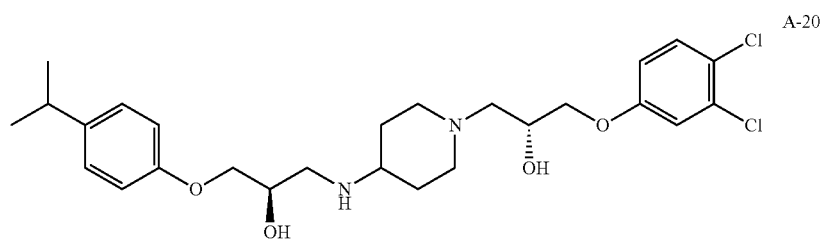
A-20
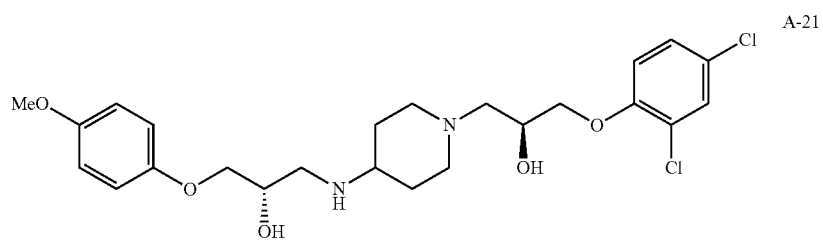
A-21
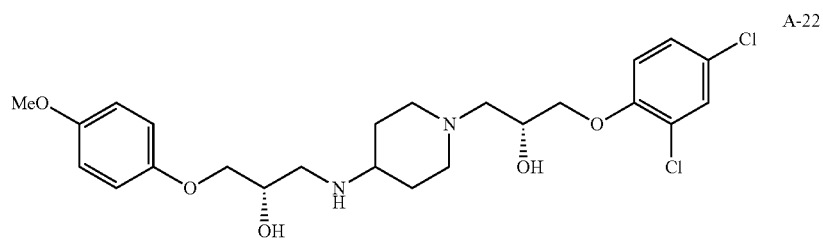
A-22
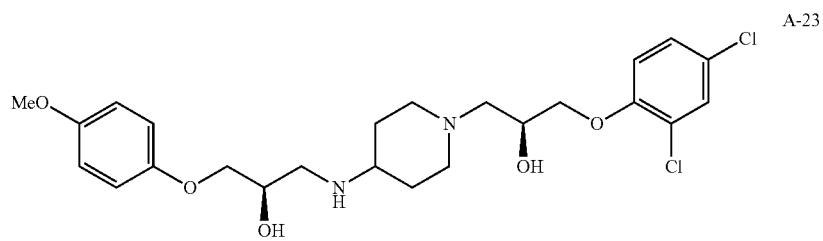
A-23

-continued
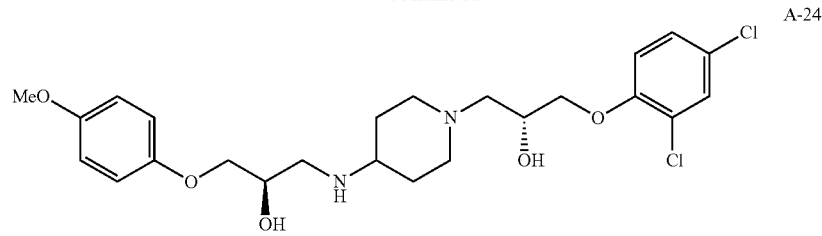
A-24
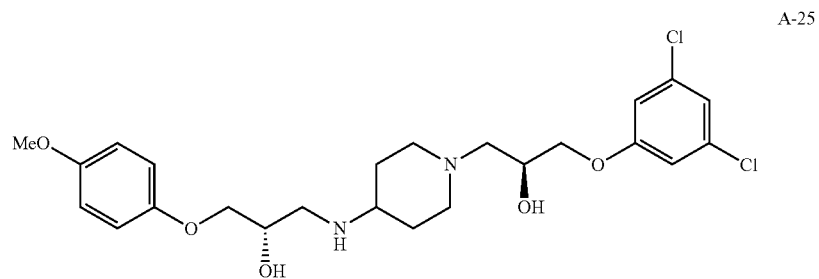
A-25
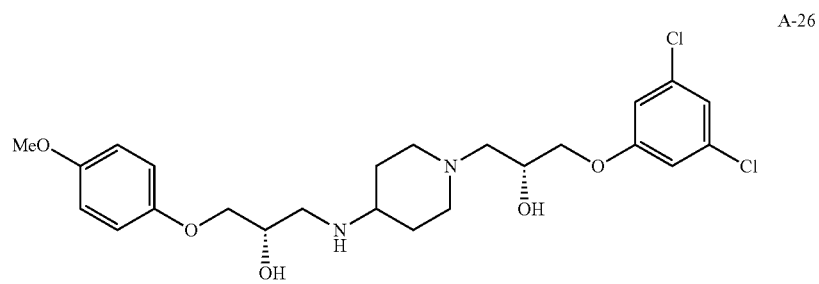
A-26
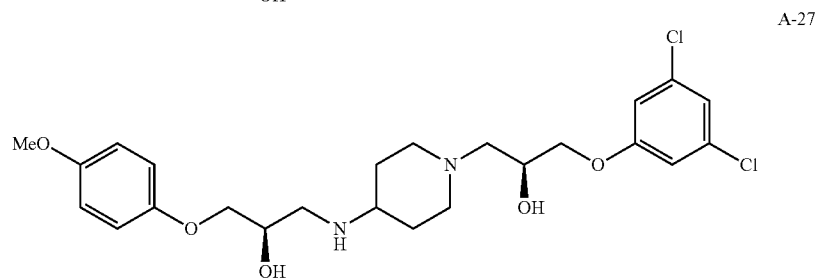
A-27
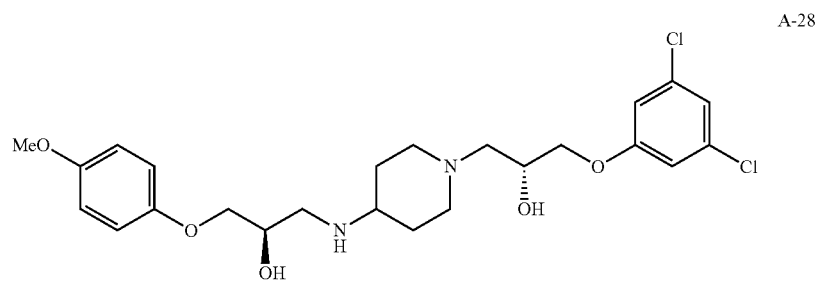 [SMILES: COc1cccc(OC[C@H](O)CNC2CCN(C[C@@H](O)COc3cc(Cl)cc(Cl)c3)CC2)c1]
A-28
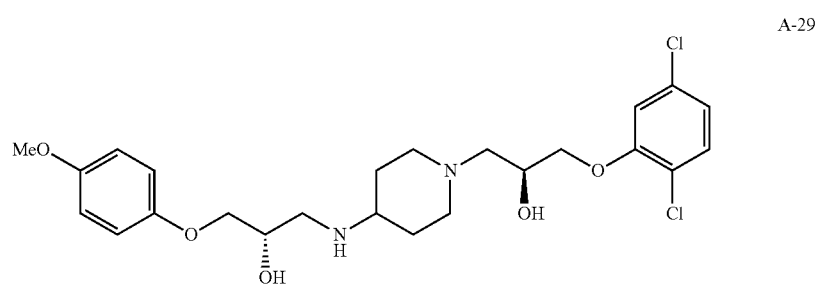
A-29

-continued
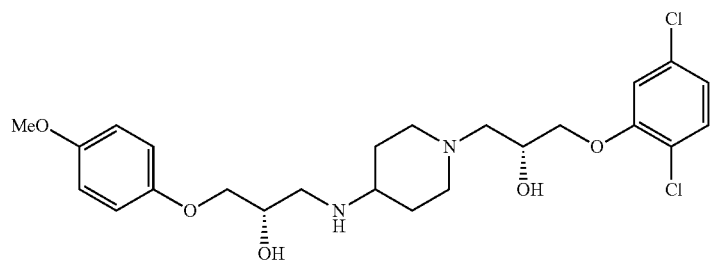
A-30
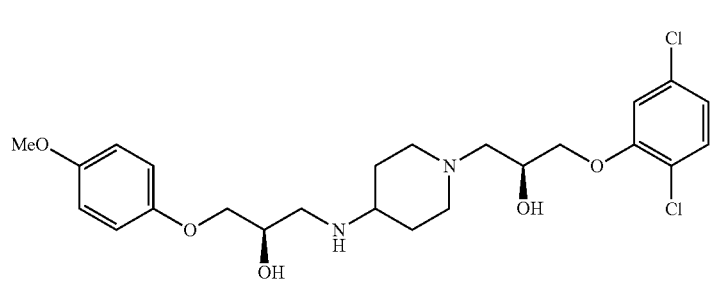
A-31
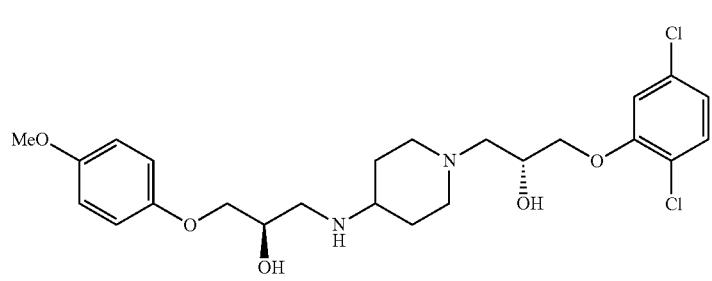
A-32
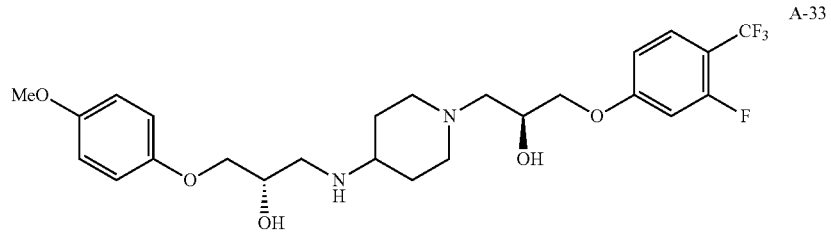
A-33
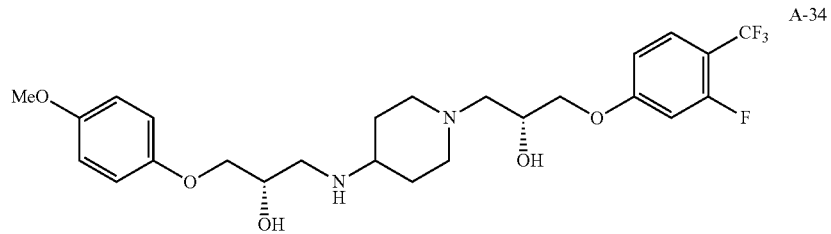
A-34
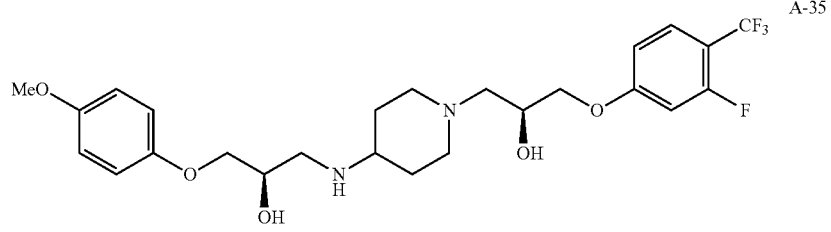
A-35

-continued
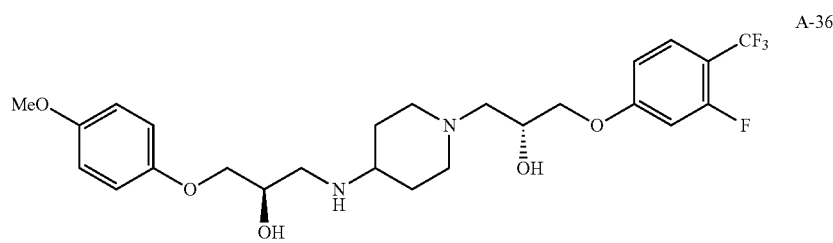
A-36
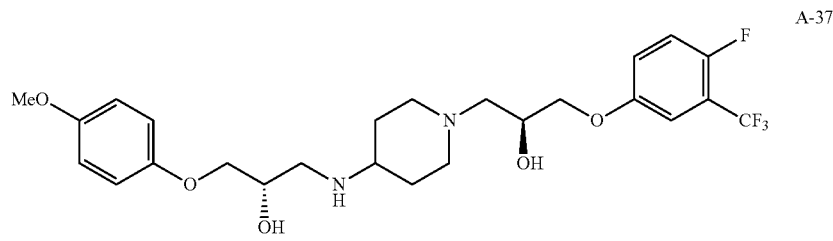
A-37
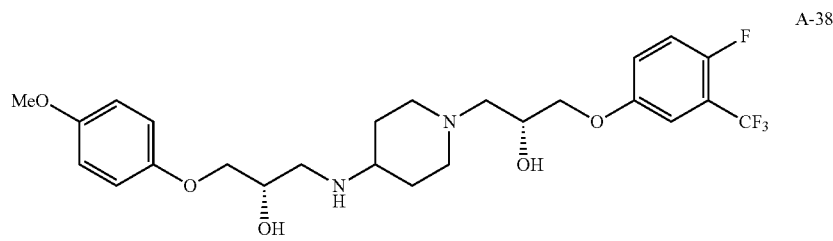
A-38
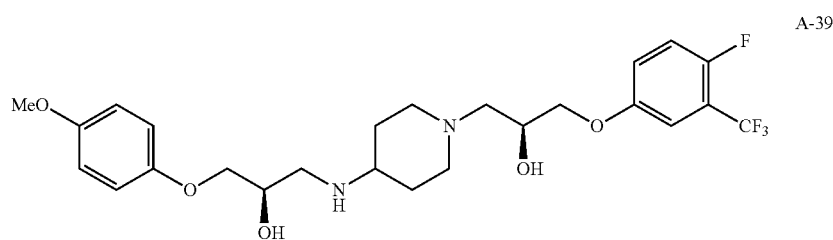
A-39
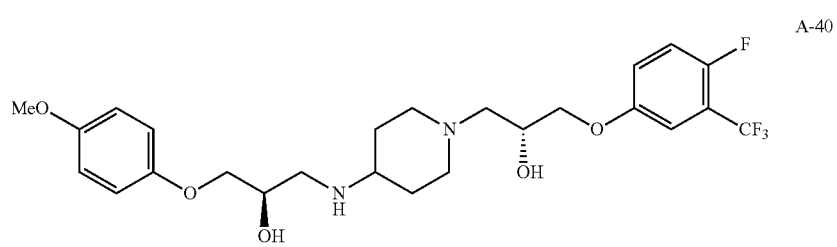
A-40
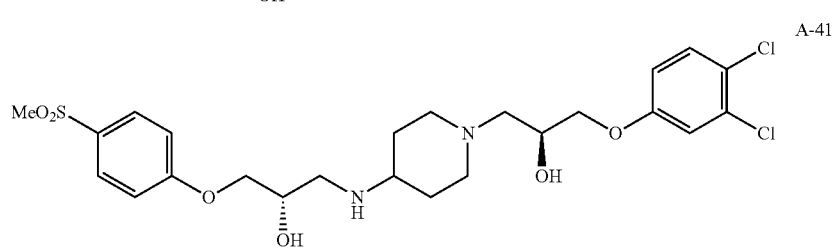
A-41
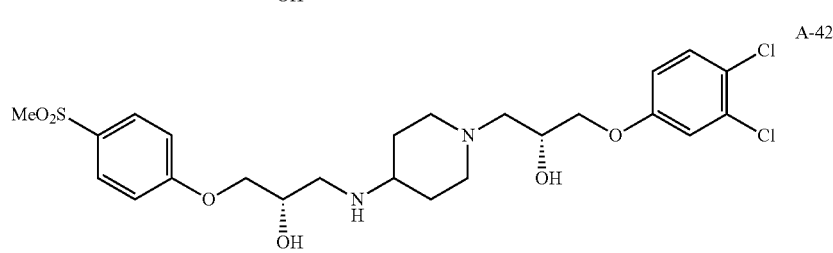
A-42

-continued
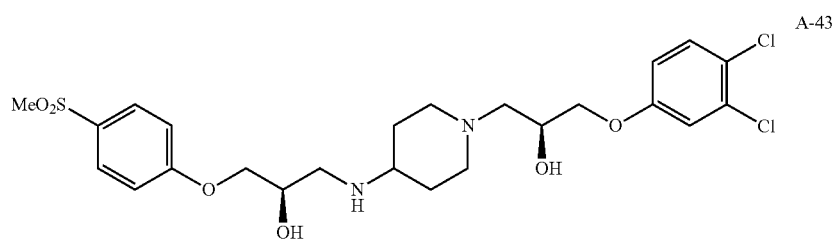
A-43
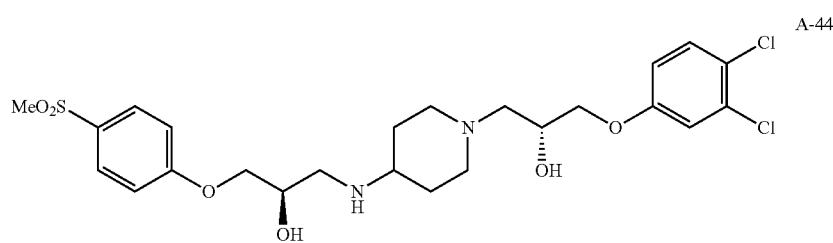
A-44
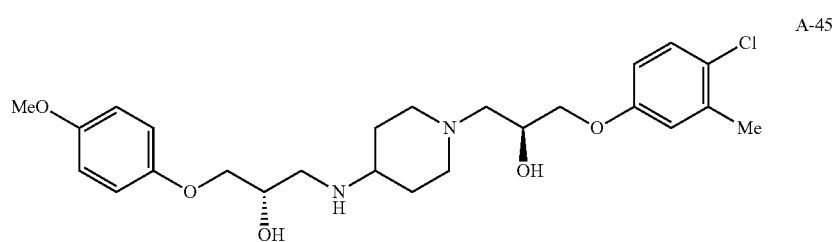
A-45
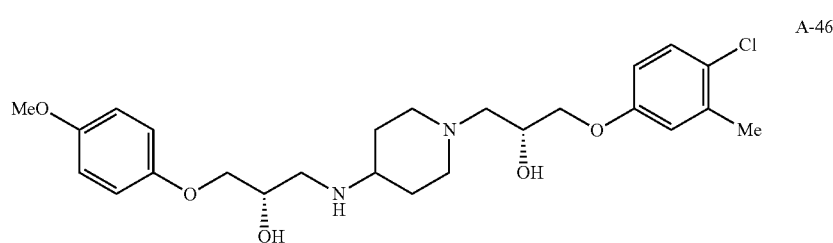
A-46
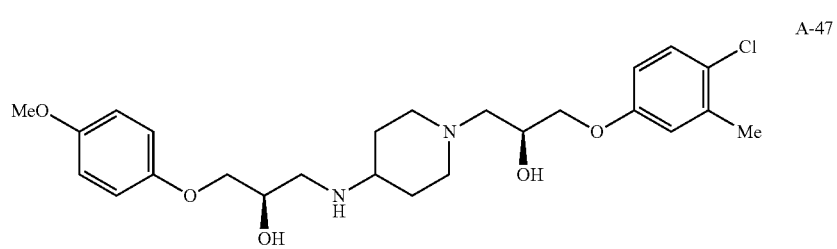
A-47
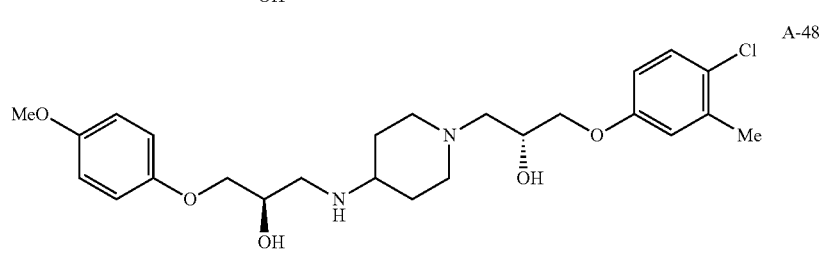
A-48
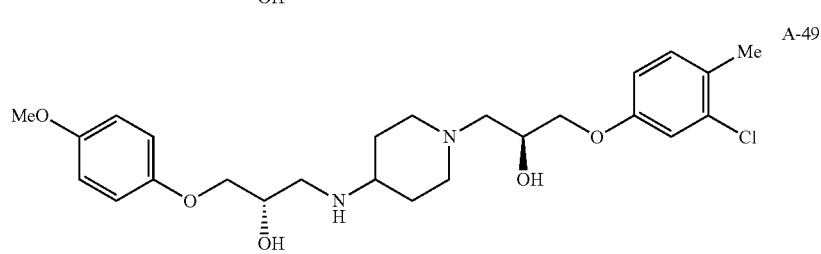
A-49

-continued
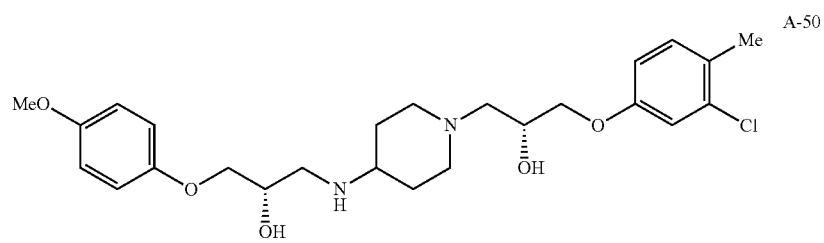
A-50
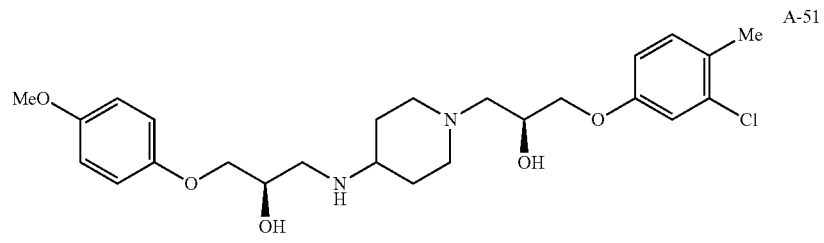
A-51
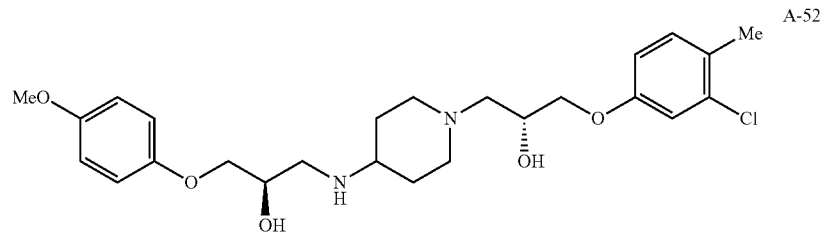
A-52
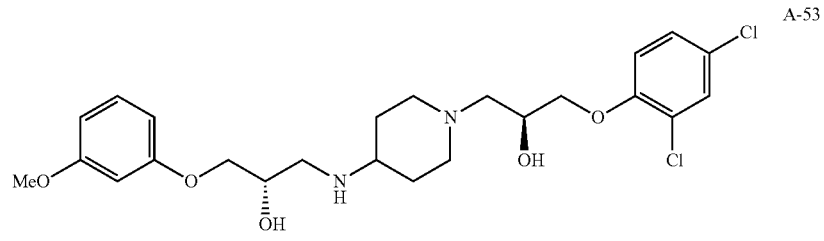
A-53
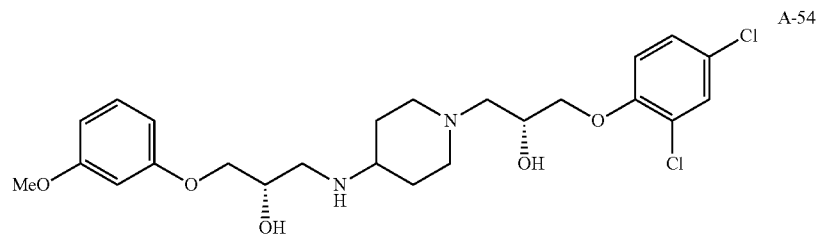
A-54
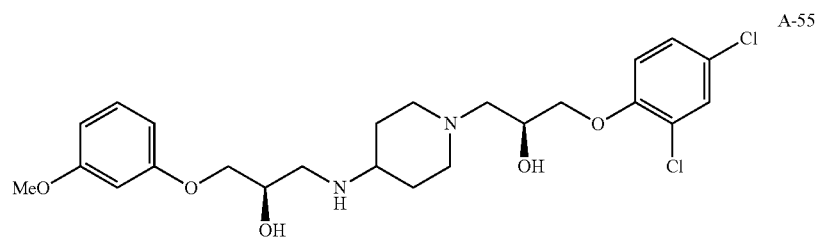
A-55
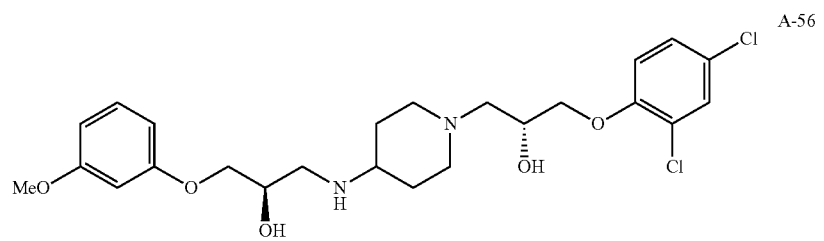
A-56

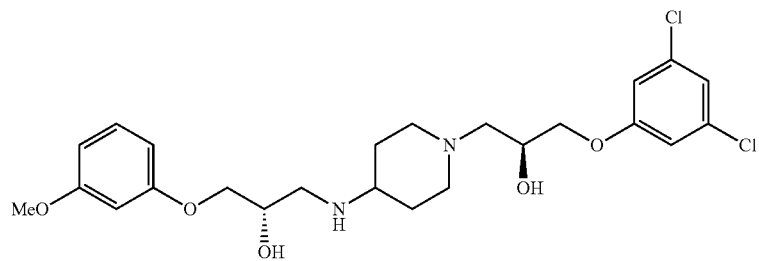

A-57

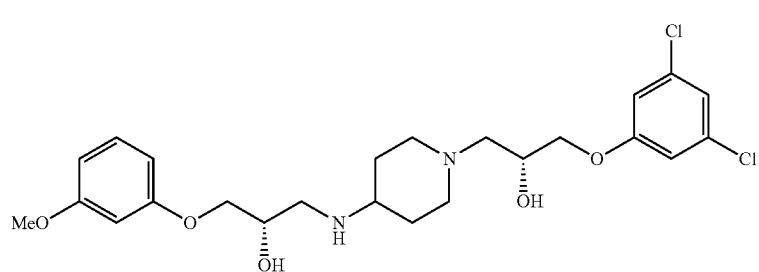

A-58

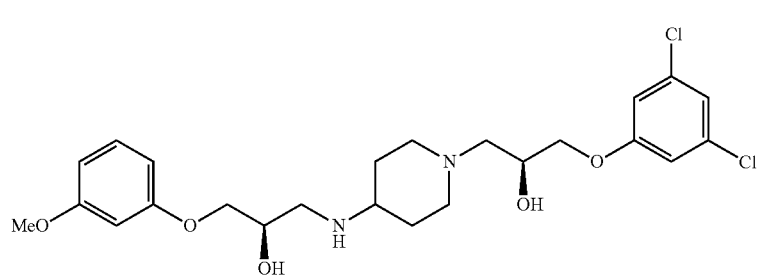

A-59

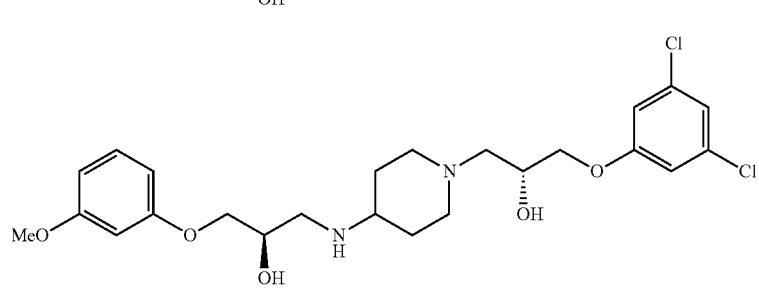

A-60

In various embodiments, compounds designated A-1 through A-60 can be synthesized using synthetic methods known to skilled artisans.

In some embodiments, a composition comprising a cell adhesion antagonist of the present teachings can further comprise a linker. In various configurations, a linker can be used to connect two or more antagonists of the present teachings. In some aspects, a linker can also, or alternatively, be used to attach one or more cell adhesion antagonists disclosed herein to a support molecule or material, as described below. In various configurations, a linker can be a moiety that does not contain a CAR sequence and that can be covalently linked to at least two peptide sequences. In various configurations, a linker can be, for example and without limitation, an amino acid, a peptide and/or a non-peptide sequence, for example $(H_2N(CH_2)_nCO_2H)_m$ wherein n is an integer from 1 to 10 and m is an integer from 1 to 4000 such as glycine ($H_2NCH_2CO_2H$, i.e., n=1 and m=1), aminopropanoic acid, aminobutanoic acid, aminopentanoic acid, amino hexanoic acid, 2,3-diaminopropanoic acid, lysine, ornithine, or a multimer thereof. In various aspects, a peptide or a non-peptide linker can be incorporated or attached to a cell adhesion antagonist of the present teachings using any method known in the art. In various embodiments, a linker can extend between multiple compounds of the present teachings, and peptide or protein sequences can be joined head-to-tail (i.e., the linker can be covalently attached to the carboxyl or amino group of each peptide sequence), head-to-side chain and/or tail-to-side chain. In some configurations, an antagonist comprising one or more linkers can form linear or branched structures.

In some embodiments, the present teachings encompass structures comprising two, three, four, or more compounds of the present teachings linked together. In some configurations, the compounds can be adjacent to one another (i.e., without intervening sequences). In some configurations, the compounds can be linked by a peptide linker. In some configurations, the compounds can be linked by a non-peptide linker.

In various embodiments, the present teachings include methods of inhibiting cell adhesion in a subject. In various configurations, these aspects can comprise administering to a subject in need thereof a therapeutically effective amount of a composition of the present teachings. In some configurations, a method of inhibiting cell adhesion in a subject can comprise contacting a classical cadherin-expressing cell with a composition of the present teachings. In some configurations, the administering to a subject can comprise transdermal administration. In some configurations, the subject can be a mammal, such as a human, a farm animal, or a companion animal.

In various embodiments, administration of a cell adhesion antagonist of the present teachings can be used in the treatment of various diseases and disorders. In various embodiments, administration of an antagonist of the present teachings to a mammal can be used, for example and without limitation, to reduce unwanted or excessive cell adhesion, to inhibit cancer development, to decrease the size of a tumor, to inhibit angiogenesis, to modulate adipogenesis, to inhibit fibrosis, to increase vasopermeability, to modulate the immune system, to modulate stem cell and/or progenitor cell differentiation, to inhibit neurite outgrowth, to prevent intimal thickening by inhibiting smooth muscle cell migration, and/or to stimulate an immune response to tumors. For example, diseases that are subject to treatment with a cell adhesion antagonist of the present teachings include, without limitation, cancer, arthritis, diabetes, obesity, restenosis and fibrosis.

In various embodiments, a method for inhibiting cell adhesion can comprise contacting cells that express one or more cadherins (such as, for example, E-cadherin or N-cadherin) with a cell adhesion antagonist of the present teachings. In various configurations, a cadherin-expressing cell can be, for example and without limitation, an epithelial cell, an endothelial cell, a neural cell, a tumor cell, a stem cell, a progenitor cell, a mural cell, a stromal cell or a lymphocyte. The contacting can include contacting a cell with a therapeutically effective amount of a cell adhesion antagonist of the present teachings.

In some embodiments, the present teachings include methods of inducing apoptosis in a CAD-expressing cell. In various configurations, these methods comprise contacting a CAD-expressing cell with a cell adhesion antagonist of the present teachings in a pharmacologically effective amount for inhibiting CAD-mediated cell adhesion.

In some embodiments, the present teachings include methods of reducing the progression of a cancer in a mammal. The cancer can be any type of cancer, such as, for example and without limitation, pancreatic cancer, prostate cancer, multiple myeloma, chronic myelogenous leukemia, melanoma, or neuroblastoma. In various configurations, these methods comprise administering to a mammal having a cancer, a cell adhesion antagonist of the present teachings. In some configurations, a method for inhibiting cancer metastasis can comprise administrating to a mammal having a cancer a cell adhesion antagonist of the present teachings in a therapeutically effective amount.

In various embodiments, the present teachings include methods of modulating tumor permeability barriers to a drug, such as, for example and without limitation, a chemotherapeutic agent. In various configurations, these methods can comprise contacting a CAD-expressing cell with a cell adhesion antagonist of the present teachings. In some configurations, a method of modulating a tumor permeability barrier to a drug such as a chemotherapeutic agent, can comprise administering to a mammal a therapeutically effective amount of a cell adhesion antagonist of the present teachings. In some configurations, a method of modulating tumor permeability barriers to cytotoxic T cells can comprise contacting a CAD-expressing stromal cell with a cell adhesion antagonist of the present teachings. In some configurations, a method of modulating tumor permeability barriers to cytotoxic T cells can comprise administering to a mammal a cell adhesion antagonist of the present teachings in an effective amount.

In various embodiments, the present teachings include methods of modulating adipogenesis (a process dependent on angiogenesis). In various configurations, these methods can comprise contacting a CAD-expressing cell with a cell adhesion antagonist of the present teachings. In some configurations, a method of modulating adipogenesis can comprise administering to a mammal a therapeutically effective amount of a cell adhesion antagonist of the present teachings.

In various embodiments, the present teachings include methods of stimulating blood vessel regression. In various configurations, these methods can comprise administering to a mammal a cell adhesion antagonist of the present teachings in an amount effective for inhibiting CAD mediated cell adhesion. In some configurations, methods for the treatment of disease conditions that are dependent on angiogenesis and neovascularization can comprise contacting an N-cadherin-expressing cell with a cell adhesion antagonist of the present teachings. In some configurations, methods for the treatment of disease conditions that are dependent on angiogenesis and neovascularization can comprise administering to a mammal a cell adhesion antagonist of the present teachings.

In various embodiments, the present teachings include methods of modulating the immune system of a mammal. In various configurations, these methods can comprise administering to a mammal a pharmacologically effective amount of a cell adhesion antagonist of the present teachings.

In various embodiments, the present teachings include methods of modulating cell adhesion, proliferation, migration and/or survival, of vascular smooth muscle cells (VSMC) or pericytes. In various configurations, these methods can comprise contacting a CAD-expressing VSMC or pericyte with, or administering to a mammal, a cell adhesion antagonist of the present teachings.

In various embodiments, the present teachings include methods of regulating the overgrowth and/or migration of VSMCs or pericytes. In various configurations, these methods can comprise contacting CAD expressing cells such as VSMCs or pericytes with an antagonist of CAD-mediated cell adhesion of the present teachings. In some configurations, methods for regulating the overgrowth and/or migration of VSMCs or pericytes in a mammal can comprise administering to a mammal an antagonist of CAD-mediated cell adhesion of the present teachings. In some configurations, these methods can be used to prevent the formation or advance of restenosis, vein bypass graft failure, allograft vasculopathy, dialysis graft failure, thin cap fibroatheroma, and other vessel stenoses. In some configurations, administration of a cell adhesion antagonist of the present teachings can be used to treat essential and secondary hypertension, atheroma, arteriosclerosis, or other indications in which endothelial injury or trauma has occurred. In some configurations, methods of maintaining vessel luminal area following vascular trauma can comprise contacting a CAD expressing cell with a cell adhesion antagonist of the present teachings. In some configurations, methods of maintaining vessel luminal area following vascular trauma can comprise administering to a mammal a pharmacologically effective amount of cell adhesion antagonist of the present teachings. In some configurations, methods for treating a traumatized vessel can comprise contacting a CAD expressing cell with cell adhesion antagonist of the present teachings in a pharmaceutically effective amount. In some configurations, methods of treating a traumatized vessel can comprise administering to a mammal cell adhesion antagonist of the present teachings in a pharmaceutically effective amount. In some embodiments, these methods can be used to treat a trauma injury, such as, for example and without limitation, damage that occurs during stent placement, organ transplant, vein bypass, angioplasty, or dialysis graft placement.

In some embodiments, the present teachings include methods of treating lung fibrosis in a mammal. In various configurations, these methods can comprise administering to a mammal a cell adhesion antagonist in an amount effective for inhibiting the development of lung fibrosis. In some embodiments, the present teachings include methods of enhancing the delivery of a pharmaceutically active substance through the skin of a mammal. In various configurations, these methods can comprise contacting epithelial cells of a mammal with a pharmaceutically active substance and a cell adhesion antagonist of the present teachings. In various configurations, the contacting can be performed under conditions and for a time sufficient to promote passage of the substance across the epithelial cells. In some configurations, methods for enhancing the delivery of a pharmaceutically active substance to a tumor in a mammal can comprise contacting the tumor with pharmaceutically effective amounts of a pharmaceutically active substance and a cell adhesion antagonist of the present teachings. The contacting can be performed under conditions and for a time sufficient to promote passage of the substance into the cells of the tumor.

In some embodiments, the present teachings include methods of enhancing delivery of nanoparticles to a tumor in a mammal. In various configurations, these methods can comprise contacting the tumor with nanoparticles and a pharmaceutically effective amount of a cell adhesion antagonist of the present teachings. The contacting can be performed under conditions and for a time sufficient to promote passage of the nanoparticle into the cells of the tumor.

In some embodiments, the present teachings include methods of enhancing the delivery of a pharmaceutically active substance to the central nervous system of a mammal. In various configurations, these methods can comprise administering to a mammal a pharmaceutically effective amount of a cell adhesion antagonist of the present teachings.

In some embodiments, the present teachings include methods of enhancing inhaled compound delivery in a mammal. In various configurations, these methods can comprise contacting lung epithelial cells of a mammal with a cell adhesion antagonist of the present teachings. In various configurations, these methods can comprise contacting lung epithelial cells of a mammal with a cell adhesion antagonist of the present teachings, along with a pharmaceutically active substance.

In some embodiments, one or more cell adhesion antagonists of the present teachings can be an active component of a medical device. In some configurations, the medical device can be, for example and without limitation, a balloon, a stent, a shunt, a catheter, a stent graft, a vascular graft, a vascular patch, a filter, an adventitial wrap, an intraluminal paving system, a cerebral stent, a cerebral aneurysm filter coil, a myocardial plug, a pacemaker lead, a dialysis access graft or a heart valve. In some configurations, a cell adhesion antagonist of the present teachings can be linked to, coated on, and/or dispersed within essentially any medical device to allow delivery of the antagonist to cells or tissue.

In some embodiments, a cell adhesion antagonist of the present teachings can be delivered to a CAD expressing cell, or a subject, by any delivery approach suitable to a given indication and compatible with the delivery of the cell adhesion antagonist. In some configurations, administration of a cell adhesion antagonist of the present teachings can be via a catheter. In some configurations, administration of a cell adhesion antagonist of the present teachings can be via an infusion needle.

In some embodiments, the present teachings include a patch comprising a matrix and a cell adhesion antagonist disclosed herein. In some configurations, a patch can further include at least one additional pharmaceutical agent, such as, for example and without limitation, a chemotherapeutic for cancer treatment. In various embodiments, a patch of the present teachings can be a transdermal patch which can be used to administer a cell adhesion antagonist to a subject in need thereof by transdermal absorption. In some embodiments, a patch of the present teachings can be used to administer a pharmaceutical substance to a subject in need thereof whereby the presence of an antagonist of the present teachings promotes transdermal absorption of the pharmaceutical agent. In some embodiments, a patch of the present teachings can be used to enhance skin permeability. In some embodiments, a patch of the present teachings can be used in conjunction with a separately administered pharmaceutical agent to enhance transdermal absorption of the agent in a subject in need thereof, whereby the presence of a cell adhesion antagonist promotes transdermal absorption.

In various configurations, a cell adhesion antagonist of the present teachings, administered via a patch or through another administration route, with or without an additional pharmaceutical agent, can be used, for example and without limitation, to modulate angiogenesis, neovascularization, immune system function, cell adhesion, cell proliferation, cell migration, and/or cell survival.

In various configurations, a cell adhesion antagonist of the present teachings can be used to modulate a tumor barrier to cytotoxic T cells.

In some embodiments, the present teachings include kits comprising components which can be used for enhancing transdermal delivery of a pharmaceutically active substance. In various configurations, a kit can comprise a skin patch and a cell adhesion antagonist of the present teachings.

In various embodiments, an effective amount of a cell adhesion antagonist of the present teachings can be administered under conditions and for times effective for treatment. Determining the effective amount, the appropriate conditions and the sufficient time period can either be within the ordinary skill in the art, and/or accomplished in view of the teachings provided herein.

In some embodiments, the present teachings include compounds, prodrugs thereof and pharmaceutically acceptable salts thereof of structure

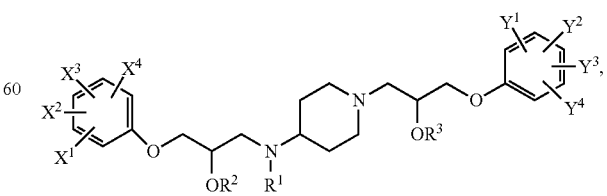

wherein: $R^1$ can be selected from the group consisting of H, $C_1$-$C_6$ alkyl, —C(=O)$C_1$-$C_6$ alkyl, and —C(=O)O$C_1$-$C_6$ alkyl; $R^2$ and $R^3$ can be each independently selected from the group consisting of H, $C_1$-$C_6$ alkyl, —C(=O)$C_1$-$C_6$ alkyl and —C(=O)O$C_1$-$C_6$ alkyl; and $X^1$, $X^2$, $X^3$, $X^4$, $Y^1$, $Y^2$, $Y^3$ and $Y^4$ can be each independently selected from the group consisting of H, OH, halo, cyano, nitro, azido, $C_1$-$C_6$-alkyl; $C_1$-$C_6$-alkoxy; —C(=O)$C_1$-$C_6$ alkyl, $CF_3$, $OCF_3$, $CCl_3$, $SO_2C_1$-$C_6$ alkyl, $SO_2N(R^1)C_1$-$C_6$ alkyl, $N(R^1)SO_2C_1$-$C_6$ alkyl, $P(O)(C_1$-$C_6$ alkyl)$_2$, $NR^2R^3$, COOH, C(=O)O$C_1$-$C_6$ alkyl, C(=O)N($R^1$)$C_1$-$C_6$ alkyl, N($R^1$)C(=O)$C_1$-$C_6$ alkyl, N($R^1$)C(=O)N(R)$C_1$-$C_6$ alkyl and N($R^1$)C(=O)O$C_1$-$C_6$ alkyl, provided that the compound is not 1-(3,4-difluorophenoxy)-3-(1-(3-(3,4-difluorophenoxy)-2-hydroxypropyl)piperidin-4-ylamino)propan-2-ol, 1-(3,4-dichlorophenoxy)-3-(4-(2-hydroxy-3-(4-methoxyphenoxy)propylamino)piperidin-1-yl)propan-2-ol or (R)-1-(3,4-dichlorophenoxy)-3-(4-((R)-2-hydroxy-3-(4-methoxyphenoxy)propylamino)piperidin-1-yl)propan-2-ol.

In some embodiments, a compound or pharmaceutically acceptable salt thereof in accordance with the present teachings can be 1-(4-chlorophenoxy)-3-(1-(3-(4-chlorophenoxy)-2-hydroxypropyl)piperidin-4-ylamino)propan-2-ol (2)

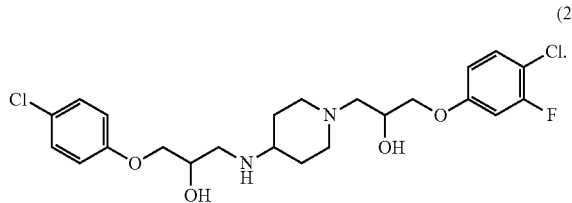

In various embodiments, a compound or pharmaceutically acceptable salt thereof in accordance with the present teachings can be 1-(1-(2-hydroxy-3-phenoxypropyl)piperidin-4-ylamino)-3-phenoxypropan-2-ol (4)

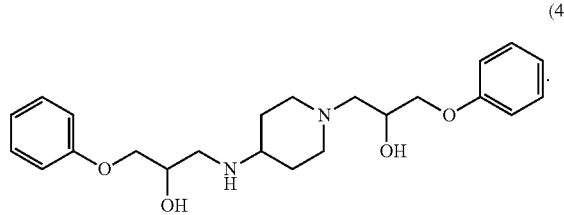

In various embodiments, a compound or pharmaceutically acceptable salt thereof in accordance with the present teachings can be 1-(4-chlorophenoxy)-3-(4-(2-hydroxy-3-phenoxypropylamino)piperidin-1-yl)propan-2-ol (5)

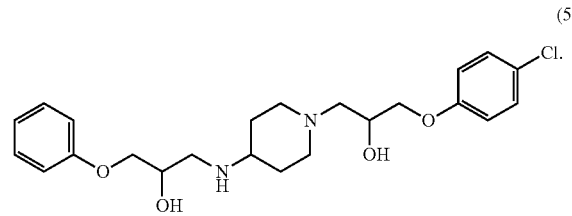

In various embodiments, a compound or pharmaceutically acceptable salt thereof in accordance the present teachings can be 1-(4-chlorophenoxy)-3-(1-(2-hydroxy-3-phenoxypropyl)piperidin-4-ylamino)propan-2-ol (6)

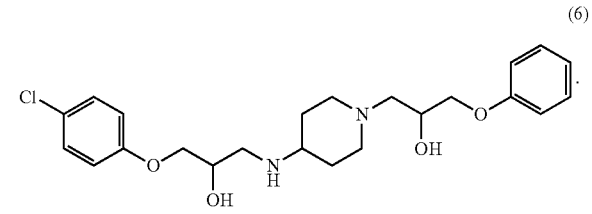 [SMILES: OC(CNC1CCN(CC(O)COc2ccccc2)CC1)COc1ccc(Cl)cc1]

In various embodiments, a compound or pharmaceutically acceptable salt thereof in accordance with the present teachings can be 1-(4-((2-hydroxy-3-phenoxypropyl)(methyl)amino)piperidin-1-yl)-3-phenoxypropan-2-ol (7)

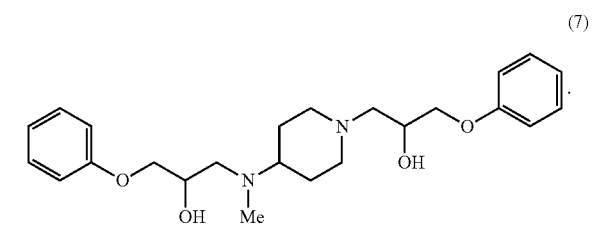 [SMILES: CN(CC(O)COc1ccccc1)C1CCN(CC(O)COc2ccccc2)CC1]

In various embodiments, a compound or pharmaceutically acceptable salt thereof in accordance with the present teachings can be (S)-1-(3,4-dichlorophenoxy)-3-(1-((S)-3-(3,4-dichlorophenoxy)-2-hydroxypropyl)piperidin-4-ylamino)propan-2-ol (10)

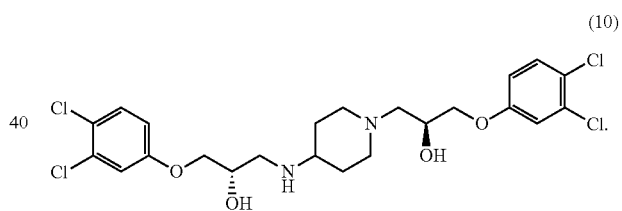

In various embodiments, a compound or pharmaceutically acceptable salt thereof in accordance with the present teachings can be (R)-1-(3,4-dichlorophenoxy)-3-(1-((R)-3-(3,4-dichlorophenoxy)-2-hydroxypropyl)piperidin-4-ylamino)propan-2-ol (13)

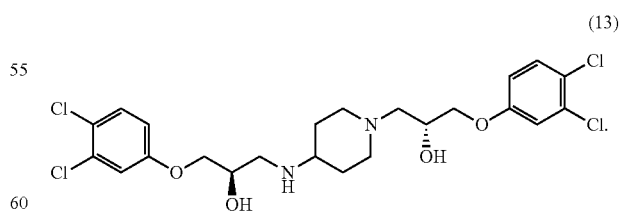

In various embodiments, a compound or pharmaceutically acceptable salt thereof in accordance with the present teachings can be (S)-1-(3,4-dichlorophenoxy)-3-(4-(((S)-2-hydroxy-3-(4-methoxyphenoxy)propyl)amino)piperidin-1-yl)propan-2-ol

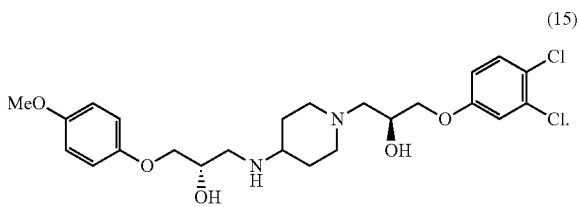 [SMILES: COc1ccc(OC[C@@H](O)CNC2CCN(C[C@H](O)COc3ccc(Cl)c(Cl)c3)CC2)cc1]

In various embodiments, a compound or pharmaceutically acceptable salt thereof in accordance with the present teachings can be (R)-1-(3,4-dichlorophenoxy)-3-(4-(((S)-2-hydroxy-3-(4-methoxyphenoxy)propyl)amino)piperidin-1-yl)propan-2-ol

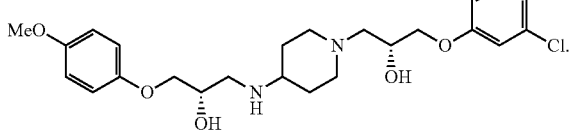

In various embodiments, a compound or pharmaceutically acceptable salt thereof in accordance with the present teachings can be (S)-1-(3,4-dichlorophenoxy)-3-(4-((R)-2-hydroxy-3-(4-methoxyphenoxy)propylamino)piperidin-1-yl)propan-2-ol

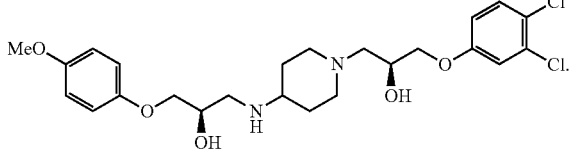

In various embodiments, the present teachings include methods of synthesis of disclosed compounds. In various configurations, a method of synthesizing 1-(4-chlorophenoxy)-3-(1-(3-(4-chlorophenoxy)-2-hydroxypropyl)piperidin-4-ylamino)propan-2-ol

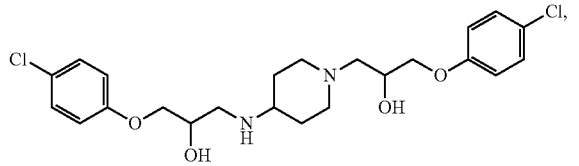

can comprise contacting 2-((4-chlorophenoxy)methyl)oxirane

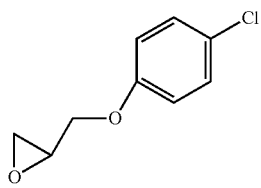 [SMILES: Clc1ccc(OCC2CO2)cc1]

with piperidin-4-amine

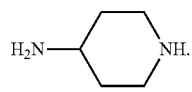

In various embodiments, a method of synthesizing 1-(1-(2-hydroxy-3-phenoxypropyl)piperidin-4-ylamino)-3-phenoxypropan-2-ol

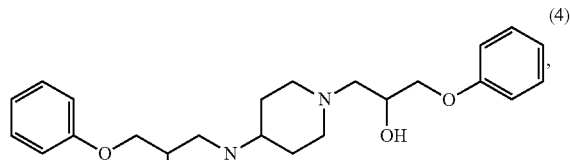

can comprise contacting 2-(phenoxymethyl)oxirane

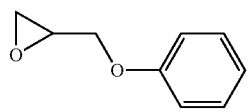 [SMILES: c1ccc(OCC2CO2)cc1]

with piperidin-4-amine

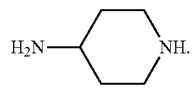

In various embodiments, a method of synthesizing 1-(4-chlorophenoxy)-3-(4-(2-hydroxy-3-phenoxypropylamino)piperidin-1-yl)propan-2-ol

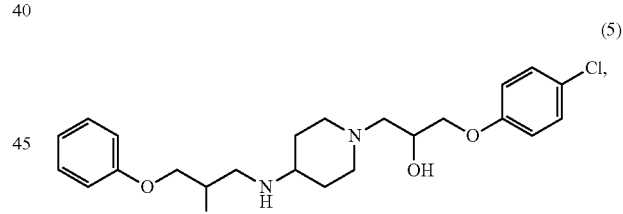

can comprise contacting 1-(4-aminopiperidin-1-yl)-3-(4-chlorophenoxy)propan-2-ol

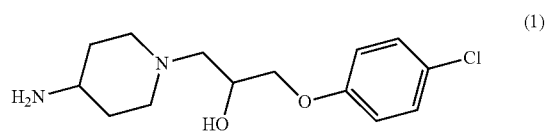 [SMILES: NC1CCN(CC(O)COc2ccc(Cl)cc2)CC1]

with 2-(phenoxymethyl)oxirane

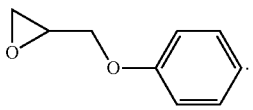 [SMILES: c1ccc(OCC2CO2)cc1]

In various embodiments, a method of synthesizing 1-(4-chlorophenoxy)-3-(1-(2-hydroxy-3-phenoxypropyl)piperidin-4-ylamino)propan-2-ol

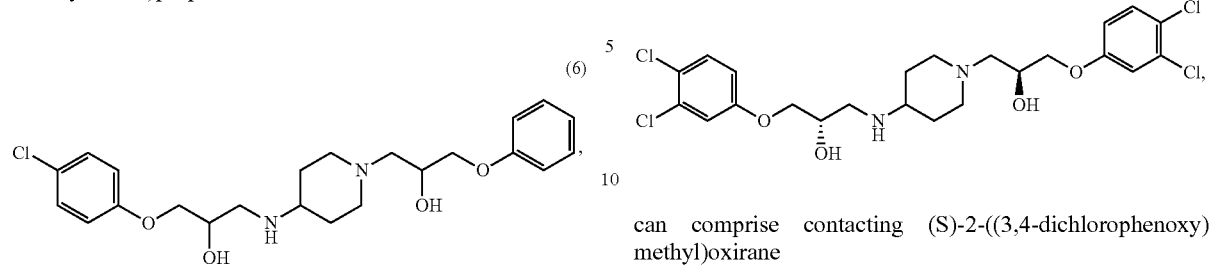

can comprise contacting 1-(4-aminopiperidin-1-yl)-3-phenoxypropan-2-ol (3)

with 2-((4-chlorophenoxy)methyl)oxirane

In various embodiments, a method of synthesizing 1-(4-((2-hydroxy-3-phenoxypropyl)(methyl)amino)piperidin-1-yl)-3-phenoxypropan-2-ol

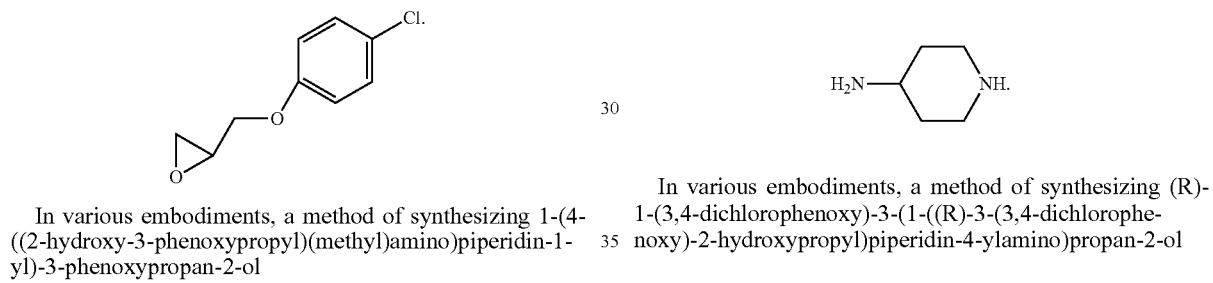

can comprise:
forming a reaction mixture comprising 1-(1-(2-hydroxy-3-phenoxypropyl)piperidin-4-ylamino)-3-phenoxypropan-2-ol (4)

and formaldehyde; and contacting the mixture with sodium triacetoxyborohydride.

In various embodiments, a method of synthesizing (S)-1-(3,4-dichlorophenoxy)-3-(1-((S)-3-(3,4-dichlorophenoxy)-2-hydroxypropyl)piperidin-4-ylamino)propan-2-ol (10)

can comprise contacting (S)-2-((3,4-dichlorophenoxy)methyl)oxirane (8)

with piperidin-4-amine

In various embodiments, a method of synthesizing (R)-1-(3,4-dichlorophenoxy)-3-(1-((R)-3-(3,4-dichlorophenoxy)-2-hydroxypropyl)piperidin-4-ylamino)propan-2-ol

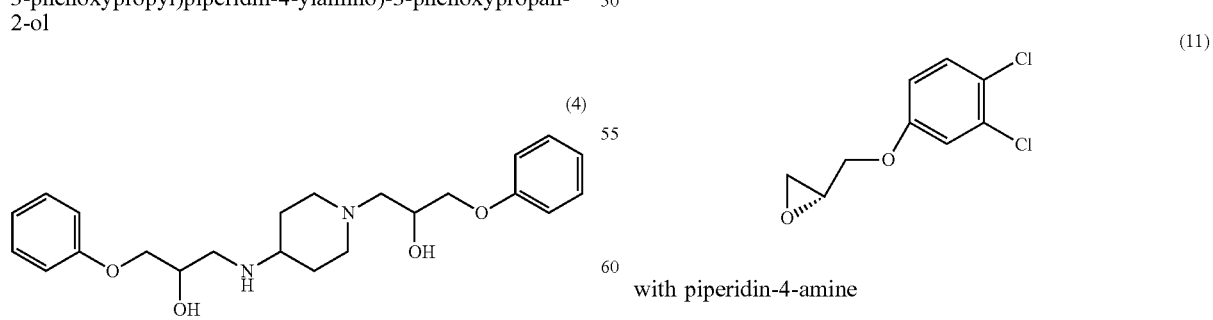

can comprise contacting (R)-2-((3,4-dichlorophenoxy)methyl)oxirane (11)

with piperidin-4-amine

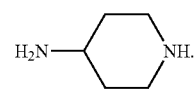

In various embodiments, a method of synthesizing (S)-1-(3,4-dichlorophenoxy)-3-(4-(((S)-2-hydroxy-3-(4-methoxyphenoxy)propyl)amino)piperidin-1-yl)propan-2-ol

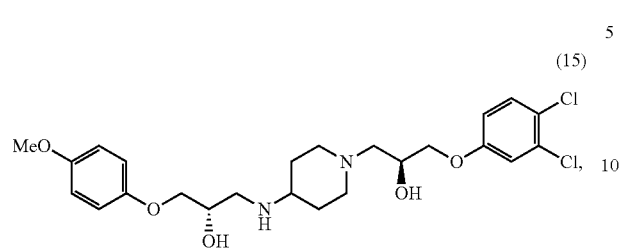
(15)

can comprise contacting (S)-1-(4-aminopiperidin-1-yl)-3-(3,4-dichlorophenoxy)propan-2-ol

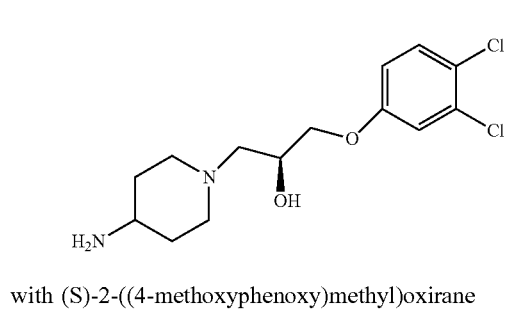
(9)

with (S)-2-((4-methoxyphenoxy)methyl)oxirane

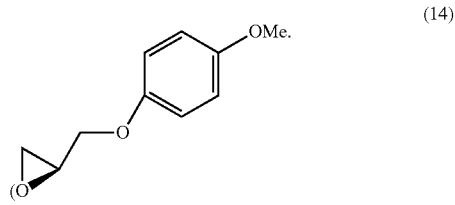
(14)

In various embodiments, a method of synthesizing (S)-1-(3,4-dichlorophenoxy)-3-(4-((R)-2-hydroxy-3-(4-methoxyphenoxy)propylamino)piperidin-1-yl)propan-2-ol

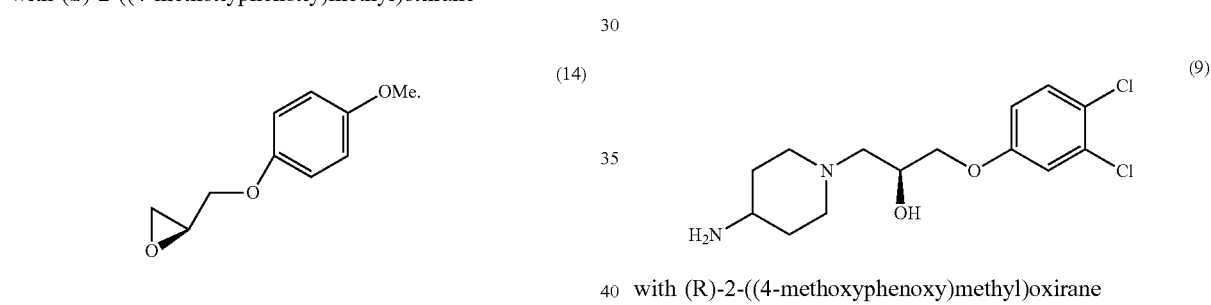
(18)

can comprise contacting (S)-1-(4-aminopiperidin-1-yl)-3-(3,4-dichlorophenoxy)propan-2-ol (9)

with (R)-2-((4-methoxyphenoxy)methyl)oxirane (17)

In various embodiments, a method of synthesizing (R)-1-(3,4-dichlorophenoxy)-3-(4-(((S)-2-hydroxy-3-(4-methoxyphenoxy)propyl)amino)piperidin-1-yl)propan-2-ol (16)

can comprise contacting (2R)-3-(4-amino-1-piperidyl)-1-(3,4-dichlorophenoxy)-2-propanol)

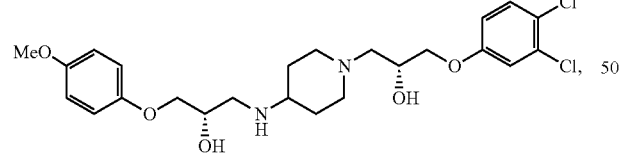
(12)

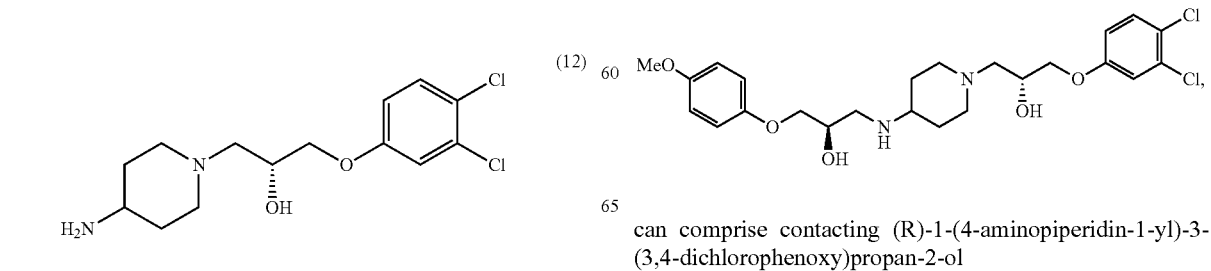
(19)

can comprise contacting (R)-1-(4-aminopiperidin-1-yl)-3-(3,4-dichlorophenoxy)propan-2-ol

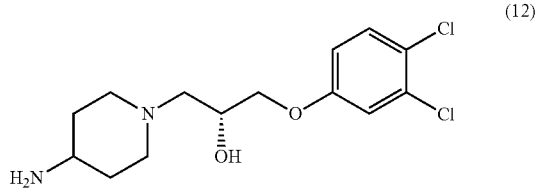 [SMILES: NC1CCN(C[C@@H](O)COc2ccc(Cl)c(Cl)c2)CC1]

with (R)-2-((4-methoxyphenoxy)methyl)oxirane

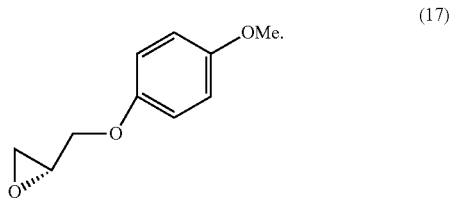 [SMILES: COc1ccc(OC[C@H]2CO2)cc1]

In various embodiments, the present teachings include compositions comprising a compound or a pharmaceutically acceptable salt thereof as disclosed herein, and a pharmaceutically acceptable carrier, excipient or diluent. In some configurations, the composition can further comprise a heterologous compound. In some configurations, the heterologous compound can be a pharmaceutically active compound. In various configurations, the heterologous compound can be a detectable marker. In various configurations, the composition can further comprise a solid support. In some configurations, the solid support can be a polymeric matrix. In various configurations, the solid support can be selected from the group consisting of a plastic dish, a plastic tube, a suture, a membrane, an ultrathin film, a bioreactor, a nanoparticle and a microparticle.

In various embodiments, the present teachings include a patch for transdermal delivery. A patch of the present teachings can comprise a cell adhesion antagonist described herein, and a matrix. In some configurations, a patch for transdermal delivery can further comprise at least one additional pharmaceutical agent.

In various embodiments, the present teachings include methods of inhibiting cell adhesion in a subject. In various configurations, these methods can comprise administering to a subject in need thereof a therapeutically effective amount of a composition disclosed herein. In various configurations, the administering to the subject can comprise transdermal administration. In various configurations, the subject can be a mammal. In some configurations, the mammal can be a human. In various configurations, the mammal can be a farm animal. In various configurations, the mammal can be a companion animal.

In various embodiments, the present teachings include methods of inhibiting cell adhesion. In various configurations, these methods can comprise contacting a classical cadherin-expressing cell with a composition in accordance with the present teachings.

In various embodiments, the present teachings include methods of inhibiting cancer development in a subject in need thereof. In various configurations, these methods can comprise administering to the subject a therapeutically effective amount of a composition disclosed herein. In various configurations, the cancer can be pancreatic cancer. In various configurations, the cancer can be multiple myeloma. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of decreasing the size of a tumor in a subject in need thereof. In various configurations, these methods can comprise administering to the subject a therapeutically effective amount of a composition in accordance with the present teachings. In some configurations, the tumor can be a pancreatic cancer tumor. In various configurations, the tumor can be a multiple myeloma tumor. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of inhibiting angiogenesis in a subject in need thereof. In various configurations, these methods an comprise administering to the subject a therapeutically effective amount of a composition disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of increasing vasopermeability in a subject in need thereof. In various configurations, the methods can comprise administering to the subject a therapeutically effective amount of a composition as disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of inhibiting neurite outgrowth in a subject in need thereof. In various configurations, these methods can comprise administering to the subject a therapeutically effective amount of a composition disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of enhancing apoptosis in a subject in need thereof. In various configurations these methods can comprise administering to the subject a therapeutically effective amount of a composition disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of modulating the immune system in a subject in need thereof. In various configurations, these methods can comprise administering to the subject a therapeutically effective amount of a composition in accordance with the present teachings. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of modulating stem cell and progenitor cell differentiation in a subject in need thereof. In various configurations, these methods can comprise administering to the subject a therapeutically effective amount of a composition disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of inhibiting vascular smooth muscle cell migration in a subject in need thereof. In various configurations, these methods can comprise administering to the subject in need thereof a therapeutically effective amount of a composition disclosed herein. In some configurations, the amount administered can be an amount sufficient to prevent intimal thickening. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of stimulating an immune response to a tumor in a subject in need thereof. In various configurations, these methods can comprise administering to the subject a therapeutically effective amount of a composition in accordance with the present teachings. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of inhibiting fibrosis, including growth or adhesion of a fibrosis tumor, in a subject in need thereof. In some configurations, these methods can comprise administering to the subject a therapeutically effective amount of a composition as disclosed herein. In various configurations, the administering to the subject can comprise transdermal administration.

In various configurations, the subject can be a mammal. In some configurations, the mammal can be a human. In some configurations, the mammal can be a farm animal. In some configurations, the mammal can be a companion animal.

In various embodiments, the present teachings include a method of inhibiting cell adhesion comprising contacting a classical cadherin-expressing cell with a composition as disclosed herein, wherein the classical cadherin-expressing cell can express a classical cadherin selected from the group consisting of E-cadherin, N-cadherin, P-cadherin, R-cadherin and a combination thereof.

In various embodiments, the present teachings methods of inhibiting cell adhesion. In various configurations, these methods can comprise contacting a classical cadherin-expressing cell with a composition as disclosed herein, wherein the classical cadherin-expressing cell can express E-cadherin.

In various embodiments, the present teachings methods of inhibiting cell adhesion. In various configurations, these methods can comprise contacting a classical cadherin-expressing cell with a composition as disclosed herein, wherein the classical cadherin-expressing cell can express N-cadherin.

In various configurations, a compound of the present teachings can be for use in the treatment of a disease such as, without limitation, a cancer, arthritis, diabetes, obesity, restenosis or fibrosis. In some configurations, the cancer can be selected from the group consisting of pancreatic cancer, prostate cancer, multiple myeloma, chronic myelogenous leukemia, melanoma and neuroblastoma. In some configurations, the cancer can be pancreatic cancer. In some configurations, the cancer can be multiple myeloma. In some configurations, the arthritis can be rheumatoid arthritis.

In various embodiments, the present teachings include methods of treating pancreatic cancer. In some configurations, these methods can comprise administering to a subject in need thereof a composition as disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of treating a cancer such as multiple myeloma. In various configurations, these methods can comprise administering to a subject in need thereof an N-cadherin antagonist as disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal. In some configurations, administration of an N-cadherin antagonist of the present teachings, such as, without limitation, an N-cadherin antagonist of structure

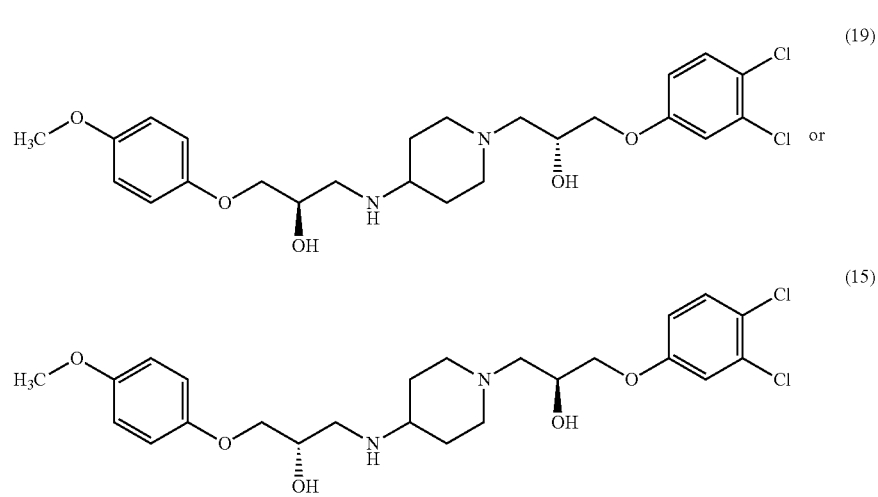

can reduce multiple myeloma (MM) cell viability. In some configurations, administration of an N-cadherin antagonist of the present teachings can decrease multiple myeloma tumor burden.

In various embodiments, the present teachings include methods of treating rheumatoid arthritis. In various configurations, these methods can comprise administering to a subject in need thereof a composition as disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include methods of preventing ovulation. In various configurations, these methods can comprise administering to a subject in need thereof a composition as disclosed herein. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include compositions and methods for birth control. In some configurations, these methods include administering to a subject in need thereof a composition as disclosed. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include compositions and methods for preventing ovulation. In some configurations, these methods include administering to a subject in need thereof a composition as disclosed. In various configurations, the administering to the subject can comprise transdermal administration. In various configurations, the subject can be a mammal. In some configurations, the mammal can be a human. In some configurations, the mammal can be a farm animal. In some configurations, the mammal can be a companion animal.

In various embodiments, the present teachings include a patch for transdermal delivery. A patch of these embodiments can comprise a matrix, and a cell adhesion antagonist disclosed in the present teachings, such as, without limitation, a cell adhesion antagonist of structure

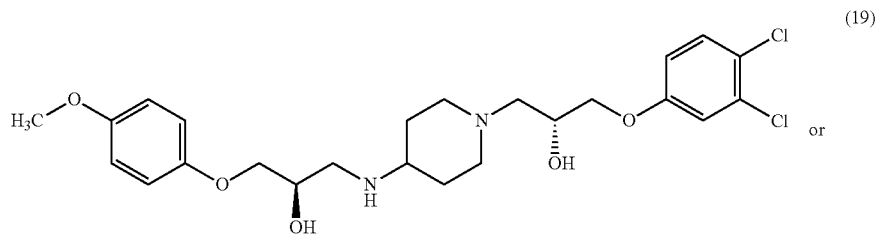

(19)

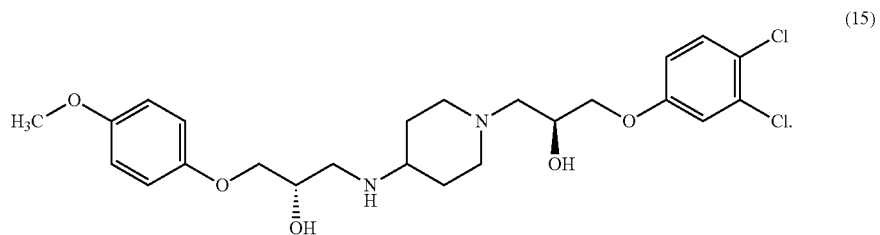

(15)

In some configurations, a patch of the present teachings can further comprise at least one additional pharmaceutical agent.

In various embodiments, the present teachings include methods of inhibiting cell adhesion in a subject. In various configurations, these methods can comprise administering to a subject in need thereof a therapeutically effective amount of a cell adhesion antagonist of structure

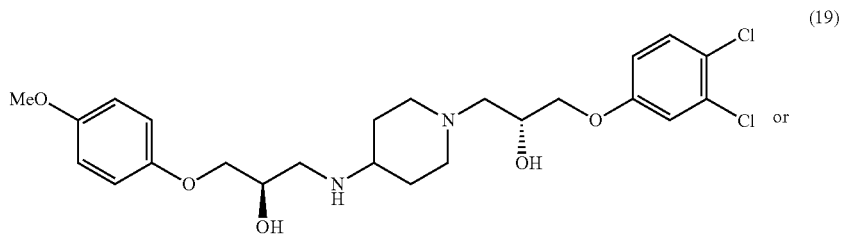

(19)

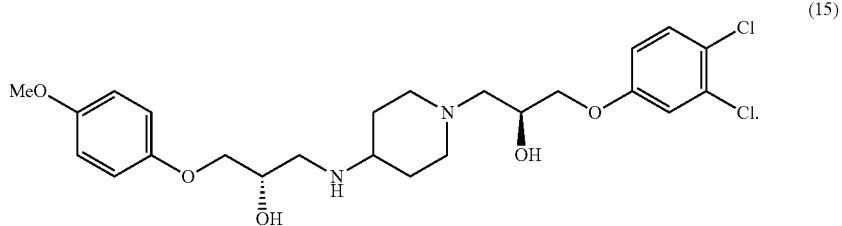

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of inhibiting cell adhesion. In various configurations, these methods can comprise contacting a classical cadherin-expressing cell with a cell adhesion antagonist of structure

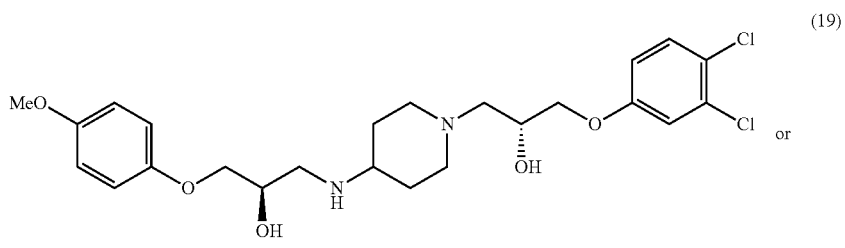

(19) or

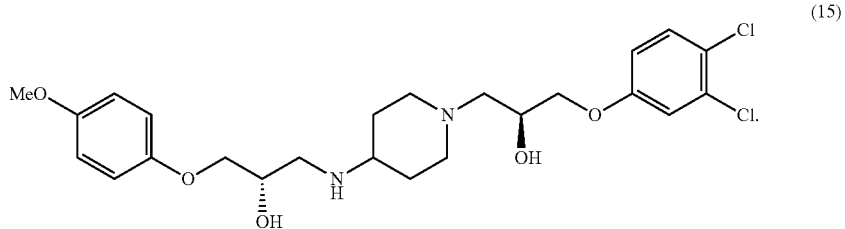

(15)

In various embodiments, the present teachings include methods of inhibiting cancer development in a subject in need thereof. In various configurations, these methods can comprise administering to the subject a therapeutically effective amount of a cell adhesion antagonist of structure

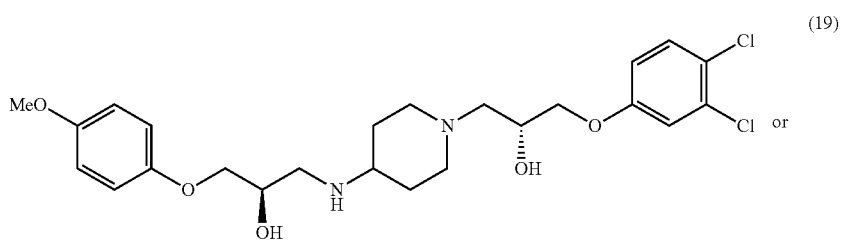

(19) or

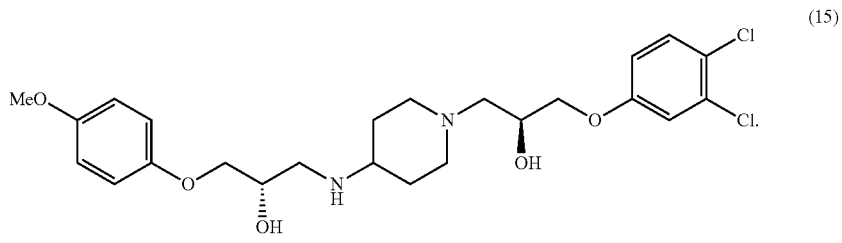

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of decreasing the size of a tumor in a subject in need thereof. In various configurations, these methods include administering to the subject a therapeutically effective amount of a cell adhesion antagonist of structure

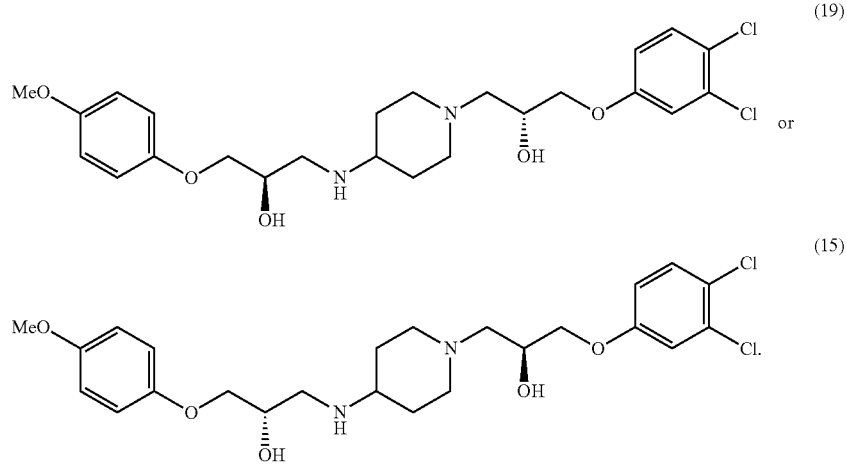

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of inhibiting angiogenesis in a subject in need thereof. In various configurations, these methods can comprise administering to the subject a therapeutically effective amount of a cell adhesion antagonist of structure

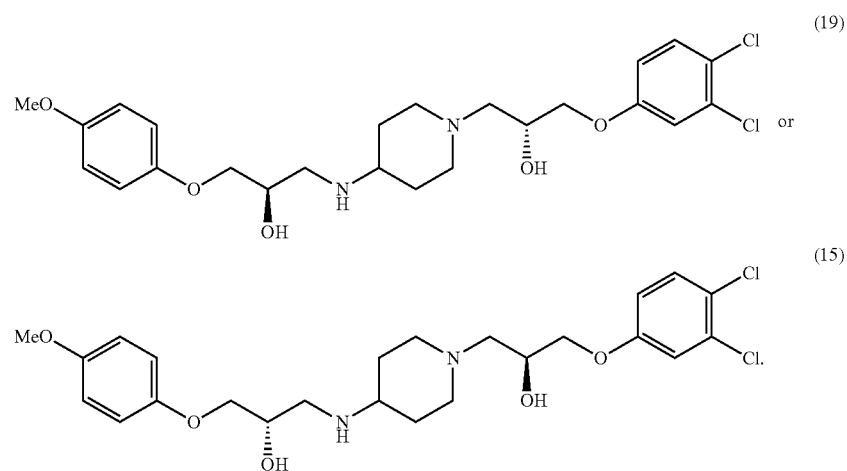

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of increasing vasopermeability in a subject in need thereof. In some configurations, these methods can comprise administering to the subject a therapeutically effective amount of a cell adhesion antagonist of structure

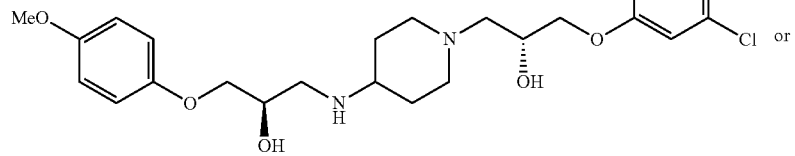

(19)

or

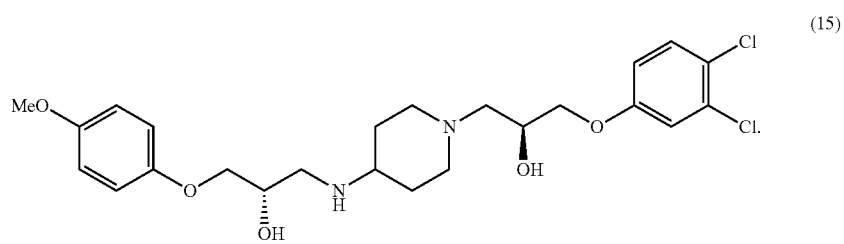

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of inhibiting neurite outgrowth in a subject in need thereof. In various configurations, these methods can include administering to the subject a therapeutically effective amount of a cell adhesion antagonist of structure

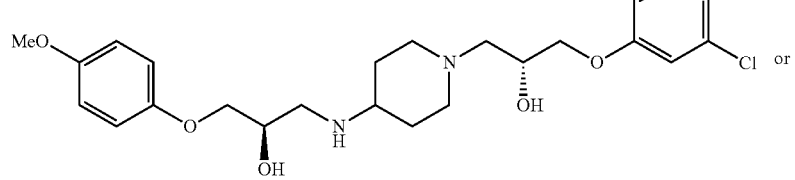

(19)

or

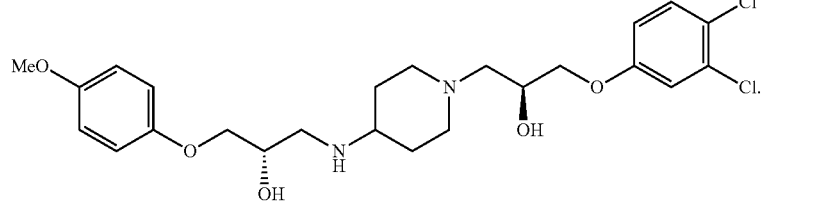

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of enhancing apoptosis in a subject in need thereof. In various configurations, the methods can comprise comprising administering to the subject a therapeutically effective amount of a cell adhesion antagonist of structure

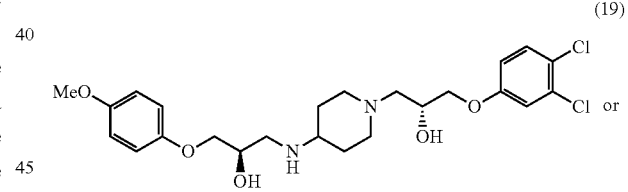

(19) or

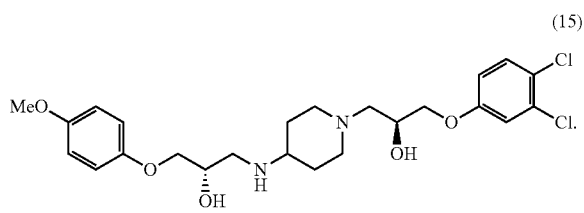

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of modulating the immune system in a subject in need thereof, comprising administering to the subject a therapeutically effective amount of a cell adhesion antagonist of structure

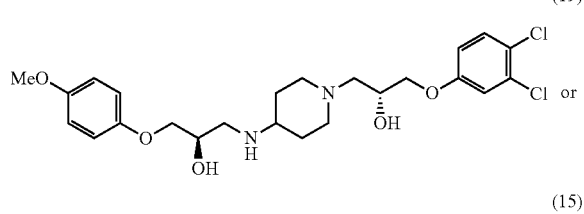

(19)

or

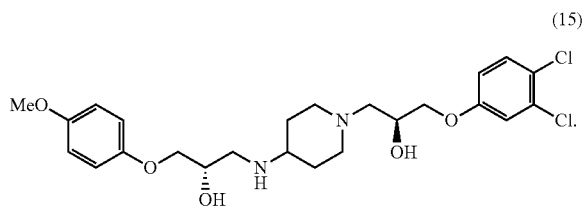 [SMILES: COc1ccc(OC[C@@H](O)CNC2CCN(C[C@H](O)COc3ccc(Cl)c(Cl)c3)CC2)cc1]

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of modulating stem cell and progenitor cell differentiation in a subject in need thereof, comprising administering to the subject a therapeutically effective amount of a cell adhesion antagonist of structure

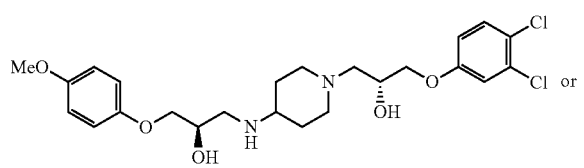

(19)

or

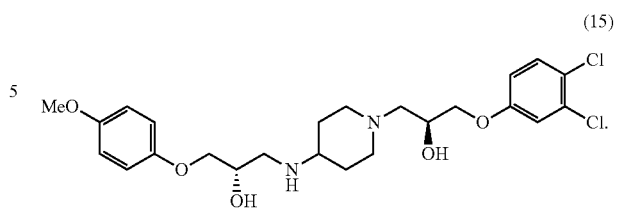

(15)

In some configurations, the subject can be a mammal. In some configurations, the mammal can be a human. In some configurations, the mammal can be a farm animal. In some configurations, the mammal can be a companion animal.

In various embodiments, the present teachings include methods of inhibiting vascular smooth muscle cell migration in a subject in need thereof. In various configurations, these methods can comprise administering to the subject a therapeutically effective amount of a cell adhesion antagonist of structure

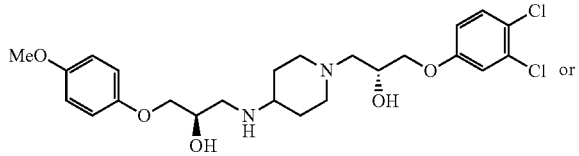

(19)

or

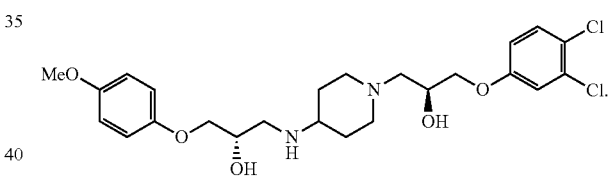

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of stimulating an immune response to a tumor in a subject in need thereof. In various configurations, these methods can comprise administering to the subject a therapeutically effective amount of a cell adhesion antagonist of structure

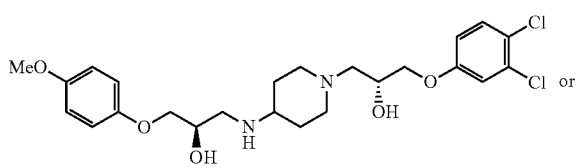

(19)

or

-continued

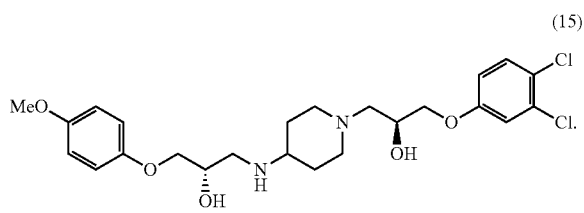

(15)

In various configurations, the administering to a subject can comprise transdermal administration. In some configurations, the subject can be a mammal. In some configurations, the mammal can be a human. In some configurations, the mammal can be a farm animal. In some configurations, the mammal can be a companion animal.

In various embodiments, the present teachings include methods of inhibiting fibrosis tumor in a subject in need thereof, comprising administering to the subject a therapeutically effective amount of a cell adhesion antagonist of structure

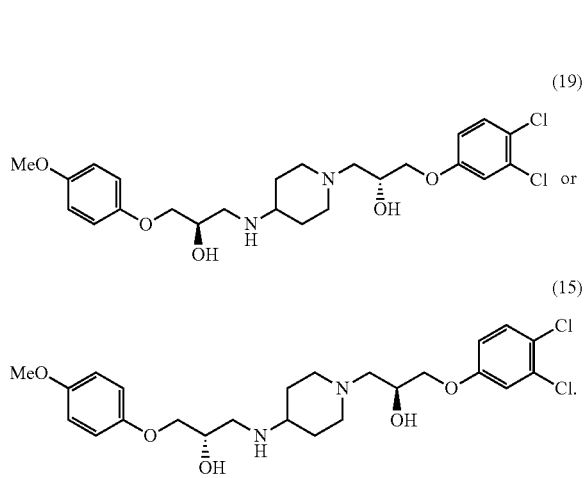

In various configurations, the administering to a subject can comprise transdermal administration. In some configurations, the subject can be a mammal. In some configurations, the mammal can be a human. In various configurations, the mammal can be a farm animal. In various configurations, the mammal can be a companion animal.

In various embodiments, the present teachings include methods of inhibiting cell adhesion. In various configurations, the methods can comprise contacting a classical cadherin-expressing cell with a cell adhesion antagonist of structure

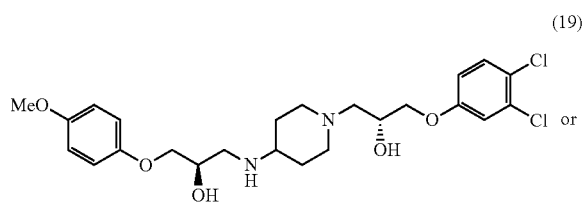

-continued

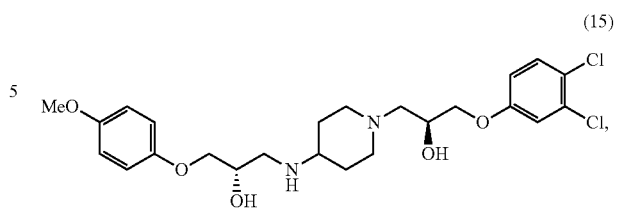

(15)

wherein the classical cadherin-expressing cell expresses a classical cadherin selected from the group consisting of E-cadherin, N-cadherin, P-cadherin, R-cadherin and a combination thereof. In various configurations, the classical cadherin-expressing cell expresses E-cadherin. In various configurations, the classical cadherin-expressing cell expresses N-cadherin.

In various embodiments, the present teachings include a compound of structure

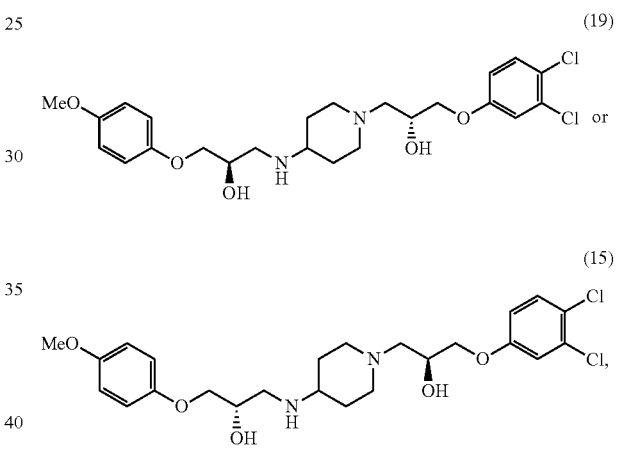

for use in the treatment of a disease selected from the group consisting of a cancer, arthritis, diabetes, obesity, restenosis and fibrosis. In some configurations, the cancer can be selected from the group consisting of pancreatic cancer, prostate cancer, multiple myeloma, chronic myelogenous leukemia, melanoma and neuroblastoma. In various configurations, the arthritis can be rheumatoid arthritis.

In various embodiments, the present teachings include methods of decreasing viability of a cancer-associated fibroblast. In various configurations, these methods can comprise contacting an N-cadherin antagonist of the present teachings, such as a compound of structure

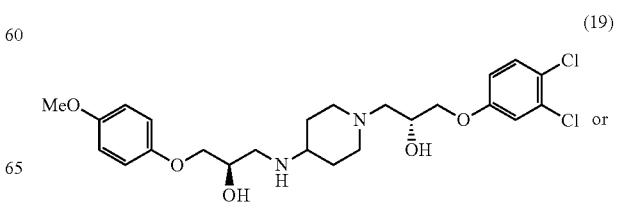

-continued (15)

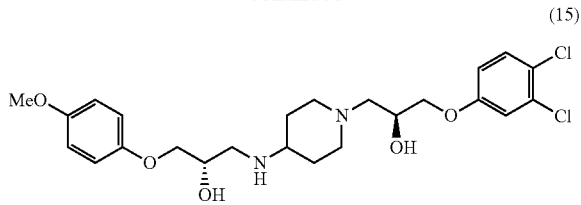

with a cancer-associated fibroblast. The contacting can be in vitro or in vivo.

In various embodiments, the present teachings include using an N-cadherin antagonist disclosed herein, such as, for example (15)

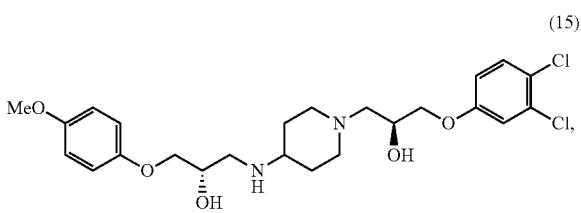

to treat rheumatoid arthritis (RA) and other chronic inflammatory joint diseases. Without being limited by theory, it is believed that human fibroblast-like synoviocytes (FLS) are a target for treating RA, and that FLS cell adhesion is mediated by cadherin 11 and N-cadherin (Agarwal, S. K., et al., *Arthritis & Rheumatism* 58, 1044-1054, 2018). In various configurations, an N-cadherin antagonist of the present teachings can be applied topically, orally, or systemically to disrupt synoviocyte adhesion and thereby treat rheumatoid arthritis (RA) and other chronic inflammatory joint diseases.

In various embodiments, the present teachings include administration of a cadherin antagonist disclosed herein, such as, for example (15)

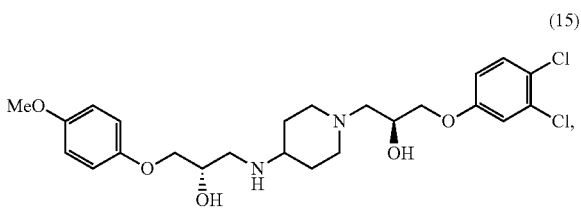 [SMILES: COc1ccc(OC[C@@H](O)CNC2CCN(C[C@H](O)COc3ccc(Cl)c(Cl)c3)CC2)cc1]

in methods of inhibiting corpus luteum formation. A cadherin antagonist of the present teachings can thus be used as a contraceptive.

BRIEF DESCRIPTION OF THE DRAWINGS

FIG. 2A-D illustrate molecular structures of cell adhesion antagonists of the present teachings.

DETAILED DESCRIPTION

Figure 1:
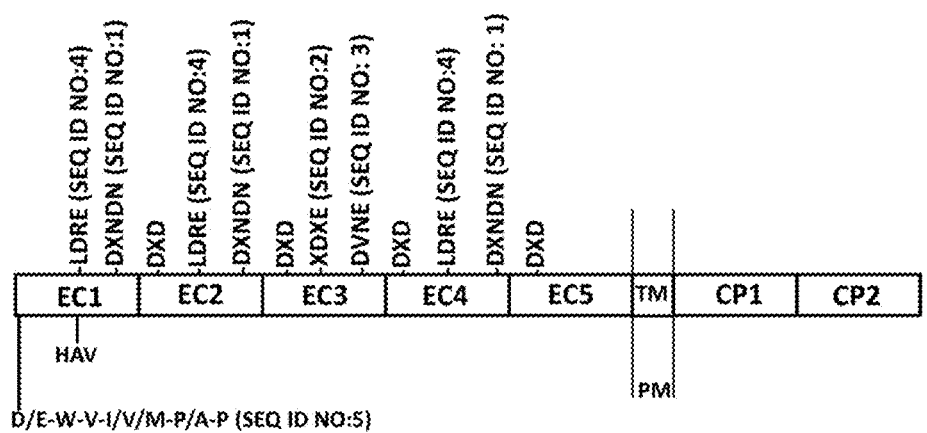
FIG. 1 is a diagram depicting the structure of classical CADs.

The present teachings include descriptions that are not intended to limit the scope of any aspect or claim. The examples and methods are provided to further illustrate the present teachings. Those of skill in the art, in light of the present disclosure, will appreciate that many changes can be made in the specific embodiments that are disclosed and still obtain a like or similar result without departing from the spirit and scope of the present teachings. As used herein, the singular forms "a", "an" and "the" are intended to include the plural forms as well, unless the context indicates otherwise.

Methods

Methods and compositions described herein utilize laboratory techniques well known to skilled artisans. Such techniques can be found in laboratory manuals such as Sambrook, J., et al. Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Behringer, R., et al., Manipulating the Mouse Embryo: A Laboratory Manual, Fourth Edition, Cold Spring Harbor Laboratory Press, Cold Spring Harbor, N.Y., 2014; Harlow, E., Using Antibodies: A Laboratory Manual, Cold Spring Harbor Laboratory Press, Cold Spring Harbor, N.Y., 1999; Harlow and Lane, Antibodies: A Laboratory Manual, Cold Spring Harbor Laboratory, 1988; and Carruthers, W., and Coldham, I., Modern Methods of Organic Synthesis (4th Edition), Cambridge University Press, Cambridge, U.K., 2004. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

Within certain cell adhesion assays, the addition of a cell adhesion antagonist to cells that express a cadherin results in disruption of cell adhesion. A "cadherin-expressing cell," as used herein, can be any type of cell that expresses at least one cadherin on the cell surface at a detectable level, using a standard technique such as immunocytochemical protocols (e.g., Devemy, E. and Blaschuk, O. W., Peptides 30:1539-1547, 2009). Non-limiting examples of cadherin-expressing cells include stem, progenitor, stromal, mural, lymphocytic, endothelial, epithelial, neural and cancer cells.

Previous studies have shown that pancreatic tumors can be composed of 90% stromal cells (Olive, K. P., et al., 2009, *Science* 1061, 1457-1461; Olive, K. P., 2015, *Clin. Cancer Res.* 21, 3366-3368). Cancer-associated fibroblasts (CAFs) are one of the major cell types present in the tumor stroma (reviewed by Pandol, S., et al., 2009, *Clin. Gastroenterol. Hepatol.* 7, S44-47; Karagiannis, G. S., et al., 2012, *Mol. Cancer Res.* 10, 1403-1418; Joyce, J. A. and Fearon, D. T., 2015, *Science* 348, 74-80). They aggregate peritumorally and encircle cancer cells invading adjacent normal tissues. CAFs support pancreatic cancer (PC) cell survival and protect these cells from attack by the immune system (Joyce, J. A. and Fearon, D. T., 2015, *Science* 348, 74-80), as well as prevent access of anti-cancer drugs to the PC cells (Olive, K. P., 2015, *Clin. Cancer Res.* 21, 3366-3368).

In some embodiments, an N-cadherin antagonist of the present teachings can be used to treat rheumatoid arthritis (RA) and other chronic inflammatory joint diseases. An N-cadherin antagonist of the present teachings can also be used to treat dogs and other animals. The cause of RA is unknown. It is an auto-immune disease that causes chronic joint inflammation. Previous RA treatments involve targeting cytokines such as TNF-α and IL-6 with monoclonal antibodies (Mabs) to suppress their inflammatory actions. Mabs against TNF-α are now being injected subcutaneously. Non-anti-TNF-α therapies are needed because 40% of patients with RA are not responsive to TNF-α based therapies.

The present teachings disclose cell adhesion antagonists, including compounds that can inhibit or modulate classical cadherin-mediated processes, such as cell adhesion. In various configurations, a compound of the present teachings can be a small molecule antagonist, such as a compound with a molecular weight <1,000. In various configurations, a compound of the present teachings can be an analogue of piperidin-4-amine. The present teachings also include pharmaceutically acceptable salts, stereoisomers and prodrugs of the disclosed compounds. The present teachings further include various uses of the cell adhesion antagonists. In addition, the present teachings include methods for compound synthesis.

In various embodiments, the present teachings include methods for inhibiting a classical cadherin-mediated cell function. In various configurations, cells that express a classical cadherin can be contacted with an antagonist of the present teachings either in vivo or in vitro. Such contact can inhibit a cadherin-mediated cell function, such as, but not limited to, cell adhesion. In some aspects, an antagonist of the present teachings can inhibit cell-substratum adhesion. In some aspects, an antagonist of the present teachings can inhibit cell-cell adhesion.

In some embodiments, an antagonist of the present teachings can comprise one or more peptidomimetics of a classical cadherin Trp-containing cell adhesion recognition (CAR) sequence. In some aspects, a peptidomimetic can comprise a classical cadherin Trp-containing CAR sequence and one or more additional CAR sequences. In some aspects, an additional CAR sequence can be derived from a classical cadherin. In some aspects, an additional CAR sequence can be derived from a non-cadherin cell adhesion molecule. In some embodiments, a composition of the present teachings can further comprise an antibody or antigen-binding fragment thereof that specifically binds a cell adhesion compound.

Prodrugs

The term "prodrug" as used herein refers to a compound that when administered to a biological system generates a compound of the present teachings which modulates cadherin activity. In various configurations, a compound of the present teachings can be formed from a prodrug as a result of: (i) spontaneous chemical reaction(s), (ii) enzyme catalyzed chemical reaction(s), (iii) photolysis, and/or (iv) metabolic chemical reaction(s). A prodrug can comprise a labile group (a "prodrug moiety") which can separate from an active compound during metabolism, systemically, inside a cell, by hydrolysis, enzymatic cleavage, or by some other process (Bundgaard, Hans, "Design and Application of Prodrugs" in A Textbook of Drug Design and Development (1991), P. Krogsgaard-Larsen and H. Bundgaard, Eds. Harwood Academic Publishers, pp. 113-191). Enzymes which are capable of an enzymatic activation mechanism with a prodrug of the present teachings include, but are not limited to, amidases, esterases, microbial enzymes, phospholipases, cholinesterases, and phosphatases. Prodrug moieties can serve to enhance solubility, absorption and lipophilicity to optimize drug delivery, bioavailability and/or efficacy. A prodrug moiety can include an active metabolite or drug itself. Exemplary prodrug moieties include hydrolytically sensitive or labile acyloxymethyl esters —$CH_2OC(=O)R^{99}$ and acyloxymethyl carbonates —$CH_2C=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl.

In some embodiments, an antagonist of the present teachings can be used to modulate a function mediated by a classical cadherin, such as cell adhesion. In some embodiments, the present teachings include methods of assessing activity of an antagonist. In some aspects, such activity can be assessed using, for example and without limitation, an assay disclosed herein.

Antagonist Modification and Formulations

In some embodiments, a compound of the present teachings can be linked to one or more additional molecules. In some configurations, multiple cell adhesion antagonists (which can be identical or different) can be linked to a support material, such as a support molecule, such as, for example and without limitation, keyhole limpet hemocyanin, or to a solid support, such as, for example and without limitation, a polymeric matrix. In some configurations, a polymeric matrix can be, for example and without limitation, a membrane or microstructure, such as an ultrathin film, a container surface such as, for example, the surface of a tissue culture plate or the interior surface of a bioreactor, or a bead or other microparticle, which can be prepared from a variety of materials such as glass, plastic or ceramics. In some configurations, a support material can be a biodegradable support materials, such as, for example and without limitation, cellulose, a polymeric cellulose derivative such as, for example, a cellulose ester or a cellulose ether, such as methyl cellulose, ethyl cellulose, or carboxymethyl cellulose, collagen, spider silk or a polyester such as, without limitation, a polyester derived from hydroxy acids and/or lactones, or a suture, for example a suture described in U.S. Pat. No. 5,245,012. In some embodiments, a cell adhesion antagonist comprising other CAR sequence(s) (e.g., HAV, RGD or LYHY (SEQ ID NO: 6)) can be attached to a support such as a polymeric matrix. In some aspects, an antagonist comprising other CAR sequence can be attached to a support in an alternating pattern with a compound of the present teachings.

Methods for linking a cell adhesion antagonist of the present teachings to a support material can be adapted from methods known to persons of ordinary skill in the art. In some aspects, attachment can be achieved through non-covalent association, such as adsorption or affinity. In some aspects, attachment can be achieved via covalent attachment. In some aspects, covalent attachment can be a direct linkage between an antagonist and functional groups on the support. In some aspects, covalent attachment can be via a cross-linking agent. In some configurations, attachment of an antagonist by adsorption can be achieved by contact, in a suitable buffer, with a solid support. In some configurations, contact time for establishing attachment by adsorption can vary with temperature. In some aspects, attachment can be achieved by contact lasting at least 5 seconds, or up to 1 day or longer, and can be between about 10 seconds and 1 hour.

In various configurations, covalent attachment of an antagonist of the present teachings to a molecule or solid support can be achieved by first reacting the support material with a bifunctional reagent that can also react with a functional group, such as a hydroxyl or amino group, on the antagonist. For example and without limitation, an antagonist of the present teachings can be bound to a polymeric support or coating using benzoquinone, by antagonist or by condensation of an amino group on the support with a carboxylic acid on the antagonist. In some configurations, a linkage can be generated via amino groups using glutaraldehyde. In some configurations, an antagonist can be linked to cellulose via ester linkages. In some configurations, amide linkages can be used for linkage to other molecules such as keyhole limpet hemocyanin or other support materials. In some configurations, multiple cell adhesion antagonists can be attached, for example, by random coupling, in which such molecules can be mixed with a matrix support, e.g., in equimolar amounts, and allowed to couple at random.

In some embodiments, a pharmaceutically active compound such as a drug can be linked to an antagonist of the present teachings. As used herein, the term "drug" refers to any bioactive agent intended for administration to a mammal such as a human, a farm animal or a companion animal, to prevent or treat a disease or other undesirable condition. Drugs can include, without limitation, antibiotics, hormones, growth factors, proteins and peptides.

In some embodiments, the present teachings also include compositions (e.g., pharmaceutical compositions) comprising one or more cell adhesion antagonists of the present teachings. In some configurations, a composition can comprise one or more cell adhesion antagonists in combination with one or more pharmaceutically or physiologically acceptable carriers, diluents or excipients. In various configurations, such compositions can comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. In some embodiments, a composition of the present teachings can be formulated as a lyophilisate. In some configurations, one or more cell adhesion antagonists (alone or in combination with a drug) can be encapsulated within liposomes using well known technology. In various aspects, a composition of the present teachings can be formulated for any mode of administration known to skilled artisans, including, for example and without limitation, topical, oral, nasal, rectal, intravenous, intracranial, intraperitoneal, subcutaneous, or intramuscular administration.

In some embodiments, a composition of the present teachings can comprise one or more pharmaceutically active substances which can be linked to a cell adhesion antagonist of the present teachings. In various aspects, a pharmaceutically active substance can be linked to a cell adhesion antagonist by a covalent linkage or a non-covalent linkage. In various aspects, a pharmaceutically active substance can be linked directly to a cell adhesion antagonist directly or through a linker such as a covalent linker.

In some embodiments, a composition of the present teachings can comprise one or more pharmaceutically active substances and a cell adhesion antagonist of the present teachings. In various configurations, virtually any pharmaceutically active substance can be administered in combination with an antagonist of the present teachings, for a variety of purposes as described below. Examples of types of pharmaceutically active substances (including drugs) that can be administered with an antagonist include analgesics, anesthetics, antianginals, antifungals, antibiotics, anticancer drugs (e.g., taxol or mitomycin C), anti-inflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antipsychotics, antipyretics, antiseptics, anti-signaling agents (e.g., protein kinase C antagonists or antagonists of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, immunostimulatory agents (e.g. blocking antibodies to immune checkpoint regulators such as programmed cell death protein and cytotoxic T-lymphocyte-associated protein 4), narcotic antagonists, parasympathomimetics, sedatives, stimulants, sympathomimetics, toxins (e.g., cholera toxin), tranquilizers and urinary anti-infectives.

In some embodiments, an antagonist of the present teachings can be combined with a diagnostic agent for imaging purposes. In various configurations, an antagonist and a diagnostic agent can be linked, or both can be free within a composition. Diagnostic agents can include a substance that can be administered to a subject such as a human patient. A diagnostic agent such as a radiotracer can distribute within the subject; imaging of the distribution of the diagnostic agent can be used for diagnosis of a disease. Non-limiting examples of diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In some configurations, such agents can be attached to an antagonist of the present teachings using a variety of techniques as described above, and can be present in any orientation.

In various aspects, a composition of the present teachings can be administered as part of a sustained release formulation (i.e., a formulation such as a capsule or sponge that effects a slow release of an antagonist following administration). Such formulations can be prepared using well known technology and administered, for example and without limitation, by oral, rectal or subcutaneous implantation, or by implantation at the selected target site. In some configurations, a sustained-release formulation can contain an antagonist of the present teachings dispersed in a carrier matrix and/or contained within a reservoir surrounded by a rate controlling membrane (see, e.g., European Patent Application 710,491 A). In some aspects, a carrier for use with such a formulation can be biocompatible. In some aspects, a carrier for use with such a formulation can also be biodegradable. In various aspects, the amount of antagonist contained within a sustained release formulation can depend upon the site of implantation, the rate and expected duration of release and the nature of the condition to be treated or prevented.

In some embodiments, a composition of the present teachings can be administered in a manner appropriate to the disease or disorder to be treated or prevented. Dosages, durations and frequency of administration can be determined by such factors as the condition of the patient, the type and severity of the patient's disease or disorder and the method of administration. In some configurations, a dosage and treatment regimen can be determined for providing the antagonist(s) in an amount sufficient for therapeutic and/or prophylactic benefit. In some configurations, an antagonist or pharmaceutical composition as described herein can be administered at a dosage ranging from 0.001 to 100 mg/kg body weight, preferably from 0.1 to 20 mg/kg, on a regimen of single or multiple daily doses. In some configurations, an antagonist described herein can be administered topically, via a cream or ointment. In some aspects, a cream or ointment can comprise the antagonist in a concentration ranging from 0.00001% to 1%, preferably 0.0001% to 0.002%.

In some configuration, an antagonist of the present teachings can be administered via a fluid composition. In some aspects, a fluid composition can comprise an antagonist of the present teachings at a concentration of about 10 ng/ml to 5 mg/ml, preferably from about 10 µg/ml to 2 mg/mL antagonist. Dosages can be determined using experimental models and/or clinical trials. In some configurations, patients can be monitored for therapeutic effectiveness using assays suitable for the condition being treated or prevented.

Therapeutic Methods Employing Antagonists

In various embodiments, a cell adhesion antagonist disclosed herein can be used for modulating the adhesion of cadherin-expressing cells (i.e., cells that express at least one cadherin such as, without limitation, E-cadherin, N-cadherin, P-cadherin or R-cadherin). Such modulation can be performed in vitro and/or in vivo, preferably in a mammal such as a human.

In various embodiments, methods involving the disruption of cell adhesion described herein can have an advantage over prior techniques in that they can permit the passage of large and/or charged molecules across barriers of cadherin-expressing cells. In various embodiments, a cell adhesion antagonist described herein can be used to disrupt or enhance cell adhesion in a variety of contexts. Within various aspects of each of the methods described herein, one or more cell adhesion antagonists can be administered alone, or within a pharmaceutical composition.

In various aspects, in a method for inhibiting cell adhesion, a cadherin-expressing cell can be contacted with an antagonist of the present teachings under conditions and for a time sufficient to permit inhibition of a cadherin-mediated function. Cadherin-expressing cells include, but are not limited to, epithelial cells, endothelial cells, neural cells, stromal cells, mural cells, stem cells, progenitor cells, tumor cells and lymphocytes. In various aspects, contact can be achieved in vitro, or in vivo by administration of a pharmaceutical composition as disclosed herein.

The present teachings include methods for reducing unwanted cellular adhesion by administration of a cell adhesion antagonist, or a composition comprising a cell adhesion antagonist, as disclosed herein. Unwanted cellular adhesion can occur, for example between tumor cells, between tumor cells and normal cells or between normal cells as a result of surgery, injury, chemotherapy, disease, inflammation or other condition jeopardizing cell viability or function.

In various configurations, a fluid composition for the topical administration of antagonist(s) (comprising, for example, physiological saline) can comprise an amount of antagonist as described supra, for example and without limitation, at a concentration from 10 µg/ml to 1 mg/ml. A cream or ointment can be formulated as described supra. In some configurations, topical administration in the surgical field can be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration can be used to achieve similar results.

The present teachings include methods of enhancing the delivery of a drug across the skin of a mammal. While transdermal delivery of drugs can be a convenient and non-invasive method that can be used to maintain relatively constant blood levels of a drug, it can be necessary to perturb adhesion between the epithelial cells (keratinocytes) and the endothelial cells of the microvasculature. A wide variety of drugs can be transported across the epithelial and endothelial cell layers of skin, for systemic or topical administration through permeabilization resulting from contact with a cell adhesion antagonist of the present teachings. For example and without limitation, a drug can be delivered to a melanoma, or can enter the blood stream of a subject for delivery to other sites within the body.

In some embodiments, to enhance the delivery of a drug through the skin, a cell adhesion antagonist of the present teachings and a drug can be contacted with the skin surface. Contact can be achieved by direct application of the antagonist, for example within a composition formulated as a cream or gel, or through use of any of a variety of skin contact devices for transdermal application (such as those described in European Patent Application No. 566,816 A; U.S. Pat. Nos. 5,613,958; 5,505,956). In some aspects, a skin patch can be used for administration, for example for administering a slow-release formulation. In some configurations, a patch can contain a reservoir of antagonist and drug separated from the skin by a membrane through which the drug diffuses. Within some patch designs, the cell adhesion antagonist and drug can be dissolved or suspended in a polymer or adhesive matrix that can be placed in direct contact with a subject's skin. The cell adhesion antagonist and drug can then diffuse from the matrix into the skin. In various configurations, antagonist(s) and drug(s) can be contained within the same composition or skin patch. In various configurations, antagonist(s) and drug(s) can be separately administered. In various aspects, transfer of a drug across the skin and to a target tissue can be demonstrated and quantified based on in vitro studies using, for example and without limitation, a Franz cell apparatus, and can be evaluated in vivo by methods known to skilled artisans. For example and without limitation, drug transfer across the skin can be monitored by measurement over time of the serum level of a drug administered to the skin with a cell adhesion antagonist of the present teachings.

In some embodiments, transdermal drug delivery as described herein can be used when a constant rate of drug delivery is desired. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein can permit the maintenance of more constant levels for long periods of time (e.g., days), which can allow adequate pain control and mental alertness at the same time. Insulin provides another such example. Many diabetic patients need to maintain a constant baseline level of insulin that is different from their needs at the time of meals. In some aspects, a baseline level of insulin can be maintained using transdermal administration of insulin in combination with a cell adhesion antagonist of the present teachings. In some aspects, an antibiotic can also be administered transdermally at a constant rate, whereby adequate bactericidal blood levels can be maintained, while avoiding toxic high levels (e.g., levels of gentamycin that can result in renal toxicity).

In some aspects, drug delivery by the methods of the present teachings include methods of drug administration. Parenteral administration of a drug to a newborn or infant can be difficult because of the need to identify veins of acceptable caliber for catheterization. Transdermal drug delivery in accordance with the present teachings permits easier management of such patients. Furthermore, transdermal drug delivery in accordance with the present teachings can allow certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein can be more convenient than parenteral administration.

Transdermal administration as described herein also allows the gastrointestinal tract to be bypassed in situations where parenteral administration would not be practical. For example, there is a need for methods of administering therapeutic peptides and proteins, which are typically digested within the gastrointestinal tract. The methods described herein permit administration of such compounds and can allow administration over long periods of time. In some configurations, a patient who has problems with absorption through their gastrointestinal tract because of prolonged ileus or a gastrointestinal disease that limits drug absorption can also benefit from a drug administered transdermally with an antagonist of the present teachings Furthermore, there are clinical situations in which patient compliance with standard methods can be difficult or problematical for which transdermal delivery in accordance with the disclosed methods can be beneficial. For example and without limitation, a subject with a mental problem (e.g., Alzheimer's disease or psychosis) can be managed by a constant delivery rate of drug without having to rely on their ability to take their medication at specific times of the day. Also, a subject who forgets to take their drugs as prescribed, such as, for example, a subject with a disease with few or no symptoms, such as, for example, hypertension, can be at risk of forgetting to take their medication as prescribed.

Subject compliance can be greater if the subject merely needs to put on a skin patch periodically (e.g., every 3 days).

For a subject taking multiple drugs, a device for transdermal application such as a skin patch can be formulated with a combination of drugs that are frequently used together. For example, many heart failure patients are given digoxin in combination with furosemide. In various aspects, a single skin patch can be used to administer a combination of both drugs with the aid of a cell adhesion antagonist of the present teachings. In various aspects, a transdermal delivery system can facilitate administration, can reduce the risk of errors (taking the correct pills at the appropriate time is often confusing to older people), can reduce the psychological strain of taking "so many pills," can reduce skipped dosage because of irregular activities and/or can enhance compliance.

The methods described herein can be applicable not only to humans, but can also have a variety of veterinary uses, such as, in non-limiting example, the administration of growth factors or hormones (e.g., for fertility control) to an animal such as, without limitation, a companion animal, such as, without limitation, a dog or a cat, or a farm animal, such as, without limitation, a horse, a cow, a goat, a sheep, or a pig.

As noted above, a wide variety of drugs can be administered according to the methods disclosed herein. Some examples of drug categories that can be administered transdermally include anti-inflammatory drugs (e.g., in arthritis and in other condition) such as, without limitation, all NSAID, indomethacin, prednisone; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as, for example, amitriptylin, imipramin, or Prozac; antihypertensive drugs (e.g., to improve compliance and reduce side effects associated with fluctuating blood levels), such as diuretics and beta-blockers (which can be administered by the same patch; for example, furosemide and propranolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant), and steroids such as testosterone.

Numerous other drugs can be administered as described herein, including naturally occurring and synthetic hormones, growth factors, proteins and peptides. For example, insulin and human growth hormone, growth factors such as erythropoietin, interleukins and interferons can be delivered transdermally in combination with a cell adhesion antagonist of the present teachings.

In some embodiments, the present teachings include kits for administering a drug via the skin of a mammal. In various aspects, a kit can comprise a device for transdermal application (e.g., a skin patch) in combination with, or impregnated with, one or more cell adhesion antagonists of the present teachings. In some aspects, a drug can also be included within a kit.

In some embodiments, the present teachings include methods for inducing apoptosis in a cancer-associated fibroblast. These methods include contacting cancer-associated fibroblasts with a cell adhesion antagonist of the teachings. Alternatively, in some embodiments, a separate modulator of cell adhesion (e.g., integrin- and/or occludin-mediated) can be administered in conjunction with a cell adhesion antagonist of the present teachings, either within the same pharmaceutical composition or separately.

In some aspects, methods of the present teachings can be used for administration of one or more anti-cancer drugs. In some aspects, methods of the present teachings can be used for administration of a monoclonal antibody that blocks the function of immune system checkpoint regulators, such as, without limitation, nivolumab, pembrolizumab, and durvalumab.

In various aspects, the present teachings include methods for treating cancer and/or inhibiting (lessening or reducing) cancer metastasis in a mammal. The formation of new capillaries is a prerequisite for tumor growth and the emergence of metastases. Administration of a cell adhesion antagonist as described herein can disrupt the growth of such blood vessels, thereby providing effective therapy for the cancer, for example by reducing or inhibiting cancer progression, including reducing tumor growth and/or inhibiting metastasis. In various configurations, an antagonist of the present teachings can be used to treat a cancer metastasis. In various configurations, an antagonist of the present teachings can be used to treat a leukemia, a lymphoma or a multiple myeloma. Alternatively, a separate modulator of cell adhesion (e.g., Dsg- and/or Dsc- and/or integrin- and/or occludin-mediated) can be administered in conjunction with an antagonist of the present teachings, either within the same pharmaceutical composition or separately. Additional embodiments can employ antibody or Fab fragments directed against a compound of the present teachings.

In some aspects, an antagonist can be administered alone (e.g., via the skin) or within a pharmaceutical composition. In some aspects, the present teachings include methods for treating melanomas and certain other accessible tumors. These methods can comprise administration of a cell adhesion antagonist by injection or by topical administration. In some aspects, the present teachings include methods for treating or preventing an ovarian cancer. In some configurations, a method can comprise flushing the peritoneal cavity with a composition comprising a cell adhesion antagonist of the present teachings. In some aspects, the present teachings include methods for treating or preventing growth of a tumor, such as, for examples, a bladder tumor, a bronchial tumor or a tracheal tumor. In various configurations, a tumor can be treated by injection of a cell adhesion antagonist of the present teachings into the cavity. In other aspects, a composition of the present teachings can be administered systemically, and targeted to the tumor using any of a variety of specific targeting agents. In various aspects, the amount of a cell adhesion antagonist administered, and the administration route, can be determined by a person of skill in the art using routine methods. In various aspects, the effectiveness of a cancer treatment or inhibition of metastasis can be evaluated using well known clinical measurements, such as, for example, measurement of the level of a serum tumor marker (e.g., CEA or PSA).

The present teachings include methods for enhancing the immune response to a tumor. These methods can comprise administering a cell adhesion antagonist of the present teachings, in combination with an immunostimulatory drug (e.g., an antibody to an immune system checkpoint regulator) to a tumor-bearing mammal (see Joyce, J. A., and Fearon, D. T., Science 348:74-80, 2015.) Alternatively, a separate modulator of cell adhesion (e.g., Dsg- and/or Dsc- and/or integrin- and/or occludin-mediated) can be administered in conjunction with a cell adhesion antagonist of the present teachings, either within the same pharmaceutical composition or separately.

A wide variety of anti-cancer drugs can be administered according to the methods provided herein. In some aspects, a monoclonal antibody for immunotherapy, such as, for example, nivolumab, pembrolizumab, or durvalumab can be administered by in combination with a cell adhesion antagonist of the present teachings.

In some embodiments, the present teachings include methods of enhancing or inducing apoptosis in a cadherin-expressing cell such as a cancer cell, an endothelial cell (e.g., Erez, N., et al., Exp. Cell Res. 366-378, 2004) or a smooth muscle cell (e.g., Koutsouki, E. et al., Arterioscler. Thromb. Vasc. Biol. 25: 982-988, 2005) by administration of a cell adhesion antagonist of the present teachings.

In some embodiments, an antagonist of the present teachings can be used to inhibit (i.e., reduce or lessen) angiogenesis (i.e., the growth of blood vessels from pre-existing blood vessels) in a mammal such as a human. Inhibition of angiogenesis can be beneficial, for example, in patients afflicted with diseases such as cancer or arthritis. Alternatively, a separate modulator of cell adhesion (e.g., a modulator or integrin- and/or occludin-mediated cell adhesion) can be administered in conjunction with a cell adhesion antagonist of the present teachings, either within the same pharmaceutical composition or separately.

In some configurations, the effect of a particular cell adhesion antagonist on angiogenesis can be evaluated using a standard blood vessel formation assay such as, for example, a chick chorioallantoic membrane assay (Iruela-Arispe, M. L., et al., Molecular Biology of the Cell 6:327-343, 1995). Briefly, an antagonist can be embedded in a mesh comprising a collagen such as VITROGEN (Advanced BioMatrix, Inc., San Diego, Calif.) at a selected concentration (e.g., ranging from about 1 to about 100 µg/mesh). A mesh can then be applied to chick chorioallantoic membranes. After 24 hours, the effect of a cell adhesion antagonist can be determined using computer assisted morphometric analysis.

In some configurations, an antagonist of the present teachings can be used for modulating the immune system of a mammal. Cadherins are expressed on immature B and T cells (thymocytes and bone marrow pre-B cells), as well as on specific subsets of activated B and T lymphocytes and some hematological malignancies (see, e.g., Lee, M. G., et al., J. Immunol. 152:5653-5659, 1994; Munro, S. B., et al., Cellular Immunol. 169:309-312, 1996; Tsutsui, J., et al., J. Biochem. 120:1034-1039, 1996; Cepek, K. L., et al., Proc. Nat'l. Acad. Sci. USA 93:6567-6571, 1996). In some aspects, an antagonist can be used to modulate specific steps within cellular interactions during an immune response or during the dissemination of malignant lymphocytes.

In some aspects, an antagonist as described herein can be used to treat a disease associated with excessive generation of otherwise normal T cells. Without being limited by theory, it is believed that the interaction of cadherins on maturing T cells and B cell subsets can contribute to protection of these cells from programmed cell death. A cell adhesion antagonist can decrease such interactions, leading to the induction of programmed cell death. Accordingly, cell adhesion antagonists of the present teachings can be used to treat certain types of diabetes and rheumatoid arthritis, particularly in young children where the cadherin expression on thymic pre-T cells is greatest.

In some aspects, an antagonist of the present teachings can be administered to a patient afflicted with certain skin disorders (such as cutaneous lymphomas), acute B cell leukemia, or excessive immune reactions involving the humoral immune system and generation of immunoglobulins, such as allergic responses and antibody-mediated graft rejection. In some aspects, an antagonist of the present teachings can be administered to a patient with circulating cadherin-positive malignant cells (e.g., during regimes where chemotherapy or radiation therapy is eliminating a major portion of the malignant cells in bone marrow and other lymphoid tissue). In some aspects, an antagonist of the present teachings can be administered to a patient undergoing transplantation with peripheral blood stem cells. In some aspects, an antagonist of the present teachings can be administered to a patient along with a separate modulator of cell adhesion (e.g., Dsg- and/or Dsc- and/or integrin- and/or occludin-mediated), either within the same pharmaceutical composition or separately.

Within the above methods, an antagonist can be administered systemically (e.g., by injection) or topically. In some aspects, an antagonist can be linked to a targeting agent. For example, targeting to the bone marrow can be beneficial. A suitable dosage can be one sufficient to effect a statistically significant reduction in the population of B and/or T cells that express cadherin and/or an improvement in the clinical manifestation of the disease being treated. Dosages can range as described above.

In some aspects, an antagonist of the present teachings can be used to increase vasopermeability in a mammal by administering one or more antagonists of the present teachings or pharmaceutical compositions. Within blood vessels, endothelial cell adhesion (mediated by N-cadherin) results in decreased vascular permeability. Accordingly, administration of an antagonist of N-cadherin mediated adhesion can be used to increase vascular permeability. Alternatively, a separate modulator of cell adhesion (e.g., occludin-mediated) can be administered in conjunction with the modulating agent(s), either within the same pharmaceutical composition or separately.

Within certain embodiments, an antagonist of the present teachings can be used to facilitate the penetration of anti-tumor therapeutic or diagnostic agents (e.g., monoclonal antibodies) through endothelial cell permeability barriers and tumor barriers. In some aspects, a cell adhesion antagonist of the present teachings can further comprise an N-cadherin HAV sequence. In some aspects, a cell adhesion antagonist of the present teachings and an additional modulating agent which disrupts N- and/or E-cadherin mediated adhesion can be administered concurrently.

The present teachings also include methods for treating fibrosis, such as idiopathic pulmonary fibrosis (IPF) by inhibiting N-cadherin function using a cell adhesion antagonist of the present teachings. In some configurations, a separate modulator of cell adhesion (e.g., Dsg- and/or Dsc- and/or integrin- and/or occludin-mediated) can be administered in conjunction with a cell adhesion antagonist of the present teachings, either within the same pharmaceutical composition or separately.

EXAMPLES

Unless specifically presented in the past tense, an example can be a prophetic or an actual example.

Example 1

This example illustrates the effect of a cell adhesion antagonist on cell adhesion in a neurite outgrowth assay.

Within a representative neurite outgrowth assay, neurons are cultured on a monolayer of cells (e.g., 3T3 fibroblasts) that express N-cadherin. Neurons grown on such cells (under suitable conditions and for a sufficient period of time) extend neurites that are typically, on average, twice as long as neurites extended from neurons cultured on 3T3 cells that do not express N-cadherin. For example, neurons can be cultured on monolayers of 3T3 cells transfected with cDNA encoding N-cadherin essentially as described by Doherty, P. and Walsh, F. S., Curr. Op. Neurobiol. 4:49-55, 1994; Williams, E. J., et al., Neuron 13:583-594, 1994; Hall, H., et al., Cell Adhesion and Commun. 3:441-450, 1996; Doherty, P. and Walsh, F. S., Mol. Cell. Neurosci. 8:99-111, 1994; and Safell, J. L., et al., Neuron 18:231-242, 1997. Briefly, monolayers of control 3T3 fibroblasts and 3T3 fibroblasts that express N-cadherin are established by overnight culture of 80,000 cells in individual wells of an 8-chamber well tissue culture slide. 3000 cerebellar neurons isolated from post-natal day 3 mouse brains are cultured for 18 hours on the various monolayers in control media (SATO/2% FCS), or media supplemented with various concentrations of the modulating agent. The cultures are then fixed and stained for GAP43 which specifically binds to the neurons and their neurites. The length of the longest neurite on each GAP43 positive neuron is measured by computer assisted morphometry.

Under the conditions described above, the presence of 10 micromolar of Compound 15

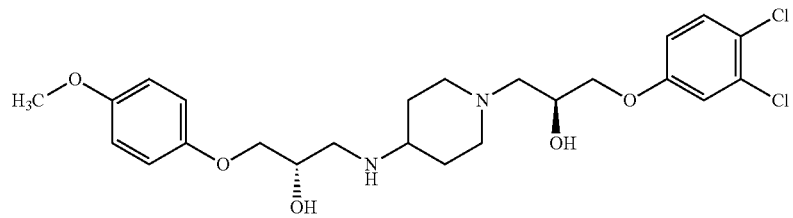 [SMILES: COc1ccc(OC[C@@H](O)CNC2CCN(C[C@H](O)COc3ccc(Cl)c(Cl)c3)CC2)cc1]

67 results in a decrease in the mean neurite length by at least 50%, relative to the length in the absence of modulating agent.

Example 2

This example illustrates the effect of a cell adhesion antagonist on classical cadherin mediated cell adhesion in a cell adhesion assay.

In these experiments, classical cadherin-expressing cells are plated under standard conditions that, in the absence of cell adhesion antagonist, permit cell adhesion. Disruption of cell adhesion is determined visually within 24 hours, by observing retraction of the cells from one another. By this assay, disruption of cell adhesion is observed in the presence of 1 micromolar of Compound 15

68

In these experiments, Panc-1 human pancreatic cancer cells were maintained in Dulbecco's minimum essential medium supplemented with 10% fetal calf serum at 37° C. in 5% $CO_2$ in air. All culture reagents were purchased from Invitrogen (Burlington, ON). Panc-1 cells (ATCC CRL-1469) were plated at 20,000 cells per well of a 4-well tissue culture slide (NalgeNunc, Naperville, Ill.). After 24 hours of culture, cells were treated for 24 hours with medium containing varying concentrations of compounds 15 and 16 dissolved in dimethylsulfoxide (DMSO; final concentration of 1% DMSO in the medium), or 1% DMSO alone in the medium and then fixed with 4% paraformaldehyde dissolved in phosphate buffered saline and stained with hematoxylin. Disruption of cell adhesion was determined visually within 24 hours, by observing retraction of the cells from one another.

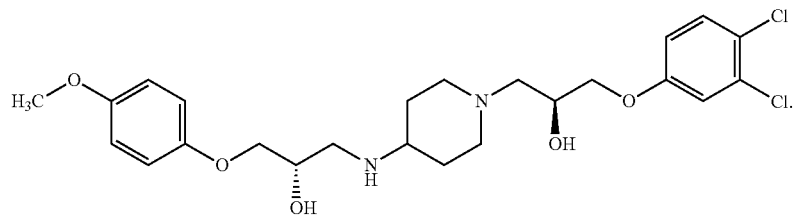 [SMILES: COc1ccc(OC[C@@H](O)CNC2CCN(C[C@H](O)COc3ccc(Cl)c(Cl)c3)CC2)cc1]

Example 3

This example illustrates the effect of a cell adhesion antagonist on N-cadherin mediated cell adhesion in a cell adhesion assay.

Bovine pulmonary artery endothelial cells are harvested by sterile ablation and digestion in 0.1% collagenase (type II; Worthington Enzymes, Freehold, N.J.). Cells are maintained in Dulbecco's minimum essential medium supplemented with 10% fetal calf serum and 1% antibiotic-antimycotic at 37° C. in 7% $CO_2$ in air. Cultures are passaged weekly in trypsin-EDTA and seeded onto tissue culture plastic at 20,000 cells/cm². Endothelial cultures are used at 1 week in culture, which is approximately 3 days after culture confluency is established. The cells are seeded onto coverslips and treated for 30 minutes with antagonist Compound 15

In order to determine the effect of the compounds on cell death, the medium was aspirated from the treated and untreated cultures and the non-adherent cells collected by centrifugation (1000 rpm for 5 min). The cells were resuspended in phosphate buffered saline and combined with trypan blue (Sigma). Cells were then put in a hemocytometer and the number of cells that excluded the trypan blue counted using a microscope to determine the number of live cells.

Figure 3A:
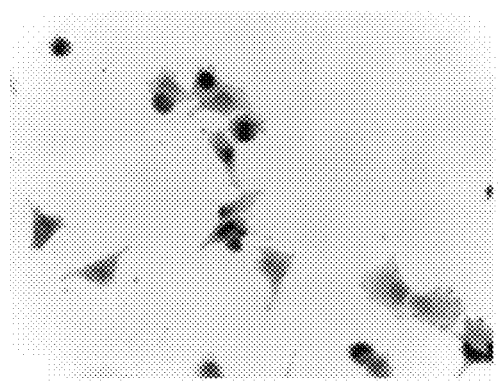
FIG. 3A-I illustrate light microscopy images of Panc-1 cancer cells that have been treated with cell adhesion antagonists of the present teachings.
Figure 3B:
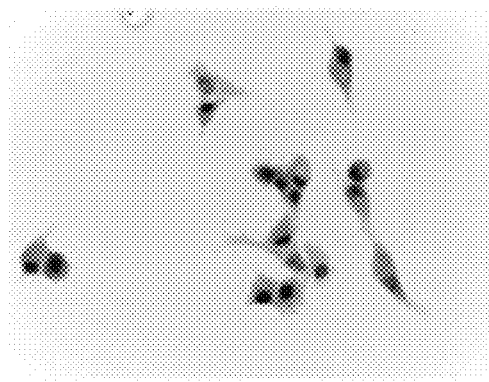
Figure 3C:
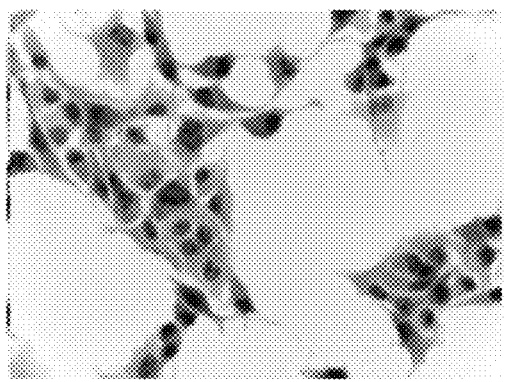
Figure 3D:
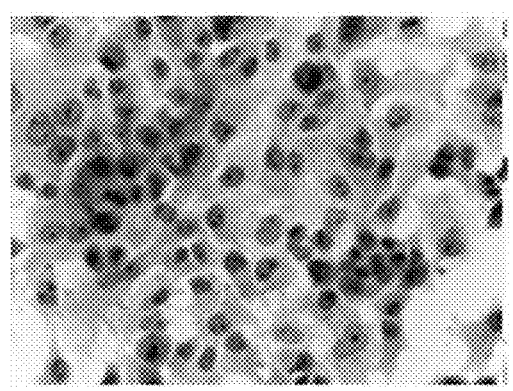
Figure 3E:
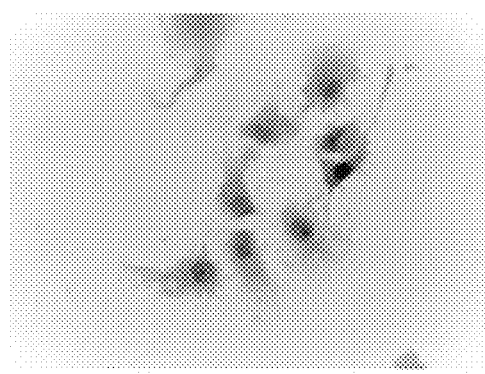
Figure 3F:
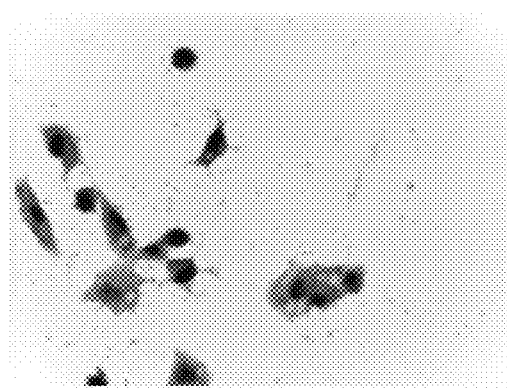
Figure 3G:
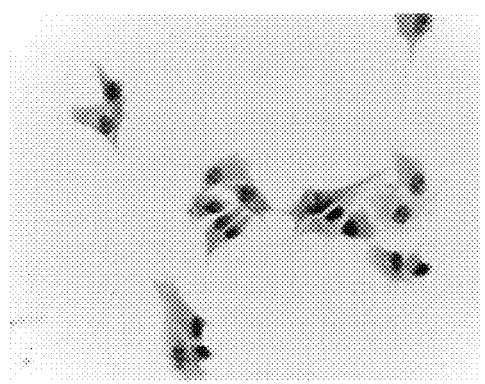
Figure 3H:
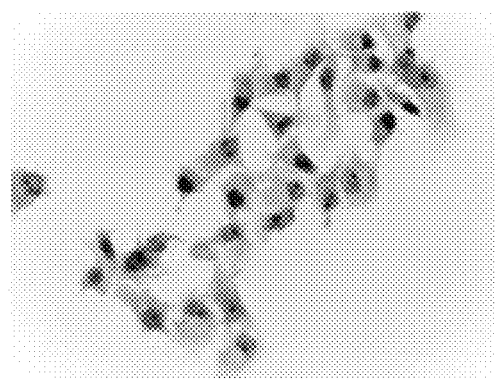
Figure 3I:
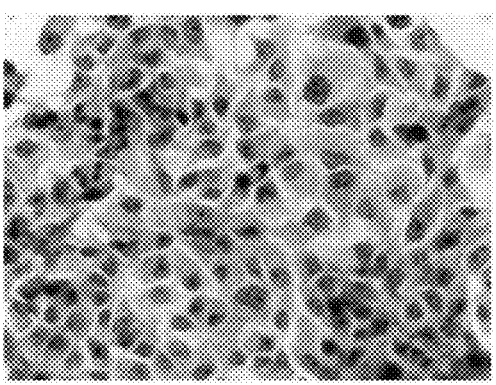

Compound 15 disrupted cell adhesion at concentrations of 100 μM (FIG. 3A), 10 μM (FIG. 3B), and 1 μM (FIG. 3C). The cell monolayer was not disrupted by compound 15 at a concentration of 0.1 μM (FIG. 3D), in comparison to the control (FIG. 3I). Compound 16 disrupted cell adhesion at concentrations of 100 μM (FIG. 3E), 10 μM (FIG. 3F), 1 μM (FIG. 3G), and 0.1 μM (FIG. 3H), as assessed by light microscopy. Compound 16 caused cell death at concentra-

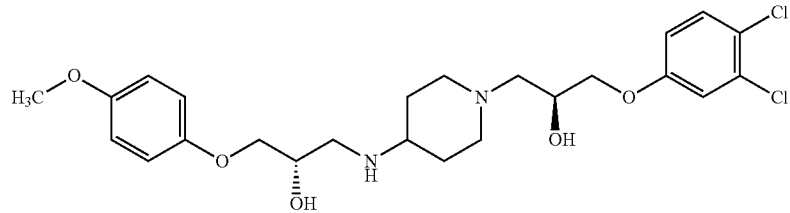 [SMILES: COc1ccc(OC[C@@H](O)CNC2CCN(C[C@H](O)COc3ccc(Cl)c(Cl)c3)CC2)cc1]

or a control compound at 10 μM and then fixed with 1% paraformaldehyde. Disruption of cell adhesion is determined visually within 24 hours, by observing retraction of the cells from one another.

Example 4

Figure 4:
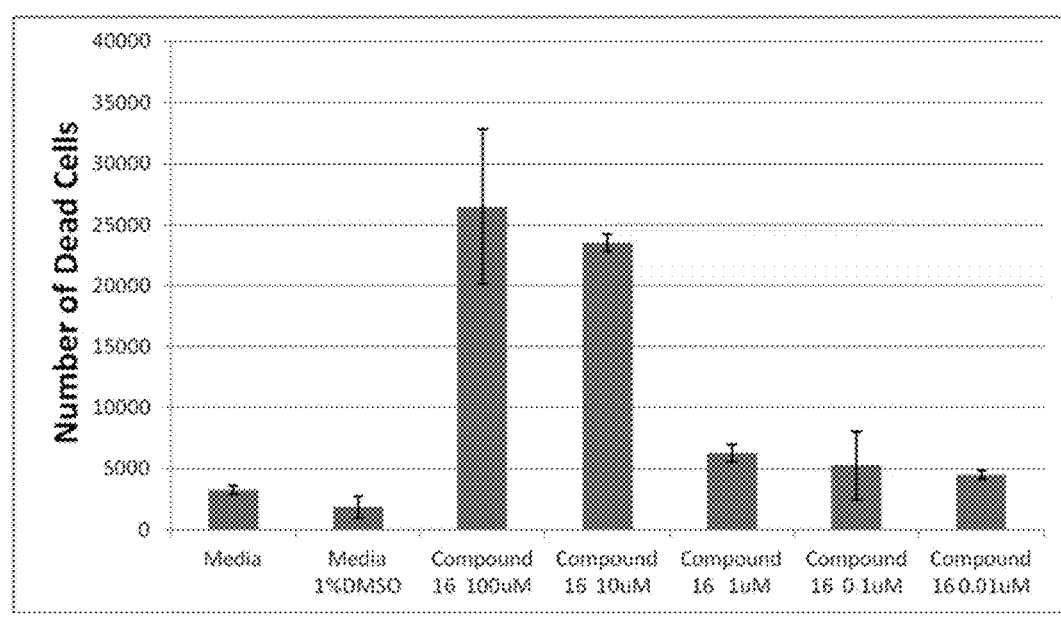
FIG. 4 illustrates the ability of cell adhesion antagonist Compound 16 (FIG. 2C) to cause Panc-1 cancer cell death.
Figure 5:
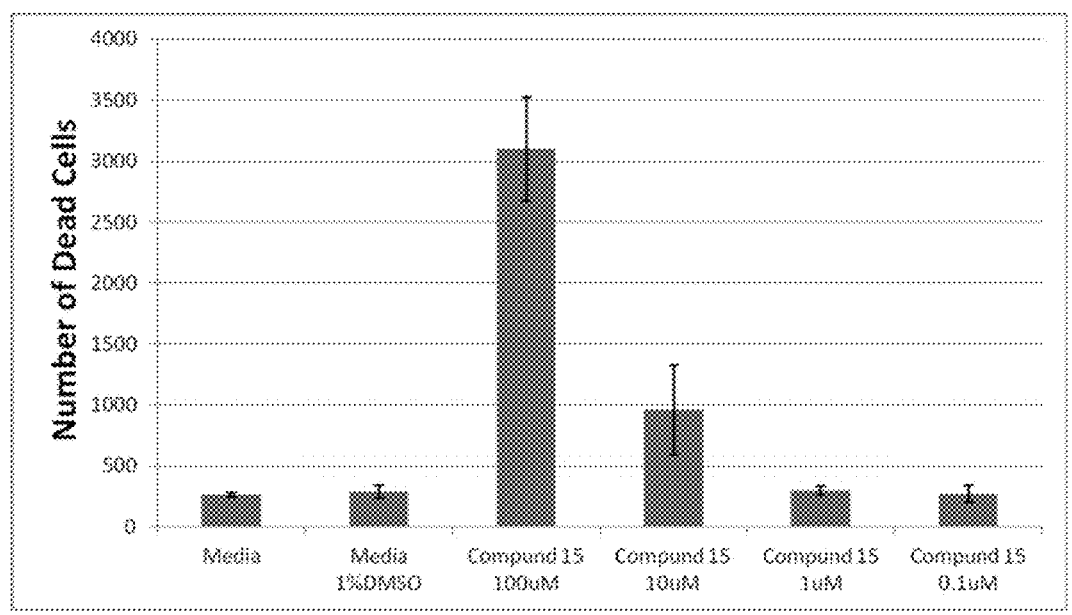
FIG. 5 illustrates the ability of cell adhesion antagonist Compound 15 (FIG. 2C) to cause Panc-1 cancer cell death.

This example demonstrates the effects of N-cadherin antagonists of the present teachings (compounds 15 and 16) on cancer cell adhesion.

tions of 1 μM, 10 μM and 100 μM (FIG. 4), whereas compound 15 caused cell death at concentrations of 10 μM and 100 μM, in comparison to the control (FIG. 5).

Example 5

This example demonstrates the effects of some N-cadherin antagonists of the present teachings (compounds 15 and 16) on N-cadherin-mediated cell adhesion.

In these experiments, a total of 2×10⁶ originally noncohesive embryonic mouse L929 fibroblasts (L cells) were transfected by electroporation in 400 μl transfection medium (RPMI 1640, 1% dextrose, 1 mM β-mercaptoethanol) with 40 μg pMiwcN chicken N-cadherin expression vector (Miyatani, S., et al., Science, 1989, 245, 631-635; Fujimori T., et al., Development, 1990, 110. 97-104). Neomycin resistance (pwlneo, GIBCO) was included for G418 selection. Transfected cells were diluted 1/100 and placed in medium containing 800 μg/ml G418 (GIBCO). Resistant cells were grown to confluence, detached by trypsin/$Ca^{2+}$ treatment, and stained with an anti-chicken N-cadherin antibody (NCD2, Zymed) on ice for 45 min. After several washes in Hanks' balanced salt solution, cells were mixed with a fluorescein isothiocyanate-conjugated secondary antibody and placed on ice for 30 min. N-cadherin-expressing cells were then autocloned into 96-well plates by using the CloneCyt Integrated Deposition System (Becton-Dickinson Immunocytometry Systems). Positive clones were reanalyzed by FACS and the L cell line LN5 was propagated for these studies.

The 3D spheroids were generated as follows. Cells were removed from near-confluent plates with TC (0.05% trypsin and 2 mM $Ca^{2+}$ in Hank's solution for 5-10 minutes), washed once with 1 mL 4° C. Hank's solution, and suspended at a concentration of $2.5\times10^6$ cells/ml in complete MEM supplemented with 2 mM $CaCl_2$ and varying concentrations of N-cadherin antagonists (Crocus Laboratories, Montreal, Quebec, Canada). The antagonists were compound 15 (MW=499.43) and compound 16 (MW=499.43). Stock solutions of the antagonists were prepared by dissolving the antagonists in DMSO at concentrations of 30 mM. Controls were made by suspending the cells as described above in the absence of antagonists with only the respective amount of DMSO added. Drops of the cell suspensions (10 microliters each) were deposited on the underside of a 10 cm tissue culture dish lid. The lid was then inverted and placed on dish containing 5 ml of PBS for hydration. Hanging drops were incubated under tissue culture conditions for 48 h, allowing the cells to coalesce at the base of the droplets and to form multi-layer aggregates. The tissue culture dish lid was then removed and the medium was gently aspirated. Aggregates (N=10-20) where then photographed under 4× lens and cell area was analyzed using ImageJ. Statistical differences were determined using ANOVA and Tukey's multiple comparison test.

Each of the antagonists tested from Crocus Laboratories contained cadherin antagonist properties at different potency levels. We determined the approximate minimum concentration needed for an anti-adhesion dose response on 3D spheroid N-cadherin mouse fibroblast (LN5) cells. These cells were prepared by forming a cell suspension at $2.5\times10^6$ cells/mL. This was followed by pipetting 10 μL drops of the suspension to the inside of a petri dish lid which was then placed on the petri dish containing 5 mL of PBS to provide moisture and to prevent desiccation of the cell suspension. With no drug treatment, the cells gravitated to the bottom of the hanging 10 μL drop and created a tight 3D spheroid aggregate, due to formation of bonds between N-cadherin receptors. Increasing the amount of drug led to looser aggregates, or even to an unconnected monolayer sheet of cells with no cell-cell cohesiveness, due to inhibition of cadherin bond formation.

Figure 6:
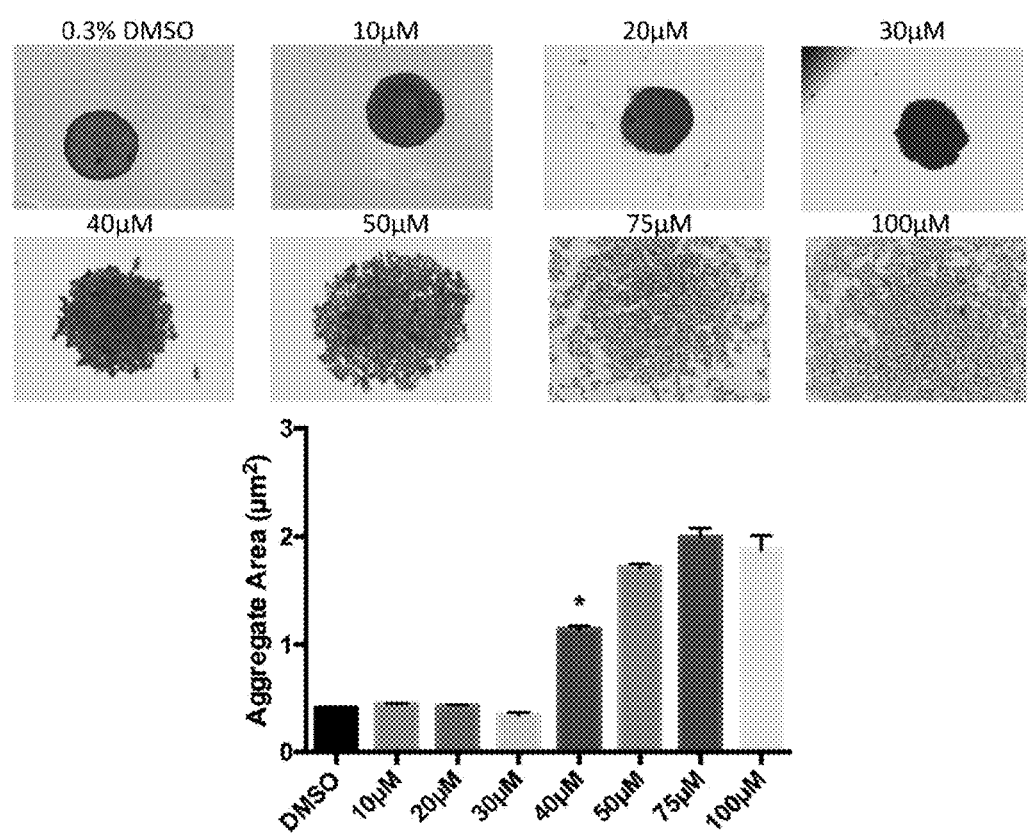
FIG. 6 illustrates the ability of a cell adhesion antagonist Compound 15 (FIG. 2C) to disrupt N-cadherin-mediated cell adhesion, as shown as shown in a hanging drop cell culture assay.
Figure 7:
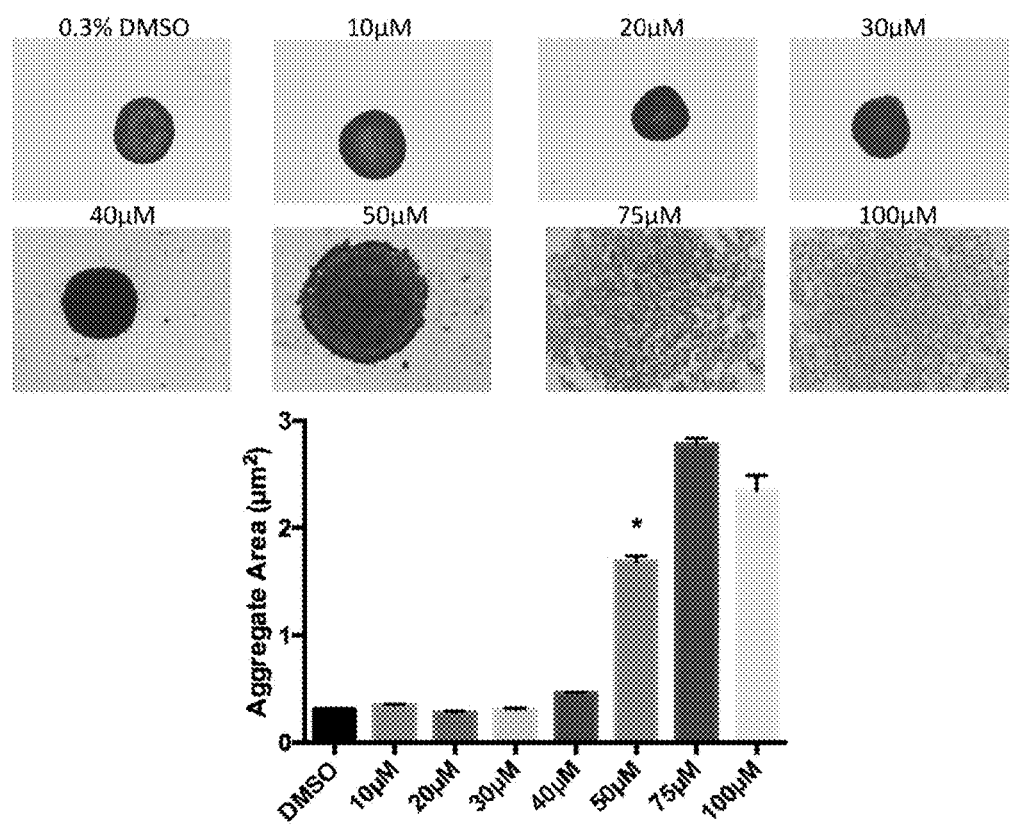
FIG. 7 illustrates the ability of a cell adhesion antagonist Compound 16 (FIG. 2C) to disrupt N-cadherin-mediated cell adhesion, as shown as shown in a hanging drop cell culture assay.

The minimum concentration required to observe cohesion disruption for compound 15 was 40 μM. Complete disruption occurred at 75 μM (FIG. 6). The minimum concentrations required to observe cohesion disruption for drug compound 16 was 50 μM. Complete disruption occurred at 75 μM (FIG. 7). All compounds were considered effective when the average aggregate diameter reached approximately 1.5 μm².

Examples 6-16: Synthesis Schemes

Compounds of the present teachings can be prepared according to the reaction schemes in the examples illustrated below utilizing methods known to one of ordinary skill in the art. These schemes serve to exemplify some procedures that can be used to make the compounds of the present teachings. One skilled in the art will recognize that other general synthetic procedures can be used. The compounds of the present teachings can be prepared from starting components that are commercially available. Any kind of substitutions can be made to the starting components to obtain the compounds of the present teachings according to procedures that are well known to those skilled in the art. All reagents and solvents were obtained from commercial sources and used as received. $^1$H-NMR spectra were recorded on a Bruker 500 MHz Ultrashield instrument with Bruker Avance II 500 Console in the solvents indicated. Low resolution mass-spectra (LRMS) were acquired on an AGILENT® MSD instrument. Analytical HPLC was performed on an AGILENT® 1100 instrument using Kinetex 2.6 C18 100 Å, 30×4.6 mm column; eluting with methanol/water containing 0.05% formic acid, with a gradient 5-95% of methanol over 3 minutes. Flash column chromatography was performed using silica gel (40-63 μM, pore size 60 Å, SILICYCLE®).

Example 6

This example illustrates synthesis of Compound 2.

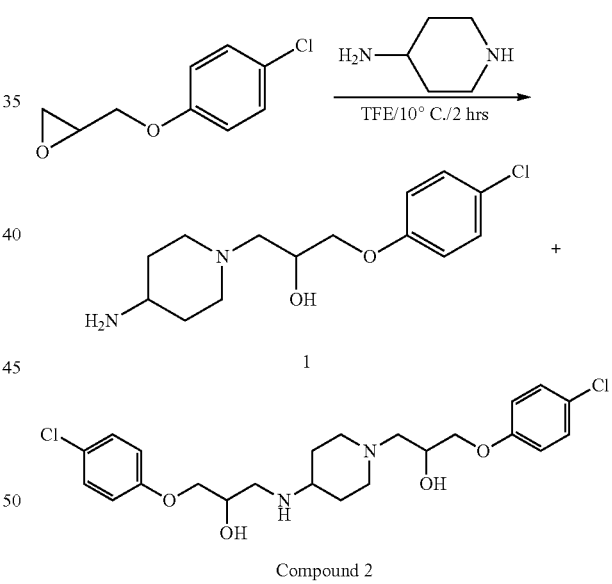

1-(4-Aminopiperidin-1-yl)-3-(4-chlorophenoxy)propan-2-ol (1) and 1-(4-chlorophenoxy)-3-(1-(3-(4-chlorophenoxy)-2-hydroxypropyl)piperidin-4-ylamino)propan-2-ol (2)

A solution of 2-((4-chlorophenoxy)methyl)oxirane (368 mg, 2 mmol) in trifluoroethanol (TFE, 3 mL) at 5-10° C. was treated with piperidin-4-amine (200 mg, 2 mmol). The mixture was stirred for 2 hrs at the same temperature then for 1 hr at ambient temperature. The reaction mixture was evaporated and the remaining oil was subjected to flash column chromatography (eluent 20% MeOH in DCM, MeOH contained 2% ammonia), to afford compound 1 (more polar, 289 mg, 51% yield) and compound 2 (less polar, 100 mg, 11% yield).

Compound 1: ¹H NMR (500 MHz, DMSO-d$_6$) δ(ppm): 7.31 (d, J=9.1 Hz, 2H), 6.96 (d, J=9.1 Hz, 2H), 4.79 (d, J=4.5 Hz, 1H), 3.96 (dd, J=3.4 and 9.7 Hz, 1H), 3.89 (bs, 1H), 3.83 (dd, J=6.1 and 9.7 Hz, 1H), 2.80 (d, J=11.5 Hz, 1H), 2.75 (d, J=1.0 Hz, 1H), 2.50-2.45 (m, 1H), 2.38 (dd, J=6.3 and 12.6 Hz, 1H), 2.30 (dd, J=6.3 and 12.6 Hz, 1H), 2.02 (dd, J=2.6 and 11.8 Hz, 1H), 1.97 (dd, J=2.5 and 11.6 Hz, 1H), 1.64-1.61 (m, 2H), 1.44 (bs, 2H), 1.24-1.16 (m, 2H). (MS) (mass-to-charge ratio; m/z): 285.2 (M+H). (CRS-00-019)

Compound 2: ¹H NMR (500 MHz, CDCl$_3$) δ(ppm): 7.24-7.21 (m, 4H), 6.85-6.81 (m 4H), 4.20-4.14 (m, 1H), 4.11-4.06 (m, 1H), 3.99-3.91 (m, 4H), 3.06-3.01 (m, 2H), 2.92-2.85 (m, 2H), 2.74-2.68 (m, 1H), 2.60-2.50 (m, 2H), 2.38 (t, J=11.4 Hz, 1H), 2.12 (t, J=12.1 Hz, 1H), 2.02 (d, J=11.7 Hz, 2H), 1.67-1.57 (m, J=2H), [signals corresponding to NH and OH protons are not seen]. (MS) (mass-to-charge ratio; m/z): 469.3 (M+H). (CRS-00-020)

Example 7

This example illustrates synthesis of Compound 4.

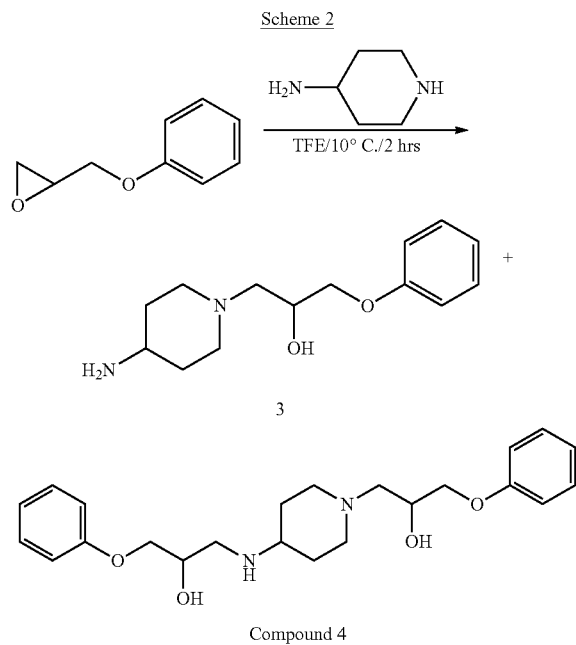

Compound 4

1-(4-aminopiperidin-1-yl)-3-phenoxypropan-2-ol (3) and 1-(1-(2-hydroxy-3-phenoxypropyl)piperidin-4-ylamino)-3-phenoxypropan-2-ol (4)

Compounds 3 and 4 were obtained according to the scheme 2 in 45% and 16% yields, respectively by following the procedures described above for the synthesis of compounds 1 and 2 (scheme 1) by replacing the 2-((4-chlorophenoxy)methyl)oxirane with 2-(phenoxymethyl)oxirane.

Compound 3: ¹H NMR (500 MHz, DMSO-d$_6$) δ(ppm): 7.29-7.25 (m, 2H), 6.94-6.90 (m, 3H), 4.76 (bs, 1H), 3.95 (dd, J=3.7 and 9.6 Hz, 1H), 3.90 (m, 1H), 3.83 (dd, J=6.0 and 9.6 Hz, 1H), 2.93-2.80 (m, 1H), 2.77-2.74 (m, 1H), 2.50-2.46 (m, 1H), 2.40 (dd, J=6.2 and 12.7 Hz, 1H), 2.31 (dd, J=6.4 and 12.6 Hz, 1H), 2.03-1.96 (m, 2H), 1.66-1.60 (m, 2H), 1.55 (bs, 2H), 1.25-1.17 (m, 2H). (MS) (mass-to-charge ratio; m/z): 251.3 (M+H). (CRS-00-023)

Compound 4: ¹H NMR (500 MHz, CDCl$_3$) δ(ppm): 7.31-7.26 (m, 4H), 6.98-6.90 (m 6H), 4.11-4.04 (m, 2H), 4.02-3.95 (m, 4H), 3.04-3.01 (m, 1H), 2.97-2.94 (m, 1H), 2.88-2.85 (m, 1H), 2.80 (dd, J=7.8 and 12.1 Hz, 1H), 2.61-2.51 (m, 3H), 2.38 (t, J=11.8 Hz, 1H), 2.11 (t, J=11.4 Hz, 1H), 1.97-1.93 (m, J=2H), 1.53-1.42 (m, 2H). [signals corresponding to NH and OH protons are not seen]. (MS) (mass-to-charge ratio; m/z): 401.5 (M+H). (CRS-00-014)

Example 8

This example illustrates synthesis of Compound 5.

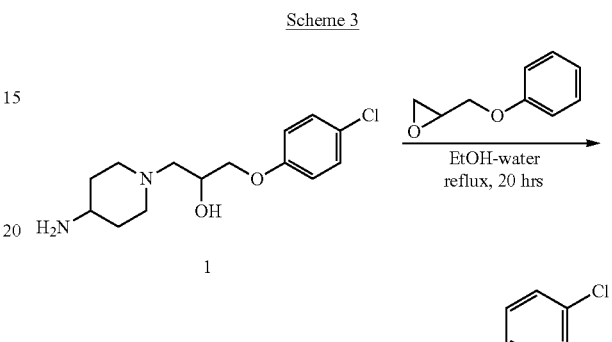

Compound 5

1-(4-Chlorophenoxy)-3-(4-(2-hydroxy-3-phenoxypropylamino)piperidin-1-yl)propan-2-ol (5)

To a solution of the compound 1 (178 mg, 0.62 mmol) in 70% aqueous EtOH (8 mL) at RT was added the 2-(phenoxymethyl)oxirane (94 mg, 0.62 mmol). The reaction mixture was heated to reflux for 20 hrs, cooled to RT evaporated. The remaining oil was purified by flash column chromatography (eluent 20% MeOH in DCM, MeOH contained 2% ammonia) to afford compound 5 as oily material that has turned into a white solid in vacuum. Yield: 176 mg (65%). ¹H NMR (500 MHz, CD$_3$OD) δ(ppm): 7.31-7.26 (m, 4H), 6.98-6.94 (m 5H), 4.14-4.06 (m, 2H), 4.03-3.98 (m, 3H), 3.94 (dd, J=5.9 and 9.8 Hz, 1H), 3.07-3.04 (m, 2H), 2.92 (dd, J=3.8 and 12.1 Hz, 1H), 2.77 (dd, J=8.4 and 12.1 Hz, 1H), 2.62-2.52 (m, 3H), 2.25-2.17 (m, 2H), 1.95 (bs, 2H), 1.55-1.46 (m, 2H). [Signals corresponding to NH and OH protons are not seen]. (MS) (mass-to-charge ratio; m/z): 434.9 (M+H). (CRS-00-026)

Example 9

This example illustrates synthesis of Compound 6.

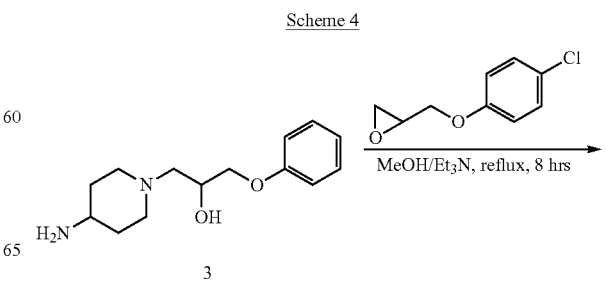

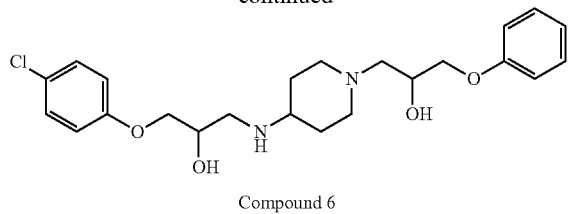

Compound 6

1-(4-Chlorophenoxy)-3-(1-(2-hydroxy-3-phenoxypropyl)piperidin-4-ylamino)propan-2-ol (6)

To a solution of the compound 3 (221 mg, 0.88 mmol) in MeOH (5 mL) at RT was added the 2-((4-chlorophenoxy)methyl)oxirane (163 mg, 0.88 mmol) followed by TEA (89 mg, 0.88 mmol). The reaction mixture was heated to reflux for 8 hours, evaporated and the remaining oil was purified by flash column chromatography (eluent 20% MeOH in DCM, MeOH contained 2% ammonia) to afford a glassy solid which was re-dissolved in DCM and treated with excess hexanes. A white precipitate was collected by filtration and dried to afford compound 6. Yield: 175 mg (45%). $^1$H NMR (500 MHz, DMSO-$d_6$) δ(ppm): 7.32-7.25 (m, 4H), 6.97-6.89 (m, 5H), 4.99 (bs, 1H), 4.77 (bs, 1H), 3.97-3.80 (m, 6H), 2.84 (d, J=11.5 Hz, 1H), 2.79 (d, J=12.0 Hz, 1H), 2.68 (dd, J=4.9 and 11.8 Hz, 1H), 2.58 (dd, J=6.6 and 11.8 Hz, 1H), 2.43-2.30 (m, 3H), 2.05-1.98 (m, 2H), 1.75 (bs, 2H), 1.27-1.20 (m, 2H). [Signal corresponding to the NH proton is not seen]. (MS) (mass-to-charge ratio; m/z): 435.3 (M+H). (CRS-00-024)

Example 10

This example illustrates synthesis of Compound 7.

A solution of compound 4 (130 mg, 0.33 mmol) in a mixture of DCE (5 mL) and MeOH (2 mL) was treated with a 37% aqueous formaldehyde solution (30 μL, 0.36 mmol) at RT. The reaction mixture was stirred for 1 hour then treated with sodium triacetoxyborohydride (280 mg, 1.32 mmol). The reaction mixture was stirred for 3 hrs at RT, diluted with DCM and washed with a mixture of a saturated NaHCO$_3$ solution and 0.5 M NaOH solution (pH 9.5-10.5) then brine. The solution was then dried over anhydrous MgSO$_4$, filtered and concentrated. The crude product was purified by flash column chromatography using 20% MeOH in DCM as eluent (MeOH contained 2% ammonia) to afford compound 7 (83 mg, 61% yield). $^1$H NMR (500 MHz, DMSO-$d_6$) δ(ppm): 7.29-7.25 (m, 4H), 6.94-6.89 (m, 6H), 4.79 (bs, 2H), 3.98-3.82 (m, 6H), 2.94 (d, J=11.2 Hz, 1H), 2.89 (d, J=10.5 Hz, 1H), 2.57-2.53 (m, 1H), 2.44-2.38 (m, 2H), 2.35-2.28 (m, 2H), 2.24 (s, 3H), 1.98 (t, J=10.5 Hz, 2H), 1.62 (t, J=15.1 Hz, 2H), 1.47-1.39 (m, 2H). (MS) (mass-to-charge ratio; m/z): 415.4 (M+H). (CRS-00-025)

Example 11

This example illustrates synthesis of Compound 10.

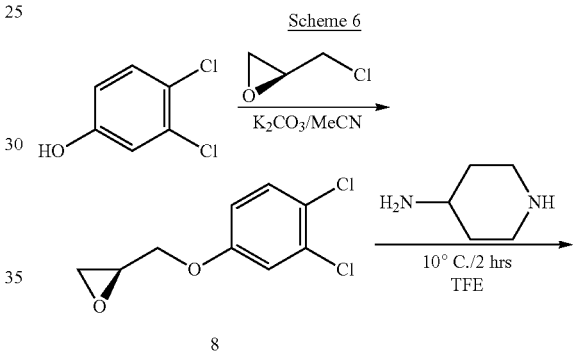

Scheme 6

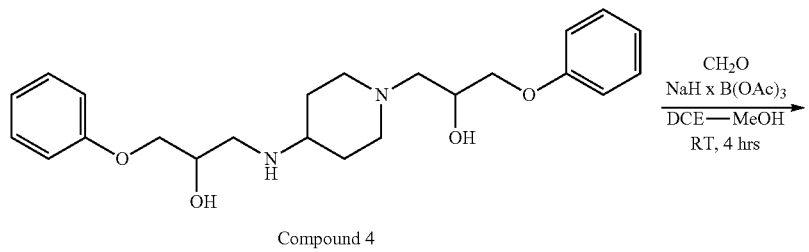

Scheme 5

Compound 4

Compound 7

1-(4-((2-Hydroxy-3-phenoxypropyl)(methyl)amino)piperidin-1-yl)-3-phenoxypropan-2-ol (7)

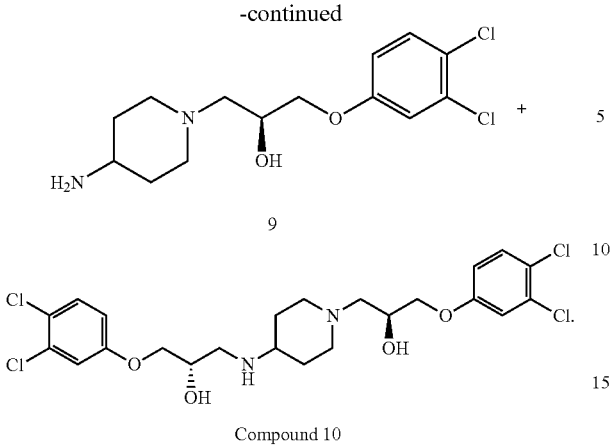

Compound 10

(S)-1-(4-Aminopiperidin-1-yl)-3-(3,4-dichlorophenoxy)propan-2-ol (9) and (S)-1-(3,4-dichlorophenoxy)-3-(4-(((S)-3-(3,4-dichlorophenoxy)-2-hydroxypropyl)amino)piperidin-1-yl)propan-2-ol (10)

Step 1. (S)-2-((3,4-Dichlorophenoxy)methyl)oxirane (8)

To a solution of 3,4-dichlorophenol (2.27 g, 14 mmol) in MeCN (50 mL) was added (S)-2-(chloromethyl)oxirane (2.78 g, 30 mmol) and potassium carbonate (5.56 g, 40 mmol). The reaction mixture was stirred for 14 hrs at reflux conditions, filtered and the filtrate was evaporated. The remaining oil was purified by flash column chromatography, eluent 20% EA in hexanes to afford compound 8 (2.20 g, 72% yield) as a yellow oil. $^1$H NMR (500 MHz, CDCl$_3$) δ(ppm): 7.33 (d, J=8.9 Hz, 1H), 7.02 (d, J=2.9 Hz, 1H), 6.79 (dd, J=2.0 and 8.9 Hz, 1H), 4.23 (dd, J=2.9 and 11.0 Hz, 1H), 3.90 (dd, J=5.8 and 11.0 Hz, 1H), 3.35-3.32 (m, 1H), 2.91 (dd, J=4.2 and 4.8 Hz, 1H), 2.75 (dd, J=2.6 and 4.9 Hz, 1H)

Step 2. (S)-1-(4-Aminopiperidin-1-yl)-3-(3,4-dichlorophenoxy)propan-2-ol (9) and (S)-1-(3,4-dichlorophenoxy)-3-(4-(((S)-3-(3,4-dichlorophenoxy)-2-hydroxypropyl)amino)piperidin-1-yl)propan-2-ol (10)

A solution of compound 8 (438 mg, 2 mmol) in 4 mL TFE at 5-10° C. was treated with a solution of piperidin-4-amine (200 mg, 2 mmol) in 1 mL of TFE. The mixture was stirred at the same temperature for 2 hrs then for 1 hr at ambient temperature. The reaction mixture was evaporated and the remaining oil was subjected to flush column chromatography (eluent 20% MeOH in DCM, MeOH contained 2% ammonia) to afford compound 9 (more polar, 440 mg, 69% yield) and compound 10 (less polar, 147 mg, 14% yield).

Compound 9: $^1$H NMR (500 MHz, DMSO-d$_6$) δ(ppm): 7.50 (d, J=8.9 Hz, 1H), 7.23 (d, J=2.9 Hz, 1H), 6.97 (dd, J=2.9 and 8.9 Hz, 1H), 4.83 (bs, 1H), 4.03-3.99 (m, 1H), 3.91-3.86 (m, 2H), 2.82-2.79 (m, 1H), 2.76-2.73 (m, 1H), 2.50-2.45 (m, 1H), 2.39-2.35 (m, 1H), 2.31-2.27 (m, 1H), 2.03-1.95 (m 2H), 1.66-1.60 (m, 2H), 1.25-1.17 (m, 2H). [Signals corresponding to the NH$_2$-protons are not seen]. (MS) (mass-to-charge ratio; m/z): 319.1 (M+H). (CRS-00-027)

Compound 10: $^1$H NMR (500 MHz, DMSO-d$_6$) δ(ppm): 7.51 (d, J=0.4 Hz, 1H), 7.49 (d, J=0.4 Hz, 1H), 7.23 (t, J=3.1 Hz, 2H), 6.97 (dd, J=1.9 and 2.9 Hz, 1H), 6.96 (dd, J=2.0 and 2.9 Hz, 1H), 5.03 (bs, 1H), 4.94 (bs, 1H), 4.03-3.99 (m, 2H), 3.91-3.67 (m, 3H), 3.84-3.81 (m, 1H), 2.84 (d, J=11.6 Hz, 1H), 2.78 (d, J=11.4 Hz, 1H), 2.68 (dd, J=5.0 and 11.9 Hz, 1H), 2.59 (dd, J=6.9 and 11.8 Hz, 1H), 2.40-2.37 (m, 2H), 2.31 (dd, J=5.7 and 12.5 Hz, 1H), 2.06-1.98 (m, 2H), 1.77-1.74 (m, 2H), 1.28-1.22 (m, 2H). [Signal of NH-proton is not seen]. (MS) (mass-to-charge ratio; m/z): 538.9 (M+H). (CRS-00-028)

Example 12

This example illustrates synthesis of Compound 13.

Scheme 7

Compound 13

(R)-1-(4-Aminopiperidin-1-yl)-3-(3,4-dichlorophenoxy)propan-2-ol (12) and (R)-1-(3,4-dichlorophenoxy)-3-(1-((R)-3-(3,4-dichlorophenoxy)-2-hydroxypropyl)piperidin-4-ylamino)propan-2-ol (13).

Step 1. (R)-2-((3,4-Dichlorophenoxy)methyl)oxirane (11)

To a solution of 3,4-dichlorophenol (2.27 g, 20 mmol) in MeCN (50 mL) was added (R)-2-(chloromethyl)oxirane (2.78 g, 30 mol) and potassium carbonate (5.56 g, 40 mmol). The reaction mixture was stirred for 14 hrs at reflux conditions, filtered and the filtrate was evaporated. The remaining oil was purified by flash column chromatography, eluent 20% EA in hexanes to afford compound 11 (2.10 g, 69% yield) as a yellow oil. $^1$H NMR (500 MHz, CDCl$_3$) δ(ppm): 7.33 (d, J=8.9 Hz, 1H), 7.02 (d, J=2.9 Hz, 1H), 6.79 (dd, J=2.0 and 8.9 Hz, 1H), 4.23 (dd, J=2.9 and 11.0 Hz, 1H), 3.90 (dd, J=5.8 and 11.0 Hz, 1H), 3.35-3.32 (m, 1H), 2.91 (dd, J=4.2 and 4.8 Hz, 1H), 2.75 (dd, J=2.6 and 4.9 Hz, 1H)

Step 2. (R)-1-(4-Aminopiperidin-1-yl)-3-(3,4-dichlorophenoxy)propan-2-ol (12) and (R)-1-(3,4-dichlorophenoxy)-3-(1-((R)-3-(3,4-dichlorophenoxy)-2-hydroxypropyl)piperidin-4-ylamino)propan-2-ol (13)

A solution of compound 11 (518 mg, 2.37 mmol) in 4 mL TFE at 5-10° C. was treated with a solution of piperidin-4-amine (237 mg, 2.37 mmol) in 1 mL of TFE. The mixture was stirred at the same temperature for 2 hrs then for 1 hr at ambient temperature. The reaction mixture was evaporated and the remaining oil was subjected to flash column chromatography (eluent 20% MeOH in DCM, MeOH contained 2% ammonia) to afford compound 12 (more polar, 500 mg, 66% yield) and compound 13 (less polar, 150 mg, 12% yield).

Compound 12: $^1$H NMR (500 MHz, DMSO-$d_6$) δ(ppm): 7.50 (d, J=8.9 Hz, 1H), 7.23 (d, J=2.9 Hz, 1H), 6.97 (dd, J=2.9 and 8.9 Hz, 1H), 4.83 (bs, 1H), 4.03-3.99 (m, 1H), 3.91-3.86 (m, 2H), 2.83-2.79 (m, 1H), 2.76-2.73 (m, 1H), 2.50-2.45 (m, 1H), 2.39-2.35 (m, 1H), 2.31-2.27 (m, 1H), 2.04-1.95 (m 2H), 1.66-1.60 (m, 2H), 1.25-1.17 (m, 2H). [Signals of NH$_2$ protons are not seen]. (MS) (mass-to-charge ratio; m/z): 319.04 (M+H). (CRS-00-030)

Compound 13: $^1$H NMR (500 MHz, DMSO-$d_6$) δ(ppm): 7.51 (d, J=1.5 Hz, 1H), 7.50 (d, J=1.5 Hz, 1H), 7.24-7.23 (m, 2H), 6.97 (dd, J=1.4 and 2.9 Hz, 1H), 6.96 (dd, J=1.4 and 2.9 Hz, 1H), 5.08 (bs, 1H), 4.85 (bs, 1H), 4.03-4.00 (m, 2H), 3.92-3.81 (m, 4H), 2.85 (bd, J=10.9 Hz, 1H), 2.79 (d, J=11.1 Hz, 1H), 2.72-2.69 (m, 1H), 2.64-2.59 (m, 1H), 2.43-2.36 (m, 2H), 2.33-2.29 (m, 1H), 2.06-1.98 (m, 2H), 1.77 (bd, J=10.2 Hz, 2H), 1.30-1.23 (m, 2H) [Signal of NH-proton is not seen]. (MS) (mass-to-charge ratio; m/z): 538.9 (M+H). (CRS-00-031)

Example 13

This example illustrates synthesis of Compound 15.

Step 1. (S)-2-((4-Methoxyphenoxy)methyl)oxirane (14)

To a solution of 4-methoxyphenol (2.48 g, 20 mmol) in MeCN (50 mL) was added (S)-2-(chloromethyl)oxirane (8.37 g, 90 mol) and potassium carbonate (8.28 g, 60 mmol). The reaction mixture was stirred for 72 hrs at reflux conditions, filtered and the filtrate was evaporated. The remaining oil was purified by flash column chromatography, eluent 20% EA in hexanes to afford compound 14 (2.47 g, 69% yield) as colorless oil that has solidified in vacuum. $^1$H NMR (500 MHz, CDCl$_3$) δ(ppm): 6.87 (d, J=9.4 Hz, 2H), 6.83 (d, J=9.4 Hz, 2H), 4.17 (dd, J=3.2 and 11.0 Hz, 1H), 3.92 (dd, J=5.6 and 11.0 Hz, 1H), 3.77 (s, 3H), 3.35-3.32 (m, 1H), 2.89 (dd, J=4.2 and 4.9 Hz, 1H), 2.74 (dd, J=2.7 and 5.0 Hz, 1H)

Step 2. (S)-1-(3,4-Dichlorophenoxy)-3-(4-((S)-2-hydroxy-3-(4-methoxyphenoxy)propylamino)piperidin-1-yl)propan-2-ol (15)

To a solution of the compound 9 (190 mg, 0.60 mmol) in 70% aqueous EtOH (10 mL) at RT was added the oxirane 14 (107 mg, 0.60 mmol). The reaction mixture was heated to reflux for 20 hrs, cooled to RT evaporated. The remaining oil was purified by flash column chromatography (eluent 20% MeOH in DCM, MeOH contained 2% ammonia) to afford compound 15 as oily material that turned into a white solid in vacuum. Yield: 196 mg (66%). $^1$H NMR (500 MHz, DMSO-$d_6$) δ(ppm): 7.50 (d, J=8.9 Hz, 1H), 7.23 (d, J=2.9 Hz, 1H), 6.97 (dd, J=2.9 and 8.9 Hz, 1H), 6.87-6.83 (m, 4H), 5.01 (bs, 1H), 4.85 (bs, 1H), 4.01-3.99 (m, 1H), 3.91-3.79 (m, 5H), 3.69 (s, 3H), 2.87-2.72 (m, 3H), 2.62-2.59 (m, 1H), 2.50-2.29 (m, 3H), 2.06-1.98 (m, 2H), 1.77 (bd, 2H), 1.30-1.23 (m, 2H). [Signal of NH proton is not seen]. (MS) (mass-to-charge ratio; m/z): 500.0 (M+H). (CRS-00-029)

Example 14

This example illustrates synthesis of Compound 16.

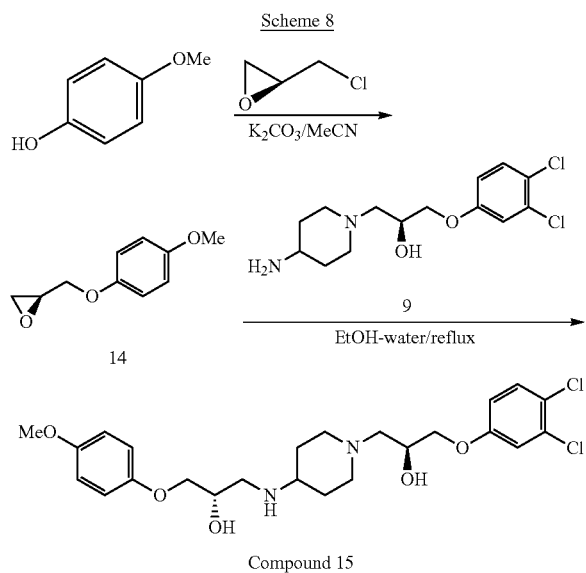

Compound 15

(S)-1-(3,4-Dichlorophenoxy)-3-(4-((S)-2-hydroxy-3-(4-methoxyphenoxy)propylamino)piperidin-1-yl)propan-2-ol (15).

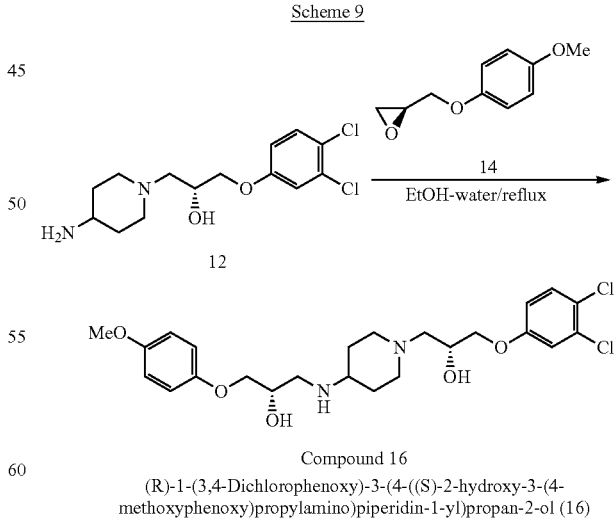

Compound 16

(R)-1-(3,4-Dichlorophenoxy)-3-(4-((S)-2-hydroxy-3-(4-methoxyphenoxy)propylamino)piperidin-1-yl)propan-2-ol (16)

To a solution of the compound 12 (234 mg, 0.73 mmol) in 70% aqueous EtOH (10 mL) at RT was added the oxirane 14 (132 mg, 0.73 mmol). The reaction mixture was heated to reflux for 20 hrs, cooled to RT and evaporated. The remaining oil was purified by flash column chromatography (eluent 20% MeOH in DCM, MeOH contained 2% ammonia) to afford the compound 16 as oily material that turned into a white solid in vacuum. Yield: 156 mg (42%). $^1$H NMR (500 MHz, DMSO-d$_6$) δ(ppm): 7.50 (d, J=8.9 Hz, 1H), 7.23 (d, J=2.9 Hz, 1H), 6.97 (dd, J=2.9 and 8.9 Hz, 1H), 6.87-6.82 (m, 4H), 4.98 (bs, 1H), 4.85 (bs, 1H), 4.01-3.99 (m, 1H), 3.89-3.78 (m, 5H), 3.68 (s, 3H), 2.86-2.70 (m, 3H), 2.61-2.57 (m, 1H), 2.41-2.37 (m, 2H), 2.33-2.29 (m, 1H), 2.06-1.98 (m, 2H), 1.76 (bt, 2H), 1.30-1.23 (m, 2H). [Signal of NH-proton is not seen]. (MS) (mass-to-charge ratio; m/z): 499.0 (M+H). (CRS-00-032)

Example 15

This example illustrates synthesis of Compound 18.

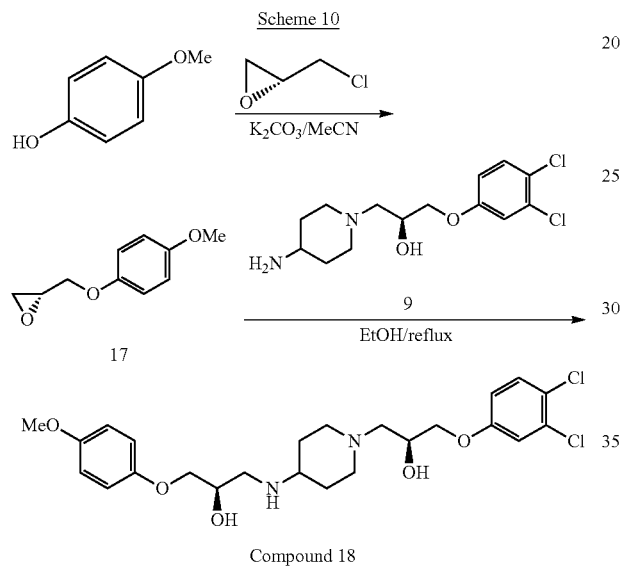

Scheme 10

Compound 18

(S)-1-(3,4-Dichlorophenoxy)-3-(4-((R)-2-hydroxy-3-(4-methoxyphenoxy)propylamino)piperidin-1-yl)propan-2-ol (18).

Step 1. (R)-2-((4-Methoxyphenoxy)methyl)oxirane (17)

To a solution of 4-methoxyphenol (2.48 g, 20 mmol) in MeCN (50 mL) was added (R)-2-(chloromethyl)oxirane (8.37 g, 90 mol) and potassium carbonate (8.28 g, 60 mmol). The reaction mixture was stirred for 30 hrs at reflux conditions, filtered and the filtrate was evaporated. The remaining oil was purified by flash column chromatography, eluent 20% EA in hexanes to afford compound 17 (2.87 g, 80% yield) as colorless oil that solidified in vacuum. $^1$H NMR (500 MHz, CDCl$_3$) δ(ppm): 6.87 (d, J=9.4 Hz, 2H), 6.83 (d, J=9.4 Hz, 2H), 4.17 (dd, J=3.2 and 11.0 Hz, 1H), 3.92 (dd, J=5.6 and 11.0 Hz, 1H), 3.77 (s, 3H), 3.35-3.32 (m, 1H), 2.89 (dd, J=4.2 and 4.9 Hz, 1H), 2.74 (dd, J=2.7 and 5.0 Hz, 1H).

Step 2. (S)-1-(3,4-Dichlorophenoxy)-3-(4-((R)-2-hydroxy-3-(4-methoxyphenoxy)propylamino)piperidin-1-yl)propan-2-ol (18)

To a solution of the compound 9 (145 mg, 0.45 mmol) in EtOH (7 mL) was added the oxirane 17 (82 mg, 0.45 mmol). The reaction mixture was heated to reflux for 20 hrs, cooled to RT evaporated. The remaining oil was purified by flash column chromatography (eluent 20% MeOH in DCM, MeOH contained 2% ammonia) to afford the compound 18 as oily material that turned into a white solid in vacuum. Yield: 8 mg (4%). $^1$H NMR (500 MHz, CD$_3$OD) δ(ppm): 7.43 (d, J=8.9 Hz, 1H), 7.17 (d, J=2.9 Hz, 1H), 6.98-6.86 (m, 5H), 4.20-4.12 (m, 2H), 4.06-3.95 (m, 4H), 3.77 (s, 3H), 3.21-3.14 (m, 3H), 3.06-2.99 (m, 2H), 2.69-2.60 (m, 2H), 2.34-2.27 (m, 2H), 2.11-2.06 (m, 2H), 1.74-1.65 (m, 2H). [Signals of OH and NH protons are not seen]. (MS) (mass-to-charge ratio; m/z): 498.8 (M+H). (CRS-00-064)

Example 16

This example illustrates the synthesis of Compound 19.

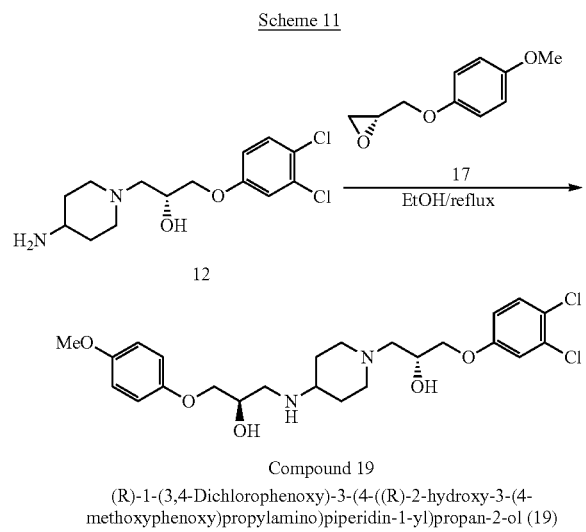

Scheme 11

Compound 19

(R)-1-(3,4-Dichlorophenoxy)-3-(4-((R)-2-hydroxy-3-(4-methoxyphenoxy)propylamino)piperidin-1-yl)propan-2-ol (19)

To a solution of the compound 12 (190 mg, 0.60 mmol)) in EtOH (10 mL) at RT was added the oxirane 17 (108 mg, 0.60 mmol). The reaction mixture was heated to reflux for 4 hrs, cooled to RT evaporated. The remaining oil was purified by flash column chromatography (eluent 20% MeOH in DCM, MeOH contained 2% ammonia) to afford the compound 19 as oily material that turned into a white solid in vacuum. Yield: 163 mg (55%). $^1$H NMR (500 MHz, CD$_3$OD) δ(ppm): 7.41 (d, J=8.9 Hz, 1H), 7.16 (d, J=2.9 Hz, 1H), 6.94-6.84 (m, 5H), 4.13-4.02 (m, 3H), 3.95-3.93 (m, 3H), 3.76 (s, 3H), 3.05-2.98 (m, 2H), 2.90 (dd, J=3.8 and 12.1 Hz, 1H), 2.74 (dd, J=8.4 and 12.0 Hz, 1H), 2.59-2.50 (m, 3H), 2.22-2.15 (m, 2H), 1.94-1.92 (m, 2H), 1.54-1.45 (m, 2H). [OH and NH protons are not seen]. (MS) (mass-to-charge ratio; m/z): 498.9 (M+H). (CRS-00-065)

Example 17

This example illustrates the effects of Compound 15 on N-cadherin-mediated cancer-associated fibroblast viability.

Previous studies have shown that pancreatic tumors can be composed of 90% stromal cells (Olive et al., Science 1061:324:1457-1461, 2009; Olive, Clin Cancer Res 21:3366-3368, 2015). Cancer-associated fibroblasts (CAFs) are one of the major cell types present in the tumor stroma (reviewed by Pandol et al., Clin Gastroenterol Hepatol 7:S44-S47, 2009; Karagiannis et al., Mol Cancer Res 10:1403-1418 2012, Joyce and Fearon 2015). They aggregate peritumorally and encircle cancer cells invading adjacent normal tissues. CAFs support pancreatic cancer (PC) cell survival and protect these cells from attack by the immune system (Joyce and Fearon, Science 348:74-80, 2015), as well as prevent access of anti-cancer drugs to the PC cells (Olive et al., Science 1061:324:1457-1461, 2009).

In this study, CAFs were isolated as described by Orr et al, (Orr, B., et al., Oncogene, 31, 1130-1142, 2012). The cells were grown in Dulbecco's modified Eagle medium (Multicell) with 10% fetal bovine serum. CAFs are human primary fibroblasts, grown from patient prostate tumor samples. These cells are not an established cell line, nor are they immortalized, and at some point they will senesce.

Figure 8:
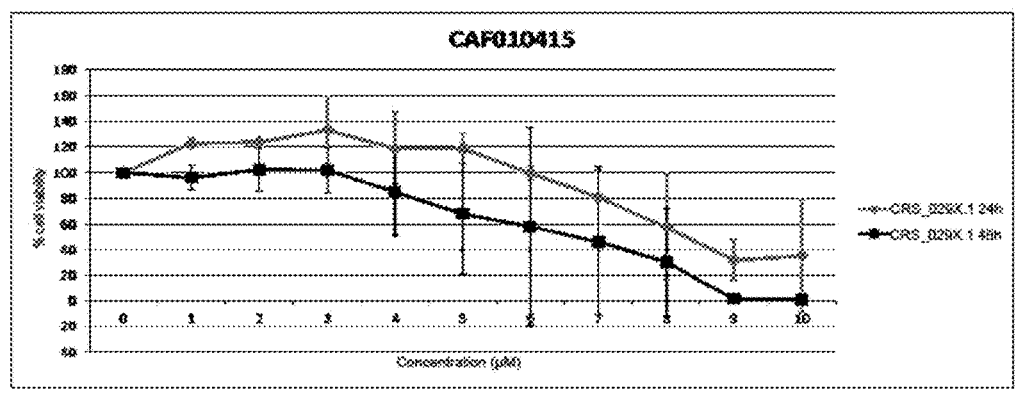
FIG. 8 illustrates that the N-cadherin antagonist Compound 15 decreases human cancer-associated fibroblast (CAF010415) viability in vitro.

In these experiments, cells were seeded in a 96-well plate (Corning) (3,000 cells/well). The next day, the drug was added at the indicated concentration (FIG. 8). After 24 h and 48 h cell viability was measured using CELLTITER GLO® (Promega, Madison, Wis.) according to the manufacturer's protocol. All assays were repeated at least 3 times in triplicate each time. The results are depicted in FIG. 8 as SEM. The data indicate that N-cadherin antagonist compound 15 decreases human cancer-associated fibroblast (CAF010415) viability in vitro (FIG. 8). The N-cadherin antagonist compound 15 thus decreases the viability of human pancreatic cancer (PC) cells and CAFs. These observations indicate that N-cadherin antagonists can be used to treat PC.

Example 18

This example demonstrates the effects of the N-cadherin antagonist compound 15 on human fibroblast-like synoviocytes (FLS).

Fibroblast-like synoviocytes (FLS) are a new cellular target for treating rheumatoid arthritis (RA). FLS express N-cadherin (Agarwal, S. K., et al., Arthritis Rheum., 58, 1044-1054, 2008). N-cadherin regulates FLS adhesion.

Figure 9:
FIG. 9 illustrates the disruption of cell adhesion in FLS cells by increasing concentrations of Compound 15.

In these experiments, human fibroblast-like synoviocytes (FLS) (ScienCell Research Laboratories (Carlsbad, Calif.; Cat#4700) were maintained in complete Synoviocyte media (ScienCell Research Laboratories Carlsbad, Calif. Cat#4701) at 37° C. in 5% $CO_2$ in air. FLS cells were plated at $1.5 \times 10^4$ cells per well of a 4-well tissue culture slide (NalgeNunc, Naperville, Ill.). After 24 hours of culture, cells were treated for 24 hours with medium containing varying concentrations of compounds 15 dissolved in dimethylsulfoxide (DMSO; final concentration of 1% DMSO in the medium), or 1% DMSO alone in the medium. The cells were then fixed with 4% paraformaldehyde dissolved in phosphate buffered saline and stained with hematoxylin. Disruption of cell adhesion was determined visually within 24 hours, by observing retraction of the cells from one another. FIG. 9 shows treated FLS cells photographed at 400×. As shown in FIG. 9, effects of Compound 15 on FLS cells can be seen in the range of 5-50 µM. These results show that Compound 15 can be used to treat RA.

Example 19

There is an unmet need for non-hormonal contraceptives. Women with an unmet need for family planning are defined as the percentage of women of reproductive age (15-49), either married or in a union, who want to stop or delay childbearing but are not using any method of contraception (United Nations Department of Economic and Social Affairs, Population Division). In 2017, the unmet need for contraception among women of reproductive age was 21.6%, and only 67.9% of the population was satisfied with modern methods (Cahill, N., et al., Lancet, 391, 870-882, 2018).

This example illustrates that Compound 15 inhibits corpus luteum formation.

Figure 10:
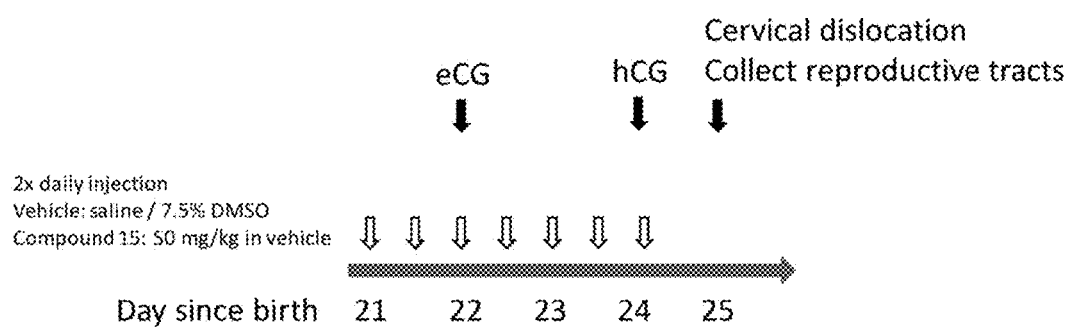
FIG. 10 is a schematic showing the injection of hormones into mice to cause follicle maturation and injection of Compound 15.

In these experiments, two groups of female mice (n=6 per group) were injected i.p. (50 µL per injection) twice per day with either vehicle control (saline containing 7.5% DMSO) or vehicle containing compound 15 (50 mg/kg) at the days indicated in FIG. 10. The mice were injected with hormones to stimulate ovulation. FIG. 10 is a schematic showing the injection of hormones into mice to cause follicle maturation and injection of compound 15.

Figure 11:
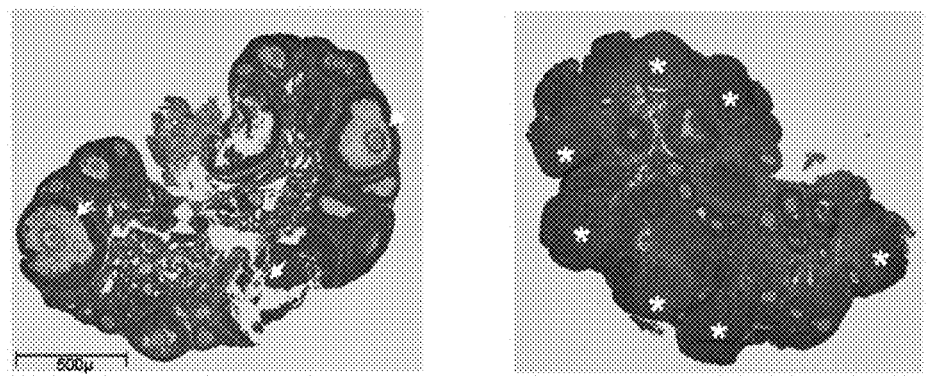
FIG. 11 illustrates the disruption of ovulation in mice by administration of Compound 15.

As illustrated in FIG. 11, Compound 15-treated ovaries have fewer clearly luteinized CL-like structures (asterisks). Compound 15-treated ovaries have unruptured antral follicle-like structures containing oocytes surrounded by expanded cumulus complex (COC)(arrows), indicating that compound 15 inhibits ovulation. These data indicate that an N-cadherin antagonist such as compound 15 can serve as a non-hormonal contraceptive.

Example 20

Multiple myeloma (MM) is a haematological malignancy characterized by the clonal proliferation of antibody-producing plasma cells within the bone marrow microenvironment.

This example illustrates that Compound 15 can inhibit growth of multiple myeloma (MM) tumors in vivo.

The C57BL/KaLwRij (Rij) murine model of Multiple Myeloma (MM) has many of the clinical and histopathological features that are characteristic of human MM disease (Radl, J., et al., 1988, Am. J. Pathol., 132, 593-597; Vanderkerken, K., et al., 1997, Br. J. Cancer, 76, 451-460.) One of the cell lines derived from aging Rij mice presenting with MM, the 5TGM1 line (Garrett, I. R., et al., 1997, Bone, 20, 515-520; Oyajobi, B. O., et al., 2007, Molecular Cancer Therapeutics, 6, 1701-1708) exhibits many of the properties of the human disease, including bone marrow homing and osteolytic bone disease.

In these experiments, 5TGM1 mouse MM plasma cells (expressing a dual GFP and luciferase reporter construct (Noll Neoplasia 2014; Cheong 2015)) were maintained in Iscove's modified Dulbecco's medium (IMDM) with 20% fetal calf serum (FCS; Thermo Fisher Scientific, Waltham, Mass., USA) and supplements.

Figure 12:
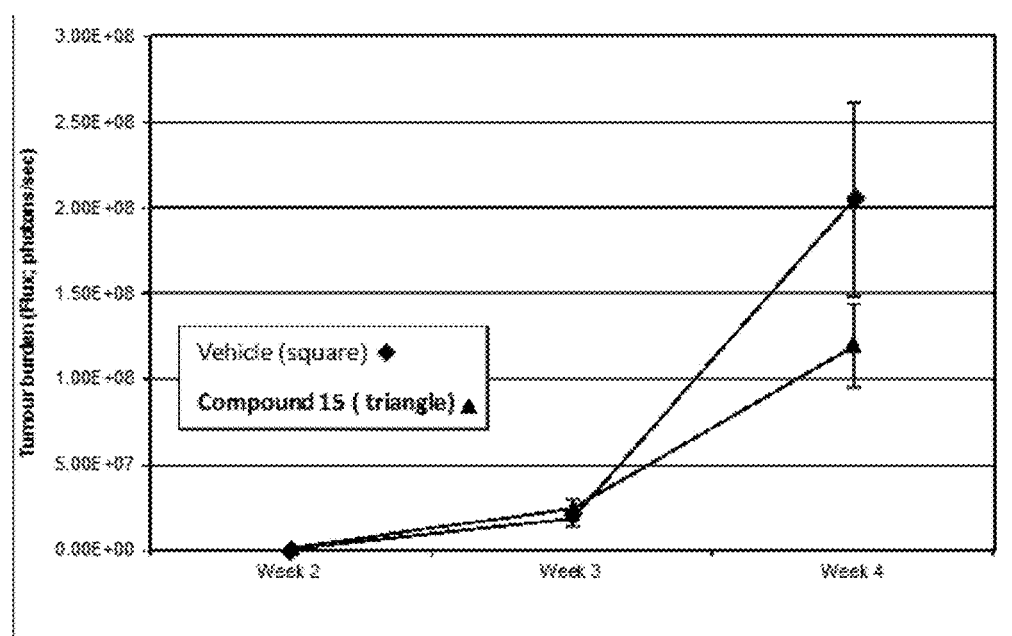
FIG. 12 illustrates that Compound 15 decreases MM tumor burden in mice.

C57Bl/KaLwRij mice (aged 6-8 weeks) were used for all in vivo studies. For MM tumor studies, mice were inoculated with $5 \times 10^5$ 5TGM1 cells in 100 µl phosphate buffered saline by intravenous injection (i.v.) via the tail vein. Total body tumor burden was assessed at days 14, 21 and 28 using the Xenogen IVIS, as previously described (Mrozik, K. M., et al., 2015, Br. J. Haematol. 171, 387-399.). All animals used for therapy studies were randomized by age, sex and, where appropriate, tumor burden. Compound 15 was dissolved at a concentration of 10 mg/ml in saline containing 40% 2-hydroxyproprol-β-cyclodextrin. Either compound 15 (50 mg/kg/day) (N=8) or vehicle (40% 2-hydroxyproprol-β-cyclodextrin in saline) (N=7) alone was administered to mice i.p. commencing 15 minutes prior to 5TGM1 cell injection for 5 days. As shown in FIG. 12, Compound 15 caused a decrease in tumour burden. Compound 15 is therefore effective for treatment of MM.

Example 21

This example illustrates the effects of an N-cadherin antagonist of the present teachings (compound 15) on multiple myeloma (MM) cell viability.

Myeloma cells MM.1S (American Type Culture Collection, Manassas, Va., USA) were cultured in RPMI-1640 medium supplemented with 10% fetal bovine serum (Thermo Fisher Scientific, Waltham, Mass., USA), 100 U/mL of penicillin, and 100 mg/mL of streptomycin. The cells were grown at 37° C. in a humidified incubator with 5% $CO_2$.

Figure 13:
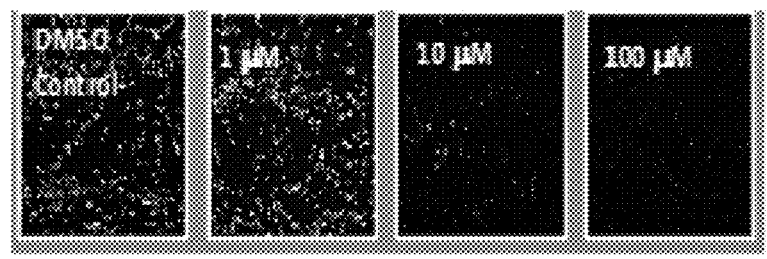
FIG. 13 illustrates the killing of MM.1S cells by Compound 15.
Figure 13:
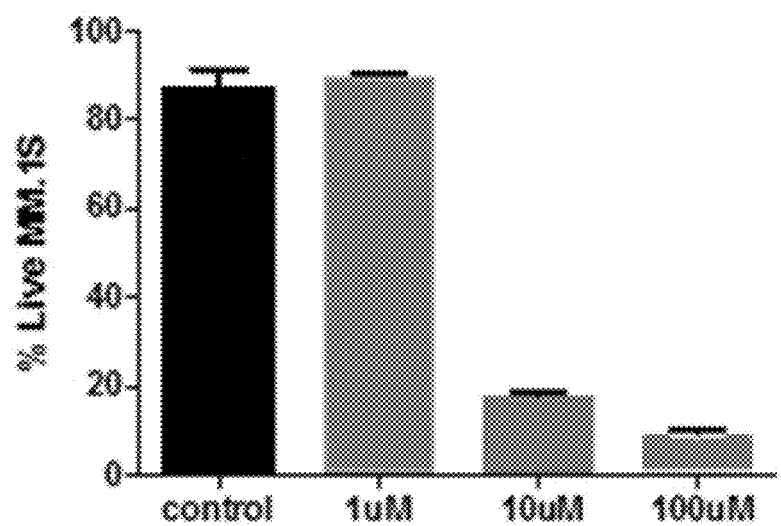

In these experiments, MM.1S cells were pre-labeled with CellTrace Violate (Thermo Fisher Scientific), plated on 96-well plates ($1.5 \times 10^5$ cells/well) and treated with varying concentrations of compound 15 (1-100 μM) or DMSO (vehicle control). High content screening (CellInsight CX5, Thermo Fisher Scientific) was utilized to quantify the number of live cells (i.e. calcein AM+ cells) 24 h post-treatment. FIG. 13 presents photomicrographs (upper panel) and quantitative data (lower panel) of cells treated with compound 15. As shown in FIG. 13, compound 15 caused a decrease in the number of live cells on the substratum at concentrations of 10 and 100 μM. These results further illustrate that compound 15 is useful for treating Multiple Myeloma.

All publications cited herein are incorporated by reference, each in its entirety.

What is claimed is:

1. A compound or pharmaceutically acceptable salt thereof, wherein the compound is (S)-1-(3,4-dichlorophenoxy)-3-(4-(((S)-2-hydroxy-3-(4-methoxyphenoxy)propyl)amino)piperidin-1-yl)propan-2-ol (15)

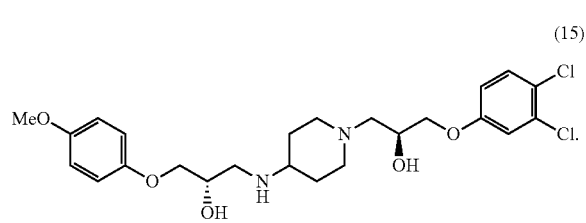 [SMILES: COc1ccc(OC[C@@H](O)CNC2CCN(C[C@H](O)COc3ccc(Cl)c(Cl)c3)CC2)cc1]

2. A composition comprising:
the compound or a pharmaceutically acceptable salt thereof in accordance with claim 1; and a pharmaceutically acceptable carrier, excipient or diluent.

3. A composition in accordance with claim 2, further comprising a heterologous compound selected from the group consisting of a pharmaceutically active substance, a detectable marker and a solid support.

4. A composition in accordance with claim 3, wherein the pharmaceutically active substance is selected from the group consisting of an analgesic, an anesthetic, an antianginal, an antifungal, an antibiotic, an anticancer drug, an anti-inflammatory, an anthelmintic, an antidepressant, an antidote, an antiemetic, an antihistamine, an antihypertensive, an antimalarial, an antimicrotubule agent, an antimigraine agent, an antimicrobial, an antipsychotic, an antipyretic, an antiseptic, an anti-signaling agent, an antiarthritic, an antithrombin agent, an antituberculotic, an antitussive, an antiviral, an appetite suppressant, a cardioactive drug, a chemical dependency drug, a cathartic, a chemotherapeutic agent, a coronary vasodilator, a cerebral vasodilator, a peripheral vasodilator, a contraceptive agent, depressants, a diuretic, an expectorant, a growth factor, a hormonal agent, a hypnotic, an immunosuppression agent, an immunostimulatory agent, a narcotic antagonist, a parasympathomimetic, a sedative, a stimulant, a sympathomimetic, a toxin, a tranquilizer and a urinary anti-infective.

5. A composition in accordance with claim 2, wherein the detectable marker is selected from the group consisting of a polypeptide antigen that can be detected with an antibody and an enzyme that can be detected with a chromogenic substrate or a fluorogenic substrate.

6. A composition in accordance with claim 2, further comprising a solid support.

7. A composition in accordance with claim 6, wherein the solid support is a polymeric matrix.

8. A patch for transdermal drug delivery, comprising:
a matrix; and
the compound or pharmaceutically acceptable salt thereof of claim 1.

9. A patch for transdermal drug delivery in accordance with claim 8, further comprising at least one additional pharmaceutical agent.

10. A patch for transdermal delivery in accordance with claim 9, wherein the at least one additional pharmaceutical agent is selected from the group consisting of an anti-inflammatory drug, an analgesic, an antibiotic, an anticoagulant, an antidepressant, an antihypertensive drug, an antipsychotic drug, a sedative and a steroid.

* * * * *

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: calcium binding motif
<220> FEATURE:
<221> NAME/KEY: MISC_FEATURE
<222> LOCATION: (2)..(2)
<223> OTHER INFORMATION: Xaa is any naturally occurring amino acid

<400> SEQUENCE: 1

Asp Xaa Asn Asp Asn
1               5

<210> SEQ ID NO 2
<211> LENGTH: 4
<212> TYPE: PRT
<213> ORGANISM: Artificial Sequence
<220> FEATURE:
<223> OTHER INFORMATION: calcium binding motif
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (3)..(3)
<223> OTHER INFORMATION: Xaa is any naturally occurring amino acid

<400> SEQUENCE: 2

Xaa Asp Xaa Glu
1

<210> SEQ ID NO 3
<211> LENGTH: 4
<212> TYPE: PRT
<213> ORGANISM: Artificial Sequence
<220> FEATURE:
<223> OTHER INFORMATION: calcium binding motif

<400> SEQUENCE: 3

Asp Val Asn Glu
1

<210> SEQ ID NO 4
<211> LENGTH: 4
<212> TYPE: PRT
<213> ORGANISM: Artificial Sequence
<220> FEATURE:
<223> OTHER INFORMATION: calcium binding motif

<400> SEQUENCE: 4

Leu Asp Arg Glu
1
```

```
<210> SEQ ID NO 5
<211> LENGTH: 6
<212> TYPE: PRT
<213> ORGANISM: Artificial Sequence
<220> FEATURE:
<223> OTHER INFORMATION: Trp-containing CAR sequence
<220> FEATURE:
<221> NAME/KEY: MISC_FEATURE
<222> LOCATION: (1)..(1)
<223> OTHER INFORMATION: aspartic acid or glutamic acid
<220> FEATURE:
<221> NAME/KEY: MISC_FEATURE
<222> LOCATION: (4)..(4)
<223> OTHER INFORMATION: isoleucine, valine or methionine
<220> FEATURE:
<221> NAME/KEY: MISC_FEATURE
<222> LOCATION: (5)..(5)
<223> OTHER INFORMATION: proline or alanine

<400> SEQUENCE: 5

Xaa Trp Val Xaa Xaa Pro
1               5

<210> SEQ ID NO 6
<211> LENGTH: 4
<212> TYPE: PRT
<213> ORGANISM: Artificial Sequence
<220> FEATURE:
<223> OTHER INFORMATION: CAR sequence

<400> SEQUENCE: 6

Leu Tyr His Tyr
1
```